(12) United States Patent
Bjore et al.

(10) Patent No.: US 7,648,985 B2
(45) Date of Patent: Jan. 19, 2010

(54) OXABISPIDINE COMPOUNDS AND THEIR USE IN THE TREATMENT OF CARDIAC ARRHYTHMIAS

(75) Inventors: Annika Bjore, Molndal (SE); Ulrik Gran, Molndal (SE); Peter Bonn, Molndal (SE); Johan Kajanus, Molndal (SE); Christina Olsson, Molndal (SE); Fritiof Ponten, Molndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/570,451

(22) PCT Filed: Jun. 13, 2005

(86) PCT No.: PCT/SE2005/000891

§ 371 (c)(1),
(2), (4) Date: Dec. 12, 2006

(87) PCT Pub. No.: WO2005/123748

PCT Pub. Date: Dec. 29, 2005

(65) Prior Publication Data

US 2009/0005558 A1    Jan. 1, 2009

(30) Foreign Application Priority Data

Jun. 15, 2004    (SE) .................................... 0401539

(51) Int. Cl.
C07D 513/00    (2006.01)
A61K 31/535    (2006.01)

(52) U.S. Cl. ..................... 514/230.5; 544/74
(58) Field of Classification Search ................... 544/74; 514/230.5
See application file for complete search history.

(56) References Cited

U.S. PATENT DOCUMENTS

| 3,196,154 | A | 7/1965 | Steck et al. |
| 3,503,939 | A | 3/1970 | Williams et al. |
| 3,962,449 | A | 6/1976 | Binnig et al. |
| 4,459,301 | A | 7/1984 | Binnig et al. |
| 4,533,713 | A | 8/1985 | Howells |

(Continued)

FOREIGN PATENT DOCUMENTS

| EP | 0306871 A2 | 3/1989 |
| EP | 0308843 A2 | 3/1989 |
| EP | 0655228 A1 | 5/1995 |
| EP | 1330461 | 4/2002 |
| EP | 1330462 | 4/2002 |
| EP | 1235831 | 3/2005 |
| EP | 1559717 | 3/2005 |
| GB | 1256850 | 12/1971 |
| HU | 8200945 | 4/1988 |
| JP | 5772977 | 5/1982 |
| JP | 6284070 | 10/1994 |
| JP | 6284071 | 10/1994 |
| JP | 2003512352 | 4/2003 |
| WO | 91/07405 A1 | 5/1991 |
| WO | 99/31100 A1 | 6/1999 |
| WO | 0061569 | 10/2000 |
| WO | 01/28992 A2 | 4/2001 |
| WO | 02/28863 A1 | 4/2002 |
| WO | 02/28864 A1 | 4/2002 |
| WO | 02/83690 A1 | 4/2002 |
| WO | 02/83691 AW | 4/2002 |
| WO | 02083688 | 10/2002 |
| WO | 03101956 | 11/2003 |
| WO | 2004035592 | 4/2004 |
| WO | 2005123748 | 12/2005 |

OTHER PUBLICATIONS

Office Action dated Nov. 17, 2008 cited in copending U.S. Appl. No. 12/029,483.
Office Action dated Dec. 15, 2008 cited in copending U.S. Appl. No. 12/029,501.
U.S. Office Action dated Jan. 7, 2009 cited in copending U.S. Appl. No. 12/028,955.
Preliminary Report: Effect of Encainide and Flecainide on Mortality in a Randomized Trial Of Arrhythmia Suppression After Myocardial Infarction, New England Journal of Medicine, Aug. 10, 1989, pp. 406-412, vol. 321, No. 6.
Bogousslavsky, Julien et al., Pure midbrain infarction: Clinical syndromes, MRI, and etiologic patterns, Neurology, 1994, pp. 2032-2040, vol. 44.
Yoshidome, Toshifumi et al., Infrared Spectroscopic Analyses of Transformations of Chemical Species on the Silica Highly-Reacted with Gaseous BF3, Analytical Sciences, Mar. 2003, pp. 429-435, vol. 19.

(Continued)

*Primary Examiner*—Kahsay T Habte
(74) *Attorney, Agent, or Firm*—Pepper Hamilton LLP

(57) ABSTRACT

There is provided compounds of formula (I), wherein $R^1$, $R^2$, $R^3$, $R^4$, $R^{41}$ to $R^{46}$, A, B and G have meanings given in the description, which are useful in the prophylaxis and in the treatment of arrhythmias, in particular atrial and ventricular arrhythmias.

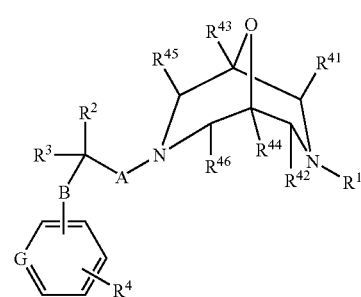

1 Claim, No Drawings

U.S. PATENT DOCUMENTS

| | | | |
|---|---|---|---|
| 4,550,112 | A | 10/1985 | Schoen et al. |
| 4,556,662 | A | 12/1985 | Binnig et al. |
| 5,140,033 | A | 8/1992 | Schriewer et al. |
| 5,468,858 | A | 11/1995 | Berlin et al. |
| 5,831,099 | A | 11/1998 | Dave et al. |
| 6,559,143 | B1 * | 5/2003 | Bjore et al. ............... 514/230.5 |
| 6,936,712 | B1 | 8/2005 | Pavey |
| 7,164,017 | B2 | 1/2007 | Cladingboel et al. |
| 7,169,921 | B2 | 1/2007 | Cheema et al. |
| 7,217,708 | B2 * | 5/2007 | Barnwell et al. ......... 514/230.5 |
| 7,354,917 | B2 | 4/2008 | Bjore et al. |
| 2004/0133000 | A1 | 7/2004 | Cheema et al. |
| 2007/0197519 | A1 | 8/2007 | Cheema et al. |

OTHER PUBLICATIONS

Paroczai, M. and Karpati, E., Investigations to Characterize A New antiarrhythmic Drug Bisaramil, Pharamcological Research, 1991, pp. 149-162, vol. 24, No. 2.

Garrison, Gregory L. et al., Novel 3,7-Diheterabicyclo[3.3. 1]nonanes That Possess Predominant Class III Antiarrhythmic Activity in 1-4 Day Post Infarction Dog Models: X-ray Diffraction Analysis of 3-[4-(1h-Imidazol-1-yl) benzoyl]-7-isopropyl-3,7-diazabicyclo[3.3.1]nonane Dihydroperchlorate, Journal of Medicinal Chemistry, 1986, pp. 2559-2570, vol. 39, No. 13.

Weinges, Klaus et al., [Uber den mechanismus der saurekatalysierten Kondensations-reaktionen der Hydroxy-flavane und Hydroxy-flavanole-(3)], Chem. Ber., 1963, pp. 2870-2878, vol. 96.

Nemec et al., "Pharmacotherapy of atrial fibrillation," Expert Opinion of Pharmacotherapy (1999) 1(1):81-96.

Lange et al., "Facile Conversion of Primary and Secondary Alcohols to Alkyl Iodides," Synthetic Communication (1990) 20(10):1473-1479.

Nelson et al., "Synthesis of 2,5- and 2,6-bis(bromomethyl)-1,4-diphenylpiperazines and their conversion into 2,5-diphenyl-2,5-diazabicyclo[2.2.2]octane," J Org Chem (1971) 36(22):3361-3365.

Villa et al., "3,8-diazabicyclo—[3.2.1]-octane derivatives as analogues of ambasilide, a Class III antiarrhythmic agent," Eur J. Med Chem (2001) 36(6):495-506.

Wang et al., "Class III antiarrhythmic drug action in experimental atrial fibrillation. Differences in reverse use dependence and effectiveness between d-sotalol and the new antiarrhythmic drug ambasilide," Circulation (1994) 90 (4):2032-2040.

Tsukerman et al., "Basicity and Structure of Heterocyclic Alpha, Beta- Unsaturated Ketones," Zh Obshch Khim (1963) 33(9):3110-3112.

Notice of Allowance dated Nov. 9, 2007 for copending U.S. Appl. No. 11/570,439.

Office Action dated Oct. 2, 2007 received in Copending U.S. Appl. No. 11/612,826.

Notice of Allowance dated Mar. 2, 2005 for copending U.S. Appl. No. 10/474,585.

Notice of Allowance dated Feb. 14, 2006 for copending U.S. Appl. No. 10/474,593.

Office Action dated Mar. 20, 2006 for copending U.S. Appl. No. 10/474,593.

Office Action dated Jun. 23, 2006 for copending U.S. Appl. No. 10/474,593.

Rubtsov et al., "Synthesis and pharmacological investigation of derivatives of 9-methyl-3,9-diazabicyclo-(3,3,1)-nonane," J Med Pharm Chem (1961) 3(3):441-459.

Kyi et al., "Synthetic analgesics and related compounds. Part II. Some derivatives of 3:7-diazabicyclo[3:3:1]nonane (Bispidine)," J. Chem Soc. (1951) 1706-1705.

Nikitskaya et al., "Bicyclic systems based on 2,6-lutidine. V. Bisquaternary salts of—bis(9-methyl-3,9-diazabicyclo [3.3. 1]nonan-3-yl)alkanes," Zh. Obshich. Khim. (1961) 31:3202-3205; Chemical Abstracts, vol. 56 (1962), Abstract No. 15491.

Jeyaraman et al., "Chemistry of 3-azabicyclo[3.3.1]nonanes," Chem Rev (1981) 81(2):149-174.

Steck et al., "3-Substituted 9-Methyl-3,9-Diazabicyclo[3.3. 1]nonanes," J Org Chem (1963) 28(9):2233-2238.

Barnes et al., "The sunthesis of the 3,9-diazabicyclo [3.3.1]nonane ring system," J Am Chem Soc (1953) 75:975-977.

Paulder et al., "1,5-Bis(p-toluenesulfonyl)-3,7-Dihydroxyoctahydro-1,5-diazocine," J Org Chem (1966) 31(1):277-281.

Dave et al., "Facile Preparation of 3,7-Diazabicyclo[3.3.0]octane and 3,7,10-Triheterocyclic [3.3.3]Propellane Ring Systems from 1,5-Diazacyclooctane 3,7-Derivatives," J Org Chem (1996) 61(25):8897-8903.

Chapman et al., "Nitrolysis of a Highly Deactivated Amide by Protonitronium. Synthesis and Structure of HNFX(1)," J Org Chem (1999) 64(3):960-965.

Chapman et al., "Difluoramination of Heterocyclic Ketones: Control of Microbasicity," J Org Chem (1998) 63 (5):1566-1570.

Paudler et al., "3,7-Disubstituted octahydro-1,5-diazocines. Their conversion into tetrahydro-1,5-diazocines and to ring-contracted products," J Org Chem (1967) 32(8):2425-2430.

Cignarella et al., "Intramolecular acyl migration in the 3,9-diazabicycla [3.3.1]-nonane series," Gazz. Chim. Ital., (1963) 93(4):320-328; chemical abstracts, vol. 59 (1963), Abstract No. 7474.

Cignarella et al., "Investigation on 3,9-diazabicyclo[3.3.1]nonanes. Sterochemistry and analgesic activity of 3,9-diazabicyclo [3.3.1]octane derivatives," Gazz Chim Ital (1963) 93:226-37; Chemical Abstracts, vol. 59 (1963), Abstract No. 2822.

Stetter et al., "Synthese des 1,3-Diaza-6-oxa-adamantans," Chem Ber (1963) 96(11):2827-2830.

Chen et al., "High-Performance Liquid Chromatographic Determination of SAZ-VII-22, a Novel Antiarrhythmic Agent, in Dog Plasma and Urine," Anal Sci (1993) 9(3):429-431.

Abstract No. 1987:637909, CA, vol. 107 (1987).

Abstract No. 1987:146842, CA, vol. 107 (1987).

Notice of Allowance dated Mar. 2, 2009 received in copending U.S. Appl. No. 12/029,483.

* cited by examiner

OXABISPIDINE COMPOUNDS AND THEIR USE IN THE TREATMENT OF CARDIAC ARRHYTHMIAS

CROSS-REFERENCE TO RELATED APPLICATIONS

This application is the U.S. National Stage filing of International Application Serial No. PCT/SE05/00891 filed Jun. 13, 2005, which is incorporated herein by reference in its entirety.

FIELD OF THE INVENTION

This invention relates to novel pharmaceutically useful compounds, in particular compounds which are useful in the treatment of cardiac arrhythmias.

BACKGROUND AND PRIOR ART

Cardiac arrhythmias may be defined as abnormalities in the rate, regularity, or site of origin of the cardiac impulse or as disturbances in conduction which causes an abnormal sequence of activation. Arrhytnias may be classified clinically by means of the presumed site of origin (i.e. as supraventricular, including atrial and atrioventricular, arrhythmias and ventricular arrhythmias) and/or by means of rate (i.e. bradyarrhythmias (slow) and tachyarrhythmias (fast)).

In the treatment of cardiac arrhythmias, the negative outcome in clinical trials (see, for example, the outcome of the Cardiac Arrhythmia Suppression Trial (CAST) reported in *New England Journal of Medicine*, 321, 406 (1989)) with "traditional" antiarrhythmic drugs, which act primarily by slowing the conduction velocity (class I antiarrhythmic drugs), has prompted drug development towards compounds which selectively delay cardiac repolarization, thus prolonging the QT interval. Class III antiarrhythmic drugs may be defined as drugs which prolong the trans-membrane action potential duration (which can be caused by a block of outward $K^+$ currents or from an increase of inward ion currents) and refractoriness, without affecting cardiac conduction.

One of the key disadvantages of hitherto known drugs which act by delaying repolarization (class III or otherwise) is that they all are known to exhibit a unique form of proarrhythmia known as torsades de pointes (turning of points), which may, on occasion be fatal. From the point of view of safety, the minimisation of this phenomenon (which has also been shown to be exhibited as a result of administration of non-cardiac drugs such as phenothiazines, tricyclic antidepressants, antihistamines and antibiotics) is a key problem to be solved in the provision of effective antiarrhythmic drugs.

Antiarrhythmic drugs based on bispidines (3,7-diazabicyclo[3.3.1]nonanes), are known from inter alia international patent applications WO 91/07405 and WO 99/31100, European patent applications 306 871, 308 843 and 655 228 and U.S. Pat. Nos. 3,962,449, 4,556,662, 4,550,112, 4,459,301 and 5,468,858, as well as journal articles including, inter alia, *J. Med. Chem.* 39, 2559, (1996), *Pharmacol. Res.*, 24, 149 (1991), *Circulation*, 90, 2032 (1994) and *Anal. Sci.* 9, 429, (1993).

Certain oxabispidine compounds are disclosed as chemical curiosities in *Chem. Ber.*, 96, 2872 (1963). The use of certain other oxabispidine compounds in the treatment of cardiac arrhythmias is disclosed in WO 01/28992. Methods for the preparation of such oxabispidine compounds are disclosed in WO 02/28863, WO 02/28864, WO 02/83690 and WO 02/83691. Oxabispidine compounds in which one or both of the N-atoms bears a substituent that includes an "in-chain" sulfonamide group are neither disclosed nor suggested.

We have surprisingly found that a novel group of oxabispidine-based compounds exhibit electrophysiological activity and are therefore expected to be useful in the treatment of cardiac arrhythmias. The novel group of oxabispidine-based compounds has advantageous properties compared to compounds of the prior art, such as enhanced potency, enhanced selectivity, and/or reduction of total clearance. These advantageous properties can distinguish the use of such compounds as pharmaceutical agents by lowering the daily clinical dose, lengthening the duration of action, and/or improving the side effect profile.

DISCLOSURE OF THE INVENTION

According to the invention there is provided compounds of formula I,

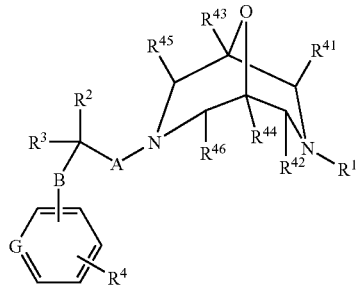

wherein
$R^1$ represents $C_{1-12}$ alkyl (which alkyl group is optionally substituted by one or more groups selected from halo, cyano, nitro, aryl, Het$^1$, —N($R^{5a}$)$R^6$, —C(O)$R^{5b}$, —O$R^{5c}$, —C(O)X$R^7$, —C(O)N($R^{8a}$)$R^{5d}$, —OC(O)N($R^{8b}$)$R^{5e}$, —S(O)$_2R^{9a}$, —S(O)$_2$N($R^{9b}$)$R^{9c}$ and —N($R^{9b}$)S(O)$_2R^{9d}$) or $R^1$ represents —C(O)X$R^7$, —C(O)N($R^{8a}$)$R^{5d}$ or —S(O)$_2R^{9a}$;

$R^{5a}$ represents H or $C_{1-6}$ alkyl (which latter group is optionally substituted by one or more substituents selected from —OH, halo, cyano, nitro, —S(O)$_2$N($R^{9b}$)$R^{9c}$ and —N($R^{9b}$)S(O)$_2R^{9d}$);

$R^{5b}$ to $R^{5e}$ independently represent, at each occurrence when used herein, H, $C_{1-6}$ alkyl (which latter group is optionally substituted by one or more substituents selected from —OH, halo, cyano, nitro, aryl, Het$^2$, —S(O)$_2$N($R^{9b}$)$R^{9c}$ and —N($R^{9b}$)S(O)$_2R^{9d}$), aryl or Het$^3$, or $R^{5d}$ or $R^{5e}$, together with, respectively, $R^{8a}$ or $R^{8b}$, may represent $C_{3-6}$ alkylene (which alkylene group is optionally interrupted by an O atom and/or is optionally substituted by one or more $C_{1-3}$ alkyl groups);

$R^6$ represents H, $C_{1-6}$ alkyl (optionally substituted by one or more substituents selected from —OH, halo, cyano, nitro, aryl, —S(O)$_2$N($R^{9b}$)$R^{9c}$ and —N($R^{9b}$)S(O)$_2R^{9d}$), aryl, —C(O)$R^{10a}$, —C(O)O$R^{10b}$ or —C(O)N(H)$R^{10c}$ or —S(O)$_2R^{10d}$;

$R^{10a}$, $R^{10b}$, $R^{10c}$ and $R^{10d}$ independently represent $C_{1-6}$ alkyl (optionally substituted by one or more substituents selected from —OH, halo, cyano, nitro and aryl), aryl, or $R^{10a}$ represents H;

$R^7$ represents, at each occurrence when used herein, $C_{1-12}$ alkyl (optionally substituted by one or more substituents selected from —OH, halo, cyano, nitro, aryl, $C_{1-6}$ alkoxy, $Het^4$, —S(O)$_2$N(R$^{9b}$)R$^{9c}$ and —N(R$^{9b}$)S(O)$_2$R$^{9d}$);

$R^{8a}$ and $R^{8b}$ independently represent H, $C_{1-12}$ alkyl, $C_{1-6}$ alkoxy (which latter two groups are optionally substituted by one or more substituents selected from —OH, halo, cyano, nitro, $C_{1-4}$ alkyl, $C_{1-4}$ alkoxy, —S(O)$_2$N(R$^{9b}$)R$^{9c}$ and —N(R$^{9b}$)S(O)$_2$R$^{9d}$), -D-aryl, -D-aryloxy, -D-Het$^5$, -D-N(H)C(O)R$^{11a}$, -D-S(O)$_2$R$^{12a}$, -D-C(O)R$^{11b}$, -D-C(O)OR$^{12b}$, -D-C(O)N(R$^{11c}$)R$^{11d}$, or $R^{8a}$ or $R^{8b}$, together with, respectively, $R^{5d}$ or $R^{5e}$, may represent $C_{3-6}$ alkylene (which alkylene group is optionally interrupted by an O atom and/or is optionally substituted by one or more $C_{1-3}$ alkyl groups);

$R^{11a}$ to $R^{11d}$ independently represent H, $C_{1-6}$ alkyl (optionally substituted by one or more substituents selected from —OH, halo, cyano, nitro and aryl), aryl, or $R^{11c}$ and $R^{11d}$ together represent $C_{3-6}$ alkylene;

$R^{12a}$ and $R^{12b}$ independently represent $C_{1-6}$ alkyl (optionally substituted by one or more substituents selected from —OH, halo, cyano, nitro and aryl) or aryl;

D represents, at each occurrence when used herein, a direct bond or $C_{1-6}$ alkylene;

X represents O or S;

$R^{9a}$ represents, at each occurrence when used herein, $C_{1-6}$ alkyl (optionally substituted by one or more substituents selected from —OH, halo, cyano, nitro, aryl, —S(O)$_2$N(R$^{9b}$)R$^{9c}$ and —N(R$^{9b}$)S(O)$_2$R$^{9d}$) or aryl;

$R^{9b}$ represents, at each occurrence when used herein, H or $C_{1-6}$ alkyl;

$R^{9c}$ and $R^{9d}$ independently represent, at each occurrence when used herein, $C_{1-6}$ alkyl (optionally substituted by one or more substituents selected from —OH, halo, cyano, nitro, aryl and Het$^6$), aryl or Het$^7$, or $R^{9c}$ represents H;

$R^2$ represents H, halo, $C_{1-6}$ alkyl, —OR$^{13}$, -E-N(R$^{14}$)R$^{15}$ or, together with $R^3$, represents =O;

$R^3$ represents H, $C_{1-6}$ alkyl or, together with $R^2$, represents =O;

$R^{13}$ represents H, $C_{1-6}$ alkyl, -E-aryl, -E-Het$^8$, —C(O)R$^{16a}$, C(O)OR$^{16b}$ or —C(O)N(R$^{17a}$)R$^{17b}$;

$R^{14}$ represents H, $C_{1-6}$ alkyl, -E-aryl, -E-Het$^9$, —C(O)R$^{16a}$, —C(O)OR S(O)$_2$R$^{16c}$, —[C(O)]$_p$N(R$^{17a}$)R$^{17b}$ or —C(NH)NH$_2$;

$R^{15}$ represents H, $C_{1-6}$ alkyl, -E-aryl or —C(O)R$^{16d}$;

$R^{16a}$ to $R^{16d}$ independently represent, at each occurrence when used herein, $C_{1-6}$ alkyl (optionally substituted by one or more substituents selected from halo, aryl and Het$^{10}$), aryl, Het$^{11}$, or $R^{16a}$ and $R^{16d}$ independently represent H;

$R^{17a}$ and $R^{17b}$ independently represent, at each occurrence when used herein, H or $C_{1-6}$ alkyl (optionally substituted by one or more substituents selected from halo, aryl and Het$^{12}$), aryl, Het$^{13}$, or together represent $C_{3-6}$ alkylene, optionally interrupted by an O atom;

E represents, at each occurrence when used herein, a direct bond or $C_{1-4}$ alkylene;

p represents 1 or 2;

Het$^1$ to Het$^{13}$ independently represent five- to twelve-membered heterocyclic groups containing one or more heteroatoms selected from oxygen, nitrogen and/or sulfur, which groups are optionally substituted by one or more substituents selected from —OH, oxo, halo, cyano, nitro, $C_{1-6}$ alkyl, $C_{1-6}$ alkoxy, aryl, aryloxy, N(R$^{18a}$)R$^{18b}$, C(O)R$^{18c}$, —C(O)OR$^{18d}$, —C(O)N(R$^{18e}$)R$^{18f}$, —N(R$^{18g}$)C(O)R$^{18h}$, —S(O)$_2$N(R$^{18i}$)R$^{18j}$ and —N(R$^{18k}$)S(O)$_2$R$^{18l}$;

$R^{18a}$ to $R^{18l}$ independently represent $C_{1-6}$ alkyl, aryl or $R^{18a}$ to $R^{18k}$ independently represent H;

A represents a direct bond, -J-, -J-N(R$^{19a}$)—, -J-S(O)$_2$N(R$^{19b}$)—, -J-N(R$^{19c}$)S(O)$_2$— or -J-O— (in which latter four groups, -J is attached to the oxabispidine ring nitrogen);

B represents —Z—{[C(O)]$_a$C(H)(R$^{20a}$)}$_b$—, —Z—[C(O)]$_c$N(R$^{20b}$)—, —Z—N(R$^{20c}$)S(O)$_2$—, —Z—S(O)$_2$N(R$^{20d}$)—, —Z—S(O)$_n$—, —Z—O— (in which latter six groups, Z is attached to the carbon atom bearing $R^2$ and $R^3$), —N(R$^{20e}$)—Z—, —N(R$^{20f}$)S(O)$_2$—Z—, —S(O)$_2$N(R$^{20g}$)—Z— or —N(R$^{20h}$)C(O)O—Z—(in which latter four groups, Z is attached to the phenyl or pyridyl group that is optionally substituted by $R^4$);

J represents $C_{1-6}$ alkylene optionally interrupted by —S(O)$_2$N(R$^{19d}$)— or —N(R$^{19e}$)S(O)$_2$— and/or optionally substituted by one or more substituents selected from —OH, halo and amino;

Z represents a direct bond or $C_{1-4}$ alkylene, optionally interrupted by —N(R$^{20i}$)S(O)$_2$— or —S(O)$_2$N(R$^{20j}$)—;

a, b and c independently represent 0 or 1;

n represents 0, 1 or 2;

$R^{19a}$ to $R^{19e}$ independently represent, at each occurrence when used herein, H or $C_{1-6}$ alkyl;

$R^{20a}$ represents H or, together with a single $R^4$ substituent at a position on the phenyl or pyridyl group that is ortho- to the position at which the group B is attached, $R^{20a}$ represents $C_{2-4}$ alkylene optionally interrupted or terminated by O, S, N(H) or N($C_{1-6}$ alkyl);

$R^{20b}$ represents H, $C_{1-6}$ alkyl or, together with a single $R^4$ substituent at a position on the phenyl or pyridyl group that is ortho- to the position at which the group B is attached, $R^{20b}$ represents $C_{2-4}$ alkylene;

$R^{20c}$ to $R^{20j}$ independently represent, at each occurrence when used herein, H or $C_{1-6}$ alkyl;

G represents CH or N;

$R^4$ represents one or more optional substituents selected from —OH, cyano, halo, nitro, $C_{1-6}$ alkyl (optionally terminated by —N(H)C(O)OR$^{21a}$), $C_{1-6}$ alkoxy, —N(R$^{22a}$)R$^{22b}$, —C(O)R$^{22c}$, —C(O)R$^{22d}$, —C(O)N(R$^{22e}$)R$^{22f}$, —N(R$^{22g}$)C(O)R$^{22h}$, —N(R$^{22i}$)C(O)N(R$^{22j}$)R$^{22k}$, —N(R$^{22m}$)S(O)$_2$R$^{21b}$, —S(O)$_2$N(R$^{22n}$)R$^{22o}$, —S(O)$_2$R$^{21c}$, —OS(O)$_2$R$^{21d}$ and aryl and an $R^4$ substituent in a position on the phenyl or pyridyl group that is ortho- to the position at which the group B is attached may
(i) together with $R^{20a}$, represent $C_{2-4}$ alkylene optionally interrupted or terminated by O, S or N(H) or N($C_{1-6}$ alkyl), or
(ii) together with $R^{20b}$, represent $C_{2-4}$ alkylene;

$R^{21a}$ to $R^{21d}$ independently represent $C_{1-6}$ alkyl;

$R^{22a}$ and $R^{22b}$ independently represent H, $C_{1-6}$ alkyl or together represent $C_{3-6}$ alkylene, resulting in a four- to seven-membered nitrogen-containing ring;

$R^{22c}$ to $R^{22o}$, independently represent H or $C_{1-6}$ alkyl; and $R^{41}$ to $R^{46}$ independently represent H or $C_{1-3}$ alkyl;

wherein each aryl and aryloxy group, unless otherwise specified, is optionally substituted;

provided that
(a) at least one of the following is the case
(i) $R^1$ represents $C_{1-12}$ alkyl (which alkyl group is substituted by one or more groups including at least one —S(O)$_2$N(R$^{9b}$)R$^{9c}$ and/or N(R$^{9b}$)S(O)$_2$R$^{9d}$ group),
(ii) A represents -J-S(O)$_2$N(R$^{9b}$)— or -J-N(R$^{19c}$)S(O)$_2$—,
(iii) J is interrupted by —S(O)$_2$N(R$^{19d}$)— or —N(R$^{19e}$)S(O)$_2$—, (iv) B represents —Z—N(R$^{20c}$)S(O)$_2$—, —Z—S(O)$_2$N(R$^{20d}$)—, —N(R$^{20f}$)S(O)$_2$—Z— or —S(O)$_2$N(R$^{20g}$)—Z—and/or (v) Z is interrupted by —N(R$^{20i}$)S(O)$_2$— or —S(O)$_2$N(R$^{20j}$)—;

(b) when A represents -J-N(R$^{19a}$)—, -J-N(R$^{19c}$)S(O)$_2$— or -J-O—, then:

(i) J does not represent C$_1$ alkylene or 1,1-C$_{2-6}$ alkylene; and (ii) B does not represent —N(R$^{20b}$)—, —N(R$^{20c}$)S(O)$_2$—, —S(O)$_n$—, —O—, —N(R$^{20f}$)S(O)$_2$—Z— or —N(R$^{20h}$)C(O)O—Z when R$^2$ and R$^3$ do not together represent =O; and (c) when R$^2$ represents —OR$^3$ or —N(R$^{14}$)(R$^{15}$), then:

(i) A does not represent -J-N(R$^{19a}$)—, -J-N(R$^{19c}$)S(O)$_2$— or -J-O—; and (ii) B does not represent —N(R$^{20b}$)—, —N(R$^{20c}$)S(O)$_2$—, —S(O)$_n$—, —O—, —N(R$^{20f}$)S(O)$_2$—Z— or —N(R$^{20h}$)C(O)O—Z—;

or a pharmaceutically acceptable derivative thereof.

For the avoidance of doubt it is to be understood that where in this specification a group is qualified by 'hereinbefore defined', 'defined hereinbefore' or 'defined above' the said group encompasses the first occurring and broadest definition as well as each and all of the particular definitions for that group.

Unless otherwise specified, alkyl groups and alkoxy groups as defined herein may be straight-chain or, when there is a sufficient number (i.e. a minimum of three) of carbon atoms be branched-chain, and/or cyclic. Further, when there is a sufficient number (i.e. a minimum of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated and/or interrupted by one or more oxygen and/or sulfur atoms. Unless otherwise specified, alkyl and alkoxy groups may also be substituted by one or more halo, and especially fluoro, atoms.

Unless otherwise specified, alkylene groups as defined herein may be straight-chain or, when there is a sufficient number (i.e. a minimum of two) of carbon atoms, be branched-chain. Such alkylene chains may also be saturated or, when there is a sufficient number (i.e. a minimum of two) of carbon atoms, be unsaturated and/or interrupted by one or more oxygen and/or sulfur atoms. Unless otherwise specified, alkylene groups may also be substituted by one or more halo atoms.

The term "aryl", when used herein, includes C$_{6-10}$ aryl groups such as phenyl, naphthyl and the like. The term "aryloxy", when used herein includes C$_{6-10}$ aryloxy groups such as phenoxy, naphthoxy and the like. For the avoidance of doubt, aryloxy groups referred to herein are attached to the rest of the molecule via the O-atom of the oxy-group. Unless otherwise specified, aryl and aryloxy groups may be substituted by one or more substituents including —OH, halo, cyano, nitro, C$_{1-6}$ alkyl, C$_{1-6}$ alkoxy, —N(R$^{22a}$)R$^{22b}$, —C(O)R$^{22c}$, —C(O)OR$^{22d}$, —C(O)N(R$^{2e}$)R$^{22f}$, —N(R$^{22g}$)C(O)R$^{22h}$, —N(R$^{22m}$)S(O)$_2$R$^{21b}$, —S(O)$_2$N(R$^{22n}$)R$^{22o}$, —S(O)$_2$R$^{21c}$, and/or OS(O)$_2$R$^{21d}$ (wherein R$^{21b}$ to R$^{21d}$ and R$^{22a}$ to R$^{22o}$ are as hereinbefore defined). When substituted, aryl and aryloxy groups are preferably substituted by between one and three substituents.

The term "halo", when used herein, includes fluoro, chloro, bromo and iodo.

Het (Het$^1$, Het$^2$, Het$^3$, Het$^4$, Het$^5$, Het$^6$, Het$^7$, Het$^8$, Het$^9$, Het$^{10}$, Het$^{11}$, Het$^{12}$ and Het$^{13}$) groups that may be mentioned include those containing 1 to 4 heteroatoms (selected from the group oxygen, nitrogen and/or sulfur) and in which the total number of atoms in the ring system are between five and twelve. Het (Het$^1$, Het$^2$, Het$^3$, Het$^4$, Het$^5$, Het$^6$, Het$^7$, Het$^8$, Het$^9$, Het$^{10}$, Het$^{11}$, Het$^{12}$ and Het$^{13}$) groups may be fully saturated, wholly aromatic, partly aromatic and/or bicyclic in character. Heterocyclic groups that may be mentioned include 1-azabicyclo[2.2.2]octanyl, benzimidazolyl, benzisoxazolyl, benzodioxanyl, benzodioxepanyl, benzodioxolyl, benzofuranyl, benzofurazanyl, benzomorpholinyl, 2,1,3-benzoxadiazolyl, benzoxazinonyl, benzoxazolidinyl, benzoxazolyl, benzopyrazolyl, benzo[e]pyrimidine, 2,1,3-benzothiadiazolyl, benzothiazolyl, benzothienyl, benzotriazolyl, chromanyl, chromenyl, cinnolinyl, 2,3-dihydrobenzimidazolyl, 2,3-dihydrobenzo[b]-furanyl, 1,3-dihydrobenzo[c]furanyl, 2,3-dihydropyrrolo[2,3-b]pyridinyl, dimethylisoxazolyl, dioxanyl, furanyl, hexahydropyrimidinyl, hydantoinyl, imidazolyl, imidazo[1,2-a]pyridinyl, imidazo[2,3-b]thiazolyl, indolyl, isoquinolinyl, isoxazolyl, maleimido, morpholinyl, oxadiazolyl, 1,3-oxazinanyl, oxazolyl, phthalazinyl, piperazinyl, piperidinyl, purinyl, pyranyl, pyrazinyl, pyrazolyl, pyridinyl, pyrimidinyl, pyrrolidinonyl, pyrrolidinyl, pyrrolinyl, pyrrolo[2,3-b]pyridinyl, pyrrolo[5,1-b]pyridinyl, pyrrolo[2,3-c]pyridinyl, pyrrolyl, quinazolinyl, quinolinyl, sulfolanyl, 3-sulfolenyl, 4,5,6,7-tetrahydrobenz-imidazolyl, 4,5,6,7-tetrahydrobenzopyrazolyl, 5,6,7,8-tetrahydrobenzo[e]-pyrimidine, tetrahydrofuranyl, tetrahydropyranyl, 3,4,5,6-tetrahydro-pyridinyl, 1,2,3,4-tetrahydropyrimidinyl, 3,4,5,6-tetrahydropyrimidinyl, thiadiazolyl, thiazolidinyl, thiazolyl, thienyl, thieno[5,1-c]pyridinyl, thiochromanyl, triazolyl, 1,3,4-triazolo[2,3-b]pyrimidinyl and the like.

Values of Het$^1$ that may be mentioned include 2,3-dihydrobenzo[b]furanyl, furanyl, imidazolyl, isoxazolyl, pyridinyl and thiazolyl.

Values of Het$^7$ that may be mentioned include imidazolyl and isoxazolyl.

Substituents on Het (Het$^1$, Het$^2$, Het$^3$, Het$^4$, Het$^5$, Het$^6$, Het$^7$, Het$^8$, Het$^9$, Het$^{10}$, Het$^{11}$, Het$^{12}$ and Het$^{13}$) groups may, where appropriate, be located on any atom in the ring system including a heteroatom. The point of attachment of Het (Het$^1$, Het$^2$, Het$^3$, Het$^4$, Het$^5$, Het$^6$, Het$^7$, Het$^8$, Het$^9$, Het$^{10}$, Het$^{11}$, Het$^{12}$ and Het$^{13}$) groups may be via any atom in the ring system including (where appropriate) a heteroatom, or an atom on any fused carbocyclic ring that may be present as part of the ring system. Het (Het$^1$, Het$^2$, Het$^3$, Het$^4$, Het$^5$, Het$^6$, Het$^7$, Het$^8$, Het$^9$, Het$^{10}$, Het$^{11}$, Het$^{12}$ and Het$^{13}$) groups may also be in the N- or S-oxidised form.

Pharmaceutically acceptable derivatives include salts and solvates. Salts which may be mentioned include acid addition salts.

Pharmaceutically acceptable derivatives also include, at the oxabispidine or (when G represents N) pyridyl nitrogens, C$_{1-4}$ alkyl quaternary ammonium salts and N-oxides, provided that when a N-oxide is present:

(a) no Het (Het$^1$, Het$^2$, Het$^3$, Het$^4$, Het$^5$, Het$^6$, Het$^7$, Het$^8$, Het$^9$, Het$^{10}$, Het$^{11}$, Het$^{12}$ and Het$^{13}$) group contains an unoxidised S-atom; and/or (b) n does not represent 0 when B represents —Z—S(O)$_n$—.

The compounds of the invention may exhibit tautomerism. All tautomeric forms and mixtures thereof are included within the scope of the invention.

The compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

Abbreviations are listed at the end of this specification.

Preferred values of each variable group are as follows. Such values may be used where appropriate with any of the values, definitions, claims, aspects or embodiments defined hereinbefore or hereinafter. In particular, each may be used as an individual limitation on the broadest definition of formula (I).

Preferred compounds of the invention include those in which:

$R^1$ represents $C_{1-8}$ alkyl (which alkyl group is optionally substituted by one or more groups selected from halo, aryl (which latter group is optionally substituted by one or more substituents selected from —OH, halo, cyano, nitro, $C_{1-4}$ alkyl, $C_{1-4}$ alkoxy (which latter two groups are optionally substituted by one or more halo atoms), —C(O)$R^{22c}$ and —S(O)$_2R^{21c}$), Het, N($R^{5a}$)$R^6$, —C(O)$R^{5b}$, —O$R^{5c}$, —C(O)N($R^{8a}$)$R^{5d}$, OC(O)N($R^{8b}$)$R^{5e}$, —S(O)$_2R^{9a}$, —S(O)$_2$N($R^{9b}$)$R^{9c}$ and —N(H)S(O)$_2R^{9d}$) or $R^1$ represents —C(O)O$R^7$, —C(O)N($R^{8a}$)$R^{5d}$ or —S(O)$_2R^{9a}$;

$R^{5a}$ represents H or $C_{1-5}$ alkyl;

$R^{5b}$ to $R^{5e}$ independently represent, at each occurrence when used herein, H, $C_{1-6}$ alkyl (which latter group is optionally substituted by one or more substituents selected from cyano, nitro and optionally substituted aryl), aryl (which latter group is optionally substituted by one or more substituents selected from —OH, halo, cyano, nitro, N($R^{22a}$)$R^{22b}$ (in which latter group $R^{22a}$ and $R^{22b}$ together represent $C_{3-6}$ alkylene), $C_{1-5}$ alkyl and $C_{1-5}$ alkoxy (which latter two groups are optionally substituted by one or more halo atoms)), Het$^3$, or $R^{5d}$, together with $R^{8a}$, represents $C_{4-5}$ alkylene (which alkylene group is optionally interrupted by an O atom);

$R^6$ represents H, $C_{1-6}$ alkyl, optionally substituted aryl —C(O)$R^{10a}$, —C(O)O$R^{10b}$ or —C(O)N(H)$R^{10c}$;

$R^{10a}$ and $R^{10b}$ independently represent $C_{1-5}$ alkyl (optionally substituted by one or more substituents selected from halo and optionally substituted aryl) or optionally substituted aryl;

$R^{10c}$ represents $C_{1-4}$ alkyl;

$R^7$ represents $C_{1-6}$ alkyl (optionally substituted by one or more substituents selected from halo, optionally substituted aryl, $C_{1-4}$ alkoxy and Het$^4$);

$R^{8a}$ and $R^{8b}$ independently represent H, $C_{1-6}$ alkyl (which latter group is optionally substituted by one or more substituents selected from halo, cyano and nitro), -D-(optionally substituted aryl), -D-(optionally substituted aryloxy), -D-Het$^5$, -D-N(H)C(O)$R^{11a}$, -D-C(O)$R^{11b}$, or $R^{8a}$, together with $R^{5d}$ represents $C_{4-5}$ alkylene (which alkylene group is optionally interrupted by an O atom);

$R^{11a}$ and $R^{11d}$ independently represent $C_{1-4}$ alkyl (optionally substituted by one or more substituents selected from halo, cyano, nitro and optionally substituted aryl) or optionally substituted aryl;

D represents, at each occurrence when used herein, a direct bond or $C_{1-4}$ alkylene;

$R^{9a}$ represents $C_{1-6}$ alkyl (optionally substituted by one or more halo groups) or optionally substituted aryl;

$R^{9b}$ represents H or $C_{1-3}$ alkyl;

$R^{9c}$ and $R^{9d}$ independently represent, at each occurrence when used herein, $C_{1-5}$ alkyl (optionally substituted by one or more substituents selected from halo, optionally substituted aryl and Het$^6$), optionally substituted aryl or Het$^7$, or $R^{9c}$ represents H;

$R^2$ represents H, halo, $C_{1-3}$ alkyl, —O$R^3$, —N(H)$R^{14}$ or, together with $R^3$, represents =O;

$R^3$ represents H, $C_{1-3}$ alkyl or, together with $R^2$, represents =O;

$R^{13}$ represents H, $C_{1-4}$ alkyl, -E-(optionally substituted aryl), or -E-Het$^8$;

$R^{14}$ represents H, $C_{1-6}$ alkyl, -E-(optionally substituted aryl), —C(O)$R^{16a}$, —C(O)O$R^{16b}$, S(O)$_2R^{16c}$, —C(O)N($R^{17a}$)$R^{17b}$ or —C(NH)NH$_2$;

$R^{16a}$ to $R^{16c}$ independently represent $C_{1-6}$ alkyl, or $R^{16a}$ represents H;

$R^{17a}$ and $R^{17b}$ independently represent H or $C_{1-4}$ alkyl;

E represents, at each occurrence when used herein, a direct bond or $C_{1-2}$ alkylene;

Het$^1$ and Het$^3$ to Het$^8$ independently represent four- to ten-membered heterocyclic groups containing one to four heteroatoms selected from oxygen, nitrogen and/or sulfur, which groups are optionally substituted by one or more substituents selected from —OH, oxo, halo, cyano, $C_{1-4}$ alkyl, $C_{1-4}$ alkoxy, phenyl, —N(H)$R^{18a}$, —C(O)$R^{18c}$, N(H)C(O)$R^{18h}$ and —N(H)S(O)$_2R^{18j}$;

$R^{18a}$, $R^{18c}$, $R^{18h}$ and $R^{18i}$ independently represent $C_{1-4}$ alkyl or optionally substituted aryl or $R^{18a}$, $R^{18c}$ and $R^{18h}$ independently represent H;

A represents $C_{1-4}$ alkylene optionally substituted by one or more substituents selected from OH and amino, —$C_{1-3}$ n-alkylene-S(O)$_2$N(H)— or —$C_{2-3}$ n-alkylene-N(H)S(O)$_2$— (in which latter two groups, alkylene is attached to the oxabispidine ring nitrogen);

B represents —Z—, —Z—N(H)—, —Z—C(O)N($R^{20b}$)—, —Z—N($R^{20c}$)S(O)$_2$—, —Z—S(O)$_2$N($R^{21d}$)—, —Z—S(O)$_2$—, —Z—O— (in which latter six groups, Z is attached to the carbon atom bearing $R^2$ and $R^3$);

Z represents a direct bond or $C_{1-4}$ alkylene;

$R^{20b}$ represents H, $C_{1-4}$ alkyl or, together with a single $R^4$ substituent at a position on the phenyl or pyridyl group that is ortho- to the position at which the group B is attached, $R^{20b}$ represents $C_{2-4}$ alkylene;

$R^{20c}$ and $R^{20d}$ independently represent H or $C_{1-3}$ alkyl;

when G represents N, G is in the ortho- or, in particular, the para-position relative to the point of attachment of B;

when G represents N, $R^4$ is absent (i.e. represents H) or represents a single cyano group;

$R^4$ represents one or more substituents selected from —OH, cyano, halo, nitro, $C_{1-6}$ alkyl, $C_{1-6}$ alkoxy, —C(O)N($R^{22e}$)$R^{22f}$, and N($R^{22m}$)S(O)$_2$—$C_{1-4}$ alkyl, or an $R^4$ substituent in a position on the phenyl or pyridyl group that is ortho- to the position at which the group B is attached may, together with $R^{20b}$, represent $C_{2-4}$ alkylene;

$R^{21c}$ represents $C_{1-4}$ alkyl;

$R^{22c}$, $R^{22e}$, $R^{22f}$ and $R^{22m}$ independently represent H or $C_{1-4}$ alkyl;

$R^{41}$ to $R^{46}$ independently represent H;

optional substituents on aryl and aryloxy groups are, unless otherwise stated, one or more substituents selected from halo, cyano, nitro, $C_{1-4}$ alkyl, $C_{1-4}$ alkoxy (which latter two groups are optionally substituted by one or more halo atoms), —N(H)S(O)$_2R^{21b}$ and —S(O)$_2$N(H)$R^{22o}$.

More preferred compounds of the invention include those in which:

$R^1$ represents straight- or branched-chain or part cyclic/acyclic $C_{1-6}$ alkyl, which alkyl group is optionally interrupted by oxygen and/or substituted by: (i) one or more halo or $OR^{5c}$ groups; and/or (ii) one group selected phenyl (which latter group is optionally substituted by one or more (e.g. one to three) substituents selected from halo, cyano, $C_{1-3}$ alkyl, $C_{1-3}$ alkoxy (which latter two groups are optionally substituted by one or more halo (e.g. fluoro) atoms), —C(O)—$C_{1-3}$ alkyl and —S(O)$_2$—$C_{1-4}$ alkyl), Het$^1$, —C(O)R$^{5b}$, —N(H)R$^6$, —C(O)N(R$^{8a}$)R$^{5d}$, —OC(O)N(H)R$^{8b}$, —S(O)$_2$—$C_{1-4}$ alkyl, —S(O)$_2$N(H)R$^{9c}$ and —N(H)S(O)$_2$R$^{9d}$ or $R^1$ represents —C(O)OR$^7$, —C(O)N(R$^{8a}$)R$^{5d}$ or —S(O)$_2$—$C_{1-5}$ alkyl;

Het$^1$ represents a four- (e.g. five-) to ten-membered heterocyclic group containing one to three heteroatoms selected from oxygen, nitrogen and/or sulfur, which group is optionally substituted by one or more (e.g. one to three) substituents selected from halo, $C_{1-3}$ alkyl, $C_{1-3}$ alkoxy and —C(O)—$C_{1-4}$ alkyl;

$R^{5b}$, $R^{5c}$ and $R^{5d}$ independently represent H, $C_{1-5}$ alkyl, phenyl (which latter group is optionally substituted by one or more substituents selected from —OH, halo, cyano, pyrrolidin-1-yl, $C_{1-4}$ alkyl and $C_{1-5}$ alkoxy (which latter group is optionally substituted by one or more halo (e.g. fluoro) atoms)) or Het$^3$;

Het$^3$ represents a five- to ten-membered heterocyclic group containing one or two heteroatoms selected from oxygen and nitrogen, which group is optionally substituted by one or more substituents selected from oxo, $C_{1-2}$ alkyl and —C(O)—$C_{1-4}$ alkyl;

$R^6$ represents H, $C_{1-4}$ alkyl, phenyl (which latter group is optionally substituted by one or more cyano groups) or —C(O)O—$C_{1-5}$ alkyl;

$R^7$ represents $C_{1-5}$ alkyl optionally substituted by Het$^4$;

Het$^4$ represents a five- to ten-membered heterocyclic group containing one or two heteroatoms selected from oxygen and nitrogen, which group is optionally substituted by one or more substituents selected from $C_{1-2}$ alkyl and —C(O)—$C_{1-4}$ alkyl;

$R^{8a}$ and $R^{8b}$ independently represent H, $C_{1-5}$ alkyl or -D-(phenyl), the phenyl part of which latter group is optionally substituted by one or more (e.g. one to three) substituents selected from halo, $C_{1-3}$ alkyl and $C_{1-3}$ alkoxy;

D represents $C_{1-3}$ alkylene (e.g. CH$_2$ or C(CH$_3$)$_2$);

$R^{9c}$ and $R^{9d}$ independently represent $C_{1-4}$ alkyl (optionally substituted by one or more substituents selected from halo, phenyl (which latter group is optionally substituted by one or more substituents selected from halo, $C_{1-2}$ alkyl and $C_{1-2}$ alkoxy (which latter two groups are optionally substituted by one or more halo (e.g. fluoro) atoms)) and Het$^6$), phenyl (which latter group is optionally substituted by one or more substituents selected from halo, $C_{1-3}$ alkyl and $C_{1-3}$ alkoxy (which latter two groups are optionally substituted by one or more halo (e.g. fluoro) atoms)) or Het$^7$;

Het$^6$ and Het$^7$ independently represent four- (e.g. five-) to ten-membered heterocyclic groups containing one to three heteroatoms selected from oxygen, nitrogen and/or sulfur, which groups are optionally substituted by one or more (e.g. one to three) substituents selected from halo, $C_{1-3}$ alkyl and $C_{1-3}$ alkoxy;

$R^2$ represents H, —OR$^{13}$ or —N(H)R$^{14}$;

$R^3$ represents H;

$R^{13}$ represents H or phenyl (which latter group is optionally substituted by one or more substituents selected from cyano and $C_{1-2}$ alkoxy);

$R^{14}$ represents H phenyl (which latter group is optionally substituted by one or more cyano groups) or —C(O)O—$C_{1-5}$ alkyl;

A represents $C_{1-3}$ n-alkylene;

B represents —Z—, —N(H)S(O)$_2$—, —S(O)$_2$N(H)—, —Z—N(H)—, —Z—C(O)N(R$^{20b}$)—, —Z—S(O)$_2$—, —Z—O— (in which latter four groups, Z is attached to the carbon atom bearing $R^2$ and $R^3$);

Z represents a direct bond or $C_{1-3}$ alkylene;

$R^{20b}$, together with a single $R^4$ substituent at a position on the phenyl or pyridyl group that is ortho- to the position at which the group B is attached, represents $C_{2-3}$ alkylene;

G represents CH;

$R^4$ represents one or two cyano or halo (e.g. fluoro) groups in the ortho- and/or, particularly, the para-position relative to the point of attachment of the group B, or alternatively, when B represents —Z—C(O)N(R$^{20b}$)—,
(i) an $R^4$ substituent in a position on the phenyl or pyridyl group that is ortho- to the position at which the group B is attached may, together with R$^{20b}$, represent $C_{2-3}$ alkylene, and
(ii) $R^4$ may further represent a nitro group in the para-position relative to the point of attachment of the group B.

Particularly preferred compounds of the invention include those in which:

$R^1$ represents straight- or branched-chain or part cyclic/acyclic $C_{1-6}$ alkyl, which alkyl group is optionally interrupted by oxygen and/or substituted by: (i) one or more halo or $OR^{5c}$ groups; and/or (ii) one group selected phenyl (which latter group is optionally substituted by one or more (e.g. one to three) substituents selected from halo, cyano, $C_{1-2}$ alkyl, $C_{1-2}$ alkoxy (which latter two groups are optionally substituted by one or more halo (e.g. fluoro) atoms), —C(O)—$C_{1-2}$ alkyl and —S(O)$_2$—$C_{1-2}$ alkyl), Het$^1$, —C(O)R$^{5b}$, —N(H)R$^6$, —C(O)N(H)R$^{8a}$, —OC(O)N(H)—$C_{1-4}$ alkyl, —S(O)$_2$—$C_{1-4}$ alkyl, —S(O)$_2$N(H)—$C_{1-4}$ alkyl and —N(H)S(O)$_2$R$^{9d}$;

Het$^1$ represents a five- or six-membered heterocyclic group containing one or two heteroatoms selected from oxygen, nitrogen and/or sulfur, which group is optionally substituted by one or more (e.g. one or two) substituents selected from halo (e.g. chloro), $C_{1-2}$ alkyl and $C_{1-2}$ alkoxy;

$R^{5b}$ and $R^{5c}$ independently represent phenyl optionally substituted by one to three substituents selected from halo, cyano, $C_{1-2}$ alkyl and $C_{1-2}$ alkoxy;

$R^6$ represents H, $C_{1-4}$ alkyl or —C(O)O—$C_{1-5}$ alkyl;

$R^{8a}$ represents $C_{1-4}$ alkyl (e.g. tert-butyl) or -D-(phenyl);

$R^{9d}$ represents $C_{1-4}$ alkyl (optionally substituted by one or more substituents selected from halo and phenyl (which latter group is optionally substituted by one or more substituents selected from halo (e.g. chloro), $C_{1-2}$ alkyl and $C_{1-2}$ alkoxy (which latter two groups are optionally substituted by one or more halo (e.g. fluoro) atoms))), phenyl (which latter group is optionally substituted by one or more substituents selected from halo (e.g. fluoro), $C_{1-2}$ alkyl and $C_{1-2}$ alkoxy (which latter two groups are optionally substituted by one or more halo (e.g. fluoto) atoms)) or Het$^7$;

Het$^7$ represents a five- or six-membered heterocyclic group containing one nitrogen atom and optionally containing one or two further heteroatoms selected from oxygen, nitrogen and/or sulfur, which heterocyclic group is optionally substituted by one to three substituents selected from halo and $C_{1-2}$ alkyl;

A represents —(CH$_2$)$_{1-2}$—;

B represents —Z—, —N(H)S(O)$_2$— (in which latter group, —N(H) is attached to the carbon atom bearing $R^2$ and $R^3$), —C(O)N(R$^{20b}$)— (in which latter group, —C(O) is attached to the carbon atom bearing R$^2$ and R$^3$) or —Z—O— (in which latter group, Z is attached to the carbon atom bearing R$^2$ and R$^3$);

Z represents a direct bond or —(CH$_2$)$_{1-2}$—;

R$^{20b}$, together with a single R$^4$ substituent at a position on the phenyl or pyridyl group that is ortho- to the position at which the group B is attached, represents —(CH$_2$)$_{2-3}$—;

R$^4$ represents a cyano or fluoro group in the para-position relative to the point of attachment of the group B, and, when B represents —C(O)N(R$^{20b}$)—, R$^4$ may also, together with R$^{20b}$, represent —(CH$_2$)$_{2-3}$—.

Especially preferred compounds of the invention include those in which:

R$^1$ represents straight- or branched-chain C$_{1-3}$ alkyl substituted by OR$^{5c}$, phenyl (which latter group is optionally substituted by one or two substituents selected from halo (e.g. fluoro or chloro), cyano, methyl, methoxy (which latter two groups are optionally substituted by one to three fluoro atoms), —C(O)CH$_3$ and —S(O)$_2$CH$_3$), Het$^1$, —C(O)R$^{5b}$, —N(H)C(O)O—C$_{3-4}$ alkyl, —C(O)N(H)R$^{8a}$, —OC(O)N(H)—C$_{3-4}$ alkyl, —S(O)$_2$N(H)—C$_{3-4}$ alkyl or —N(H)S(O)$_2$R$^{9d}$;

Het$^1$ represents an aromatic five- or six-membered heterocyclic group containing one or two heteroatoms selected from oxygen, nitrogen and/or sulfur, which group is optionally substituted by one or two substituents selected from chloro, methyl and methoxy;

R$^{5b}$ and R$^{5c}$ independently represent phenyl optionally substituted by one or two substituents selected from cyano, methyl and methoxy;

R$^{8a}$ represents tert-butyl, CH$_2$-phenyl or C(CH$_3$)$_2$-phenyl;

R$^{9d}$ represents C$_{1-4}$ alkyl (which latter group is optionally substituted by one or more fluoro atoms), (CH$_2$)$_{1-2}$-phenyl (the phenyl part of which latter group is optionally substituted by one to three substituents selected from chloro, methyl and methoxy (which latter two groups are optionally substituted by one or more fluoro atoms)), phenyl (optionally substituted by one or more substituents selected from fluoro, methyl and methoxy (which latter two groups are optionally substituted by one or more fluoro atoms)) or Het$^7$;

Het$^7$ represents a five-membered heterocyclic group containing one nitrogen atom and optionally containing one further heteroatom selected from oxygen, nitrogen and sulfur, which heterocyclic group is optionally substituted by one to three methyl groups;

R$^2$ represents H or —OH;

A represents —CH$_2$—;

B represents —CH$_2$—, —N(H)S(O)$_2$— (in which latter group, —N(H) is attached to the carbon atom bearing R$^2$ and R$^3$) or —(CH$_2$)$_{0-1}$—O— (in which latter group, —CH$_2$— is attached to the carbon atom bearing R$^2$ and R$^3$).

Compounds of formula I that are more preferred still include those in which:

R$^1$ represents (i) C$_{1-3}$ n-alkyl substituted by phenyl (which latter group is optionally substituted by one to three substituents selected from methyl and methoxy (which latter two groups are optionally substituted by one to three (e.g. by two) fluoro atoms)) or phenoxy (the phenyl part of which latter group is optionally substituted by cyano), (ii) —N(H)C(O)O-tert-butyl, (iii) —S(O)$_2$N(H)-tert-butyl or (iv) —N(H)S(O)$_2$R$^{9d}$;

R$^{9d}$ represents (a) methyl (optionally substituted by one to three fluoro atoms), (b) isopropyl, (c) n-butyl, (d) -(CH$_2$)-phenyl (the phenyl part of which latter group is optionally substituted by one or two substituents selected from chloro, methyl and trifluoromethyl), (e) phenyl (which latter group is optionally substituted by one or two substituents selected from fluoro, methoxy and trifluoromethoxy) or (f) imidazolyl (e.g. imidazol-4-yl) or isoxazolyl (e.g. isoxazol-4-yl), which latter two groups are optionally substituted by one or two methyl groups.

Particular values of each variable group are as follows. Such values may be used where appropriate with any of the values, definitions, claims, aspects or embodiments defined hereinbefore or hereinafter. In particular, each may be used as an individual limitation on the broadest definition of formula (I).

R$^1$ represents C$_{2-3}$ alkyl, which alkyl group is substituted by at least one —S(O)$_2$N(R$^{9b}$)R$^{9c}$ and/or —N(R$^{9b}$)S(O)$_2$R$^{9d}$ group;

R$^{9b}$, represents H or C$_{1-3}$ alkyl;

R$^{9c}$ and R$^{9d}$ each independently represent hydrogen, C$_{1-6}$ alkyl (optionally substituted by one or more halo groups), aryl (optionally substituted by one or more halo, cyano, methoxy, fluoromethoxy, difluoromethoxy or trifluoromethoxy groups) or Het (such as imidazolyl or isoxazolyl);

R$^2$ and R$^3$ each independently represent hydrogen, or hydroxy;

A represents a direct bond or C$_{1-3}$ alkylene;

B represents a direct bond, C$_{1-3}$ alkylene or C$_{1-3}$ alkoxy (in which the oxygen is attached to the phenyl group that is optionally substituted with R$^4$);

G represents carbon;

R$^{41}$ to R$^{46}$ represents hydrogen; and

R$^4$ represents one or more optional substituents selected from cyano and/or halo (such as fluoro) and an R$^4$ substituent is in a position on the phenyl group that is ortho- and/or para- to the position at which the group B is attached.

Particular compounds of the invention include, for example, compounds of the Formula I, or pharmaceutically-acceptable salts thereof, wherein, unless otherwise stated, each of each variable group has any of the meanings defined hereinbefore or in paragraphs (a) to (d) hereinafter:—

(a) R$^1$ represents a C$_2$-C$_5$ alkyl group, (such as ethyl, propyl, butyl, propyl or pentyl), which is optionally substituted by one or more sulfonamide groups selected from 4-cyanobenzenesulfonamide, propane-2-sulfonamide, 1-phenylmethanesulfonamide, propane-1-sulfonamide, 4-fluorobenzenesulfonamide; benzenesulfonamide, 2,4-difluorobenzenesulfonamide, methanesulfonamide, 3-chloro-1-phenylmethanesulphonamide, trifluoromethanesulfonamide, 1-methyl-1H-imidazole-4-sulfonamide, butane-1-sulfonamide, 1-[4-(trifluoromethyl)phenyl]methanesulfonamide, 3,5-dimethylisoxazole-4-sulfonamide, 2-(trifluoromethoxy)benzenesulfonamide, [2-(trifluoromethoxy)phenyl]methanesulfonamide, 2,3-dihydro-1-benzofuran-5-sulfonamide, 2-cyanobenzenesulfonamide, 4-methoxybenzenesulfonamide, 5-chloro-1,3-dimethyl-1H-pyrazole-4-sulfonamide, 3-fluorobenzenesulphonamide, 5-methylisoxazole-4-sulfonamide, 3-cyanobenzenesulfonamide, 4-cyano-1-phenylmethanesulphonamide, or 2-fluorobenzenesulphonamide;

(b) R$^{41}$ to R$^{46}$ are hydrogen;

(c) the group

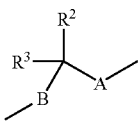

represents methylene, ethylene, propylene, butylene, or 2-hydroxypropylene, optionally terminated or interrupted with an oxygen atom and/or optionally interrupted with a —SO$_2$—NH— or —NH—SO$_2$— group;

(d) the group

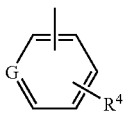

represents phenyl, 4-cyanophenyl, 3,4-bis(difluoromethoxy)phenyl, 4-fluorophenyl, 4-(difluoromethoxy)-phenyl, 2-fluorophenyl, 2,5-difluorophenyl, 3,4-difluorophenyl, 4-cyano-2-fluorophenyl, 3,4-difluorophenyl, 2-cyanophenyl, 3-fluorophenyl, 4-cyano-2,6-difluorophenyl, 2,6-difluorophenyl, 3-cyanophenyl, 4-chlorophenyl, 4-(trifluoromethyl)phenyl, 2,4-difluorophenyl, 2-(trifluoromethoxy)phenyl, 3-chlorophenyl, or 4-methoxyphenyl.

Preferred compounds of the invention include the compounds of the Examples disclosed hereinafter. In this respect, preferred compounds of the invention that might be mentioned include:

(i) N-(2-{7-[(2S)-3-(4-cyanophenoxy)-2-hydroxypropyl]-9-oxa-3,7-diazabicyclo[3.3.1]non-3-yl}ethyl)propane-2-sulfonamide;
(ii) N-(2-{7-[(2S)-3-(4-cyanophenoxy)-2-hydroxypropyl]-9-oxa-3,7-diazabicyclo[3.3.1]non-3-yl}ethyl)-1-phenylmethanesulfonamide;
(iii) N-(tert-butyl)-3-{7-[3-(4-cyanophenoxy)propyl]-9-oxa-3,7-diazabicyclo[3.3.1]non-3-yl}propane-1-sulfonamide;
(iv) tert-butyl {2-[7-(2-{[(4-fluorophenyl)sulfonyl]amino}ethyl)-9-oxa-3,7-diazabicyclo[3.3.1]non-3-yl]ethyl}carbamate;
(v) N-[2-(7-benzyl-9-oxa-3,7-diazabicyclo[3.3.1]non-3-yl)ethyl]-4-fluorobenzenesulfonamide;
(vi) N-(2-{7-[3-(4-cyanophenoxy)propyl]-9-oxa-3,7-diazabicyclo-[3.3.1]non-3-yl}ethyl)-1-phenylmethanesulfonamide;
(vii) N-(2-{7-[3-(4-cyanophenoxy)propyl]-9-oxa-3,7-diazabicyclo-[3.3.1]non-3-yl}ethyl)propane-2-sulfonamide;
(viii) N-[2-(7-benzyl-9-oxa-3,7-diazabicyclo[3.3.1]non-3-yl)ethyl]-4-cyanobenzenesulfonamide;
(ix) N-[2-(7-{2-[3,4-bis(difluoromethoxy)phenyl]ethyl}-9-oxa-3,7-diazabicyclo[3.3.1]non-3-yl)ethyl]-4-cyanobenzenesulfonamide;
(x) N-(2-{7-[3-(4-cyanophenoxy)propyl]-9-oxa-3,7-diazabicyclo-[3.3.1]non-3-yl}ethyl)benzenesulfonamide;
(xi) N-(2-{7-[3-(4-cyanophenoxy)propyl]-9-oxa-3,7-diazabicyclo-[3.3.1]non-3-yl}ethyl)-2,4-difluorobenzenesulfonamide;
(xii) N-(2-{7-[2-(4-cyanophenoxy)ethyl]-9-oxa-3,7-diazabicyclo-[3.3.1]non-3-yl}ethyl)-4-fluorobenzenesulfonamide;
(xiii) N-(2-{7-[2-(4-cyanophenoxy)ethyl]-9-oxa-3,7-diazabicyclo-[3.3.1]non-3-yl}ethyl)methanesulfonamide;
(xiv) N-(2-{7-[3-(4-cyanophenoxy)propyl]-9-oxa-3,7-diazabicyclo-[3.3.1]non-3-yl}ethyl)-4-fluorobenzenesulfonamide;
(xv) N-(2-{7-[3-(4-cyanophenoxy)propyl]-9-oxa-3,7-diazabicyclo-[3.3.1]non-3-yl}ethyl)methanesulfonamide;
(xvi) 4-cyano-N-(2-{7-[2-(4-cyanophenoxy)ethyl]-9-oxa-3,7-diazabicyclo[3.3.1]non-3-yl}ethyl)benzenesulfonamide;
(xvii) 1-(3-chlorophenyl)-N-(2-{7-[2-(4-cyanophenoxy)ethyl]-9-oxa-3,7-diazabicyclo[3.3.1]non-3-yl}ethyl)methanesulfonamide;
(xviii) 4-cyano-N-(2-{7-[3-(4-cyanophenoxy)propyl]-9-oxa-3,7-diazabicyclo-[3.3.1]non-3-yl}ethyl)benzenesulfonamide;
(xix) N-(2-{7-[3-(4-cyanophenoxy)propyl]-9-oxa-3,7-diazabicyclo-[3.3.1]non-3-yl}ethyl)-1,1,1-trifluoromethanesulfonamide;
(xx) N-(2-{7-[2-(4-cyanophenoxy)ethyl]-9-oxa-3,7-diazabicyclo-[3.3.1]non-3-yl}ethyl)-1-phenylmethanesulfonamide;
(xxi) N-(2-{7-[2-(4-cyanophenoxy)ethyl]-9-oxa-3,7-diazabicyclo-[3.3.1]non-3-yl}ethyl)-1-methyl-1H-imidazole-4-sulfonamide;
(xxii) N-(2-{7-[3-(4-cyanophenoxy)propyl]-9-oxa-3,7-diazabicyclo-[3.3.1]non-3-yl}ethyl)butane-1-sulfonamide;
(xxiii) N-(2-{7-[3-(4-cyanophenoxy)propyl]-9-oxa-3,7-diazabicyclo-[3.3.1]non-3-yl}ethyl)-1-methyl-1H-imidazole-4-sulfonamide;
(xxiv) N-(2-{7-[2-(4-cyanophenoxy)ethyl]-9-oxa-3,7-diazabicyclo-[3.3.1]non-3-yl}ethyl)-1-[4-(trifluoromethyl)phenyl]methanesulfonamide;
(xxv) N-(2-{7-[2-(4-cyanophenoxy)ethyl]-9-oxa-3,7-diazabicyclo-[3.3.1]non-3-yl}ethyl)-3,5-dimethylisoxazole-4-sulfonamide;
(xxvi) N-(2-{7-[3-(4-cyanophenoxy)propyl]-9-oxa-3,7-diazabicyclo-[3.3.1]non-3-yl}ethyl)-1-[4-(trifluoromethyl)phenyl]methanesulfonamide;
(xxvii) N-(2-{7-[3-(4-cyanophenoxy)propyl]-9-oxa-3,7-diazabicyclo-[3.3.1]non-3-yl}ethyl)-3,5-dimethylisoxazole-4-sulfonamide;
(xxviii) N-(2-{7-[3-(4-cyanophenoxy)propyl]-9-oxa-3,7-diazabicyclo-[3.3.1]non-3-yl}ethyl)-2-(trifluoromethoxy)benzenesulfonamide;
(xxix) 1-(3-chlorophenyl)-N-(2-{7-[3-(4-cyanophenoxy)propyl]-9-oxa-3,7-diazabicyclo[3.3.1]non-3-yl}ethyl)methanesulfonamide;
(xxx) N-(2-{7-[2-(4-cyanophenoxy)ethyl]-9-oxa-3,7-diazabicyclo-[3.3.1]non-3-yl}ethyl)benzenesulfonamide;
(xxxi) 4-cyano-N-{2-[7-(4-cyanobenzyl)-9-oxa-3,7-diazabicyclo-[3.3.1]non-3-yl]ethyl}benzenesulfonamide;
(xxxii) 4-cyano-N-{2-[7-(4-fluorobenzyl)-9-oxa-3,7-diazabicyclo-[3.3.1]non-3-yl]ethyl}benzenesulfonamide;
(xxxiii) 4-cyano-N-(2-{7-[4-(difluoromethoxy)benzyl]-9-oxa-3,7-diazabicyclo[3.3.1]non-3-yl}ethyl)benzenesulfonamide;
(xxxiv) 4-cyano-N-(2-{7-[2-(4-fluorophenyl)ethyl]-9-oxa-3,7-diazabicyclo[3.3.1]non-3-yl}ethyl)benzenesulfonamide;
(xxxv) 4-cyano-N-(2-{7-[2-(4-fluorophenoxy)ethyl]-9-oxa-3,7-diazabicyclo[3.3.1]non-3-yl}ethyl)benzenesulfonamide;
(xxxvi) 4-cyano-N-(2-{7-[3-(4-fluorophenoxy)propyl]-9-oxa-3,7-diazabicyclo[3.3.1]non-3-yl}ethyl)benzenesulfonamide;

(xxxvii) N-(2-{7-[2-(4-cyanophenoxy)ethyl]-9-oxa-3,7-diazabicyclo-[3.3.1]non-3-yl}ethyl)-2,3-dihydro-1-benzofuran-5-sulfonamide;
(xxxviii) 5-chloro-N-(2-{7-[2-(4-cyanophenoxy)ethyl]-9-oxa-3,7-diaza-bicyclo[3.3.1]non-3-yl}ethyl)-1,3-dimethyl-1H-pyrazole-4-sulfonamide;
(xxxix) 2-cyano-N-(2-{7-[2-(4-cyanophenoxy)ethyl]-9-oxa-3,7-diazabicyclo[3.3.1]non-3-yl}ethyl)benzenesulfonamide;
(xl) N-(2-{7-[2-(4-cyanophenoxy)ethyl]-9-oxa-3,7-diazabicyclo-[3.3.1]non-3-yl}ethyl)-4-methoxybenzenesulfonamide;
(xli) N-(2-{7-[3-(4-cyanophenoxy)propyl]-9-oxa-3,7-diazabicyclo-[3.3.1]non-3-yl}ethyl)-2,3-dihydro-1-benzofuran-5-sulfonamide;
(xlii) 5-chloro-N-(2-{7-[3-(4-cyanophenoxy)propyl]-9-oxa-3,7-diaza-bicyclo [3.3.1]non-3-yl}ethyl)-1,3-dimethyl-1H-pyrazole-4-sulfonamide;
(xliii) N-(2-{7-[3-(4-cyanophenoxy)propyl]-9-oxa-3,7-diazabicyclo-[3.3.1]non-3-yl}ethyl)-4-methoxybenzenesulfonamide;
(xliv) 4-cyano-N-(2-{7-[3-(2-fluorophenoxy)propyl]-9-oxa-3,7-diazabicyclo[3.3.1]non-3-yl}ethyl)benzenesulfonamide;
(xlv) 4-cyano-N-(2-{7-[3-(2,5-difluorophenoxy)propyl]-9-oxa-3,7-diazabicyclo[3.3.1]non-3-yl}ethyl)benzenesulfonamide;
(xlvi) 4-cyano-N-(2-{7-[3-(3,4-difluorophenoxy)propyl]-9-oxa-3,7-diazabicyclo[3.3.1]non-3-yl}ethyl)benzenesulfonamide;
(xlvii) 4-cyano-N-(2-{7-[2-(2-fluorophenoxy)ethyl]-9-oxa-3,7-diazabicyclo[3.3.1]non-3-yl}ethyl)benzenesulfonamide;
(xlviii) 4-cyano-N-(2-{7-[2-(4-cyano-2-fluorophenoxy)ethyl]-9-oxa-3,7-diazabicyclo[3.3.1]non-3-yl}ethyl)benzenesulfonamide;
(xlix) 4-cyano-N-[2-(7-{2-[(4-fluorobenzyl)oxy]ethyl}-9-oxa-3,7-diazabicyclo[3.3.1]non-3-yl)ethyl]benzenesulfonainide;
(l) 4-cyano-N-(2-{7-[2-(3,4-difluorophenyl)ethyl]-9-oxa-3,7-diazabicyclo[3.3.1]non-3-yl}ethyl)benzenesulfonamide;
(li) 4-cyano-N-(2-{7-[2-(3,5-dimethyl-1H-pyrazol-1-yl)ethyl]-9-oxa-3,7-diazabicyclo[3.3.1]non-3-yl}ethyl)benzenesulfonamide;
(lii) 4-cyano-N-{2-[7-(2-cyanobenzyl)-9-oxa-3,7-diazabicyclo-[3.3.1]non-3-yl]ethyl}benzenesulfonamide;
(liii) 4-cyano-N-(2-{7-[(3,5-dimethylisoxazol-4-yl)methyl]-9-oxa-3,7-diazabicyclo[3.3.1]non-3-yl}ethyl)benzenesulfonamide;
(liv) N-(2-{7-[2-(4-cyanophenoxy)ethyl]-9-oxa-3,7-diazabicyclo-[3.3.1]non-3-yl}ethyl)-3-fluorobenzenesulfonamide;
(lv) N-(2-{7-[3-(4-cyanophenoxy)propyl]-9-oxa-3,7-diazabicyclo-[3.3.1]non-3-yl}ethyl)-3-fluorobenzenesulfonamide;
(lvi) N-(2-{7-[3-(4-cyanophenoxy)propyl]-9-oxa-3,7-diazabicyclo-[3.3.1]non-3-yl}ethyl)-5-methylisoxazole-4-sulfonamide;
(lvii) N-{2-[7-(1-benzofuran-3-ylmethyl)-9-oxa-3,7-diazabicyclo-[3.3.1]non-3-yl]ethyl}-4-cyanobenzenesulfonamide;
(lviii) 4-cyano-N-{2-[7-(1H-indol-3-ylmethyl)-9-oxa-3,7-diazabicyclo-[3.3.1]non-3-yl]ethyl}benzenesulfonamide;
(lix) 4-cyano-N-(2-{7-[(1-methyl-1H-indol-3-yl)methyl]-9-oxa-3,7-diazabicyclo[3.3.1]non-3-yl}ethyl)benzenesulfonamide;
(lx) 4-cyano-N-(2-{7-[(5-fluoro-1H-indol-3-yl)methyl]-9-oxa-3,7-diazabicyclo[3.3.1]non-3-yl}ethyl)benzenesulfonamide;
(lxi) N-(3-{7-[2-(4-cyanophenoxy)ethyl]-9-oxa-3,7-diazabicyclo-[3.3.1]non-3-yl}propyl)-4-fluorobenzenesulfonamide;
(lxii) N-(3-{7-[2-(4-cyanophenoxy)ethyl]-9-oxa-3,7-diazabicyclo-[3.3.1]non-3-yl}propyl)-2,4-difluorobenzenesulfonamide;
(lxiii) N-(3-{7-[3-(4-cyanophenoxy)propyl]-9-oxa-3,7-diazabicyclo-[3.3.1]non-3-yl}propyl)benzenesulfonamide;
(lxiv) N-{2-[7-(4-cyanobenzyl)-9-oxa-3,7-diazabicyclo [3.3.1]non-3-yl]ethyl}-1-phenylmethanesulfonamide;
(lxv) N-(3-{7-[2-(4-cyanophenoxy)ethyl]-9-oxa-3,7-diazabicyclo-[3.3.1]non-3-yl}propyl)-1-phenylmethanesulfonamide;
(lxvi) N-(3-{7-[2-(4-cyanophenoxy)ethyl]-9-oxa-3,7-diazabicyclo-[3.3.1]non-3-yl}propyl)benzenesulfonamide;
(lxvii) 4-cyano-N-(2-{7-[(2-methyl-1H-indol-3-yl)methyl]-9-oxa-3,7-diazabicyclo[3.3.1]non-3-yl}ethyl)benzenesulfonamide;
(lxviii) 4-cyano-N-(2-{7-[2-(3-fluorophenyl)ethyl]-9-oxa-3,7-diazabicyclo-[3.3.1]non-3-yl}ethyl)benzenesulfonamide;
(lxix) 4-cyano-N-(2-{7-[3-(3-fluorophenoxy)propyl]-9-oxa-3,7-diazabicyclo[3.3.1]non-3-yl}ethyl)benzenesulfonamide;
(lxx) 4-cyano-N-(2-{7-[3-(4-cyano-2-fluorophenoxy)propyl]-9-oxa-3,7-diazabicyclo[3.3.1]non-3-yl}ethyl)benzenesulfonamide;
(lxxi) 4-cyano-N-(2-{7-[3-(4-cyano-2,6-difluorophenoxy)propyl]-9-oxa-3,7-diazabicyclo[3.3.1]non-3-yl}ethyl)benzenesulfonamide;
(lxxii) 4-cyano-N-(2-{7-[2-(2,6-difluorophenoxy)ethyl]-9-oxa-3,7-diazabicyclo[3.3.1]non-3-yl}ethyl)benzenesulfonamide;
(lxxiii) N-(3-{7-[3-(4-cyanophenoxy)propyl]-9-oxa-3,7-diazabicyclo-[3.3.1]non-3-yl}propyl)propane-2-sulfonamide;
(lxxiv) N-(3-{7-[3-(4-cyanophenoxy)propyl]-9-oxa-3,7-diazabicyclo-[3.3.1]non-3-yl}propyl)-1-phenylmethanesulfonamide;
(lxxv) N-(3-{7-[3-(4-cyanophenoxy)propyl]-9-oxa-3,7-diazabicyclo-[3.3.1]non-3-yl}propyl)-3,5-dimethylisoxazole-4-sulfonamide;
(lxxvi) N-(3-{7-[2-(4-cyanophenoxy)ethyl]-9-oxa-3,7-diazabicyclo-[3.3.1]non-3-yl}propyl)-3,5-dimethylisoxazole-4-sulfonamide;
(lxxvii) N-{3-[7-(4-cyanobenzyl)-9-oxa-3,7-diazabicyclo [3.3.1]non-3-yl]propyl}-3,5-dimethylisoxazole-4-sulfonamide;
(lxxviii) N-{2-[7-(4-cyanobenzyl)-9-oxa-3,7-diazabicyclo [3.3.1]non-3-yl]ethyl}-3,5-dimethylisoxazole-4-sulfonamide;
(lxxix) N-{2-[7-(1,3-benzoxazol-2-ylmethyl)-9-oxa-3,7-diazabicyclo-[3.3.1]non-3-yl]ethyl}-4-cyanobenzenesulfonamide;
(lxxx) 3-cyano-N-(2-{7-[3-(4-cyanophenoxy)propyl]-9-oxa-3,7-diazabicyclo[3.3.1]non-3-yl}ethyl)benzenesulfonamide;
(lxxxi) 3-cyano-N-(2-{7-[2-(4-cyanophenoxy)ethyl]-9-oxa-3,7-diazabicyclo[3.3.1]non-3-yl}ethyl)benzenesulfonamide;
(lxxxii) 3-cyano-N-{2-[7-(4-cyanobenzyl)-9-oxa-3,7-diazabicyclo-[3.3.1]non-3-yl]ethyl}benzenesulfonamide;
(lxxxiii) 2-cyano-N-{2-[7-(4-cyanobenzyl)-9-oxa-3,7-diazabicyclo-[3.3.1]non-3-yl]ethyl}benzenesulfonamide;

(lxxxiv) 2-cyano-N-(2-{7-[3-(4-cyanophenoxy)propyl]-9-oxa-3,7-diazabicyclo[3.3.1]non-3-yl}ethyl)benzenesulfonamide;

(lxxxv) N-(4-cyanobenzyl)-2-[7-(4-cyanobenzyl)-9-oxa-3,7-diazabicyclo-[3.3.1]non-3-yl]ethanesulfonamide;

(lxxxvi) N-(4-cyanobenzyl)-2-[7-(2-cyanobenzyl)-9-oxa-3,7-diazabicyclo-[3.3.1]non-3-yl]ethanesulfonamide;

(lxxxvii) N-(4-cyanobenzyl)-N-[(3,5-dimethylisoxazol-4-yl)methyl]-2-{7-[(3,5-dimethylisoxazol-4-yl)methyl]-9-oxa-3,7-diazabicyclo-[3.3.1]non-3-yl}ethanesulfonamide;

(lxxxviii) 4-cyano-N-(3-{7-[2-(4-cyano-2-fluorophenoxy)ethyl]-9-oxa-3,7-diazabicyclo[3.3.1]non-3-yl}propyl)benzenesulfonamide;

(lxxxix) N-(3-{7-[2-(4-cyano-2-fluorophenoxy)ethyl]-9-oxa-3,7-diazabicyclo[3.3.1]non-3-yl}propyl)-4-fluorobenzenesulfonamide;

(xc) N-(3-{7-[2-(4-cyanophenoxy)ethyl]-9-oxa-3,7-diazabicyclo-[3.3.1]non-3-yl}propyl)-2-fluorobenzenesulfonamide;

(xci) N-(2-{7-[2-(4-cyanophenoxy)ethyl]-9-oxa-3,7-diazabicyclo-[3.3.1]non-3-yl}ethyl)-2-fluorobenzenesulfonamide;

(xcii) N-(3-{7-[2-(4-cyano-2-fluorophenoxy)ethyl]-9-oxa-3,7-diazabicyclo[3.3.1]non-3-yl}propyl)-2,4-difluorobenzene-sulfonamide;

(xciii) N-(3-{7-[2-(4-cyano-2-fluorophenoxy)ethyl]-9-oxa-3,7-diazabicyclo[3.3.1]non-3-yl}propyl)benzenesulfonamide;

(xciv) N-(2-{7-[2-(4-cyano-2-fluorophenoxy)ethyl]-9-oxa-3,7-diazabicyclo[3.3.1]non-3-yl}ethyl)-4-fluorobenzenesulfonamide;

(xcv) N-(2-{7-[2-(4-cyano-2-fluorophenoxy)ethyl]-9-oxa-3,7-diazabicyclo[3.3.1]non-3-yl}ethyl)-3-fluorobenzenesulfonamide;

(xcvi) N-(2-{7-[2-(4-cyano-2-fluorophenoxy)ethyl]-9-oxa-3,7-diazabicyclo[3.3.1]non-3-yl}ethyl)-3,5-dimethylisoxazole-4-sulfonamide;

(xcvii) 3-cyano-N-(2-{7-[2-(4-cyano-2-fluorophenoxy)ethyl]-9-oxa-3,7-diazabicyclo[3.3.1]non-3-yl}ethyl)benzenesulfonamide;

(xcviii) N-(2-{7-[2-(4-cyano-2-fluorophenoxy)ethyl]-9-oxa-3,7-diazabicyclo[3.3.1]non-3-yl}ethyl)benzenesulfonamide;

(xcix) N-(2-{7-[2-(4-chlorophenyl)ethyl]-9-oxa-3,7-diazabicyclo-[3.3.1]non-3-yl}ethyl)-4-cyanobenzenesulfonamide;

(c) 4-cyano-N-[2-(7-{2-[4-(trifluoromethyl)phenyl]ethyl}-9-oxa-3,7-diazabicyclo[3.3.1]non-3-yl)ethyl]benzenesulfonamide;

(ci) 4-cyano-N-(2-{7-[2-(2,6-difluorophenyl)ethyl]-9-oxa-3,7-diazabicyclo[3.3.1]non-3-yl}ethyl)benzenesulfonamide;

(cii) 4-cyano-N-(2-{7-[2-(2-fluorophenyl)ethyl]-9-oxa-3,7-diazabicyclo[3.3.1]non-3-yl}ethyl)benzenesulfonamide;

(ciii) 4-cyano-N-{2-[7-(2-phenylethyl)-9-oxa-3,7-diazabicyclo[3.3.1]non-3-yl]ethyl}benzenesulfonamide;

(civ) 4-cyano-N-{2-[7-(4-cyanobenzyl)-9-oxa-3,7-diazabicyclo-[3.3.1]non-3-yl]ethyl}-N-methylbenzenesulfonamide;

(cv) N-[2-(7-benzyl-9-oxa-3,7-diazabicyclo[3.3.1]non-3-yl)ethyl]-4-cyano-N-methylbenzenesulfonamide;

(cvi) 4-cyano-N-{2-[7-(4-fluorobenzyl)-9-oxa-3,7-diazabicyclo-[3.3.1]non-3-yl]ethyl}-N-methylbenzenesulfonamide;

(cvii) 4-cyano-N-methyl-N-{2-[7-(2-phenylethyl)-9-oxa-3,7-diazabicyclo[3.3.1]non-3-yl]ethyl}benzenesulfonamide;

(cviii) 4-cyano-N-(2-{7-[2-(3-fluorophenyl)ethyl]-9-oxa-3,7-diazabicyclo-[3.3.1]non-3-yl}ethyl)-N-methylbenzenesulfonamide;

(cix) 4-cyano-N-(2-{7-[2-(2-fluorophenyl)ethyl]-9-oxa-3,7-diazabicyclo-[3.3.1]non-3-yl}ethyl)-N-methylbenzenesulfonamide;

(cx) N-(4-cyanobenzyl)-2-{7-[(3,5-dimethylisoxazol-4-yl)methyl]-9-oxa-3,7-diazabicyclo[3.3.1]non-3-yl}ethanesulfonamide;

(cxi) N-(4-cyanobenzyl)-2-{7-[2-(4-fluorophenyl)ethyl]-9-oxa-3,7-diazabicyclo[3.3.1]non-3-yl}ethanesulfonamide;

(cxii) N-(4-cyanobenzyl)-2-{7-[2-(3-fluorophenyl)ethyl]-9-oxa-3,7-diazabicyclo[3.3.1]non-3-yl}ethanesulfonamide;

(cxiii) N-(2-{7-[2-(4-cyanophenoxy)ethyl]-9-oxa-3,7-diazabicyclo-[3.3.1]non-3-yl}ethyl)-N,3,5-trimethylisoxazole-4-sulfonamide;

(cxiv) N-(2-{7-[2-(4-cyano-2-fluorophenoxy)ethyl]-9-oxa-3,7-diazabicyclo[3.3.1]non-3-yl}ethyl)-1-phenylmethanesulfonamide;

(cxv) N-(2-{7-[2-(4-cyano-2-fluorophenoxy)ethyl]-9-oxa-3,7-diazabicyclo[3.3.1]non-3-yl}ethyl)-2,3-dihydro-1-benzofuran-5-sulfonamide;

(cxvi) N-(2-{7-[2-(4-cyanophenoxy)ethyl]-9-oxa-3,7-diazabicyclo-[3.3.1]non-3-yl}ethyl)-2,4-difluorobenzenesulfonamide;

(cxvii) N-(2-{7-[2-(4-cyano-2-fluorophenoxy)ethyl]-9-oxa-3,7-diaza-bicyclo[3.3.1]non-3-yl}ethyl)-2,4-difluorobenzenesulfonamide;

(cxviii) N-{2-[7-(4-cyanobenzyl)-9-oxa-3,7-diazabicyclo[3.3.1]non-3-yl]ethyl}-4-fluorobenzenesulfonamide;

(cxix) 4-fluoro-N-{2-[7-(4-fluorobenzyl)-9-oxa-3,7-diazabicyclo-[3.3.1]non-3-yl]ethyl}benzenesulfonamide;

(cxx) N-(2-{7-[2-(4-cyanophenyl)ethyl]-9-oxa-3,7-diazabicyclo-[3.3.1]non-3-yl}ethyl)-4-fluorobenzenesulfonamide;

(cxxi) 4-fluoro-N-(2-{7-[2-(4-fluorophenyl)ethyl]-9-oxa-3,7-diazabicyclo-[3.3.1]non-3-yl}ethyl)benzenesulfonamide;

(cxxii) 4-cyano-N-[2-(7-{2-[4-(difluoromethoxy)phenyl]ethyl}-9-oxa-3,7-diazabicyclo[3.3.1]non-3-yl)ethyl]benzenesulfonamide;

(cxxiii) N-(2-{7-[2-(4-cyano-2-fluorophenoxy)ethyl]-9-oxa-3,7-diaza-bicyclo[3.3.1]non-3-yl}ethyl)-2,4-difluoro-N-methylbenzene-sulfonamide;

(cxxiv) 4-cyano-N-(2-{7-[2-(2,6-difluorophenoxy)ethyl]-9-oxa-3,7-diazabicyclo[3.3.1]non-3-yl}ethyl)-N-methylbenzenesulfonamide;

(cxxv) 4-cyano-N-(2-{7-[2-(2-fluorophenoxy)ethyl]-9-oxa-3,7-diaza-bicyclo[3.3.1]non-3-yl}ethyl)-N-methylbenzenesulfonamide;

(cxxvi) N-(2-{7-[2-(1,2-benzisoxazol-3-yl)ethyl]-9-oxa-3,7-diazabicyclo-[3.3.1]non-3-yl}ethyl)-4-cyanobenzenesulfonamide;

(cxxvii) N-(3-{7-[2-(4-cyano-2-fluorophenoxy)ethyl]-9-oxa-3,7-diaza-bicyclo[3.3.1]non-3-yl}propyl)-N-methylbenzenesulfonamide;

(cxxviii) N-(2-{7-[2-(4-cyano-2-fluorophenoxy)ethyl]-9-oxa-3,7-diaza-bicyclo[3.3.1]non-3-yl}ethyl)-N-methyl-2,3-dihydro-1-benzofuran-5-sulfonamide;

(cxxix) N-(2-{7-[2-(4-cyanophenoxy)ethyl]-9-oxa-3,7-diazabicyclo[3.3.1]-non-3-yl}ethyl)-N-methyl-2,3-dihydro-1-benzofuran-5-sulfonamide;

(cxxx) 4-cyano-N-{2-[7-(4-cyano-2-fluorobenzyl)-9-oxa-3,7-diazabicyclo-[3.3.1]non-3-yl]ethyl}benzenesulfonamide;

(cxxxi) 4-cyano-N-{2-[7-(4-eyano-2-fluorobenzyl)-9-oxa-3,7-diazabicyclo-[3.3.1]non-3-yl]ethyl}-N-methylbenzenesulfonamide;

(cxxxii) 4-cyano-N-[2-(7-{2-[4-(difluoromethoxy)phenyl]ethyl}-9-oxa-3,7-diazabicyclo[3.3.1]non-3-yl)ethyl]-N-methylbenzenesulfonamide;

(cxxxiii) 4-fluoro-N-(2-{7-[2-(3-fluorophenyl)ethyl]-9-oxa-3,7-diazabicyclo-[3.3.1]non-3-yl}ethyl)benzenesulfonamide;

(cxxxiv) 4-fluoro-N-(2-{7-[2-(2-fluorophenyl)ethyl]-9-oxa-3,7-diazabicyclo-[3.3.1]non-3-yl}ethyl)benzenesulfonamide;

(cxxxv) 4-fluoro-N-{2-[7-(2-phenylethyl)-9-oxa-3,7-diazabicyclo[3.3.1]non-3-yl]ethyl}benzenesulfonamide;

(cxxxvi) N-{2-[7-(1,2-benzisoxazol-3-ylmethyl)-9-oxa-3,7-diazabicyclo-[3.3.1]non-3-yl]ethyl}-4-cyanobenzenesulfonamide;

(cxxxvii) 4-cyano-N-(2-{7-[2-(4-fluorophenyl)ethyl]-9-oxa-3,7-diazabicyclo[3.3.1]non-3-yl}ethyl)-N-methylbenzenesulfonamide;

(cxxxviii) 4-cyano-N-(2-{7-[2-(3,4-difluorophenyl)ethyl]-9-oxa-3,7-diazabicyclo[3.3.1]non-3-yl}ethyl)-N-methylbenzenesulfonamide;

(cxxxix) 4-cyano-N-{3-[7-(4-cyanobenzyl)-9-oxa-3,7-diazabicyclo-[3.3.1]non-3-yl]propyl}benzenesulfonamide;

(cxl) 4-cyano-N-{3-[7-(4-fluorobenzyl)-9-oxa-3,7-diazabicyclo-[3.3.1]non-3-yl]propyl}benzenesulfonamide;

(cxli) 4-cyano-N-(3-{7-[2-(4-fluorophenyl)ethyl]-9-oxa-3,7-diazabicyclo-[3.3.1]non-3-yl}propyl)benzenesulfonamide;

(cxlii) 4-cyano-N-(3-{7-[2-(3-fluorophenyl)ethyl]-9-oxa-3,7-diazabicyclo-[3.3.1]non-3-yl}propyl)benzenesulfonamide;

(cxliii) 4-cyano-N-(3-{7-[2-(2-fluorophenyl)ethyl]-9-oxa-3,7-diazabicyclo-[3.3.1]non-3-yl}propyl)benzenesulfonamide;

(cxliv) 4-cyano-N-(3-{7-[2-(2,6-difluorophenyl)ethyl]-9-oxa-3,7-diazabicyclo[3.3.1]non-3-yl}propyl)benzenesulfonamide;

(cxlv) 4-cyano-N-(3-{7-[2-(3,4-difluorophenyl)ethyl]-9-oxa-3,7-diazabicyclo[3.3.1]non-3-yl}propyl)benzenesulfonamide;

(cxlvi) N-[3-(7-benzyl-9-oxa-3,7-diazabicyclo[3.3.1]non-3-yl)propyl]-4-cyanobenzenesulfonamide;

(cxlvii) 4-cyano-N-(3-{7-[3-(4-fluorophenoxy)propyl]-9-oxa-3,7-diazabicyclo[3.3.1]non-3-yl}propyl)benzenesulfonamide;

(cxlviii) 4-cyano-N-(3-{7-[2-(2,6-difluorophenoxy)ethyl]-9-oxa-3,7-diazabicyclo[3.3.1]non-3-yl}propyl)benzenesulfonamide;

(cxlix) 4-cyano-N-(2-{7-[3-(4-fluorophenoxy)propyl]-9-oxa-3,7-diazabicyclo[3.3.1]non-3-yl}ethyl)-N-methylbenzenesulfonamide;

(cl) 4-cyano-N-(2-{7-[3-(2,4-difluorophenoxy)propyl]-9-oxa-3,7-diazabicyclo[3.3.1]non-3-yl}ethyl)-N-methylbenzenesulfonamide;

(cli) 4-cyano-N-(2-{7-[2-(2,4-difluorophenyl)ethyl]-9-oxa-3,7-diazabicyclo[3.3.1]non-3-yl}ethyl)benzenesulfonamide;

(clii) 4-cyano-N-(2-{7-[3-(2,4-difluorophenoxy)propyl]-9-oxa-3,7-diazabicyclo[3.3.1]non-3-yl}ethyl)benzenesulfonamide;

(cliii) N-(2-{7-[2-(4-chlorophenyl)ethyl]-9-oxa-3,7-diazabicyclo-[3.3.1]non-3-yl}ethyl)-4-cyano-N-methylbenzenesulfonamide; and (cliv) 4-Cyano-N-(2-{7-[2-(2,4-difluoro-phenyl)-ethyl]-9-oxa-3,7-diaza-bicyclo[3.3.1]non-3-yl}-ethyl)-N-methyl-benzenesulfonamide;

or a pharmaceutically acceptable salt thereof.

Preparation

According to the invention there is also provided a process for the preparation of compounds of formula I which comprises:

(a) reaction of a compound of formula II,

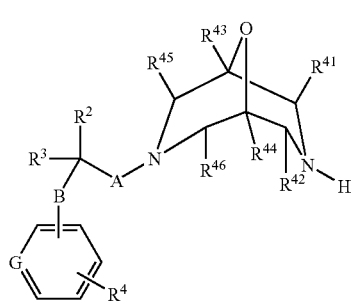

wherein $R^2$, $R^3$, $R^4$, $R^{41}$ to $R^{46}$, A, B and G are as hereinbefore defined, with a compound of formula III, $$R^1\text{-}L^1 \qquad \text{III}$$

wherein $L^1$ represents a leaving group such as halo, alkanesulfonate, perfluoroalkanesulfonate, arenesulfonate, —OC(O)XR$^7$, Imidazole or $R^{23}$O— (wherein $R^{23}$ represents, for example, $Cl_{1-10}$ alkyl or aryl, which groups are optionally substituted by one or more halo or nitro groups) and X, $R^1$ and $R^7$ are as hereinbefore defined, for example at between room and reflux temperature in the presence of a suitable base (e.g. triethylamine, potassium carbonate or a bicarbonate, such as sodium bicarbonate) and an appropriate solvent (e.g. dichloromethane, chloroform, acetonitrile, N,N-dimethylformamide, THF, toluene, water, a lower alkyl alcohol (e.g. ethanol) or mixtures thereof);

(b) for compounds of formula I in which $R^1$ represents $C_{1-12}$ alkyl substituted by one or more substituents as defined above in respect of $R^1$, which substituent(s) is/include a —N($R^{9b}$)S(O)$_2$R$^{9d}$ group, reaction of a compound of formula IV,

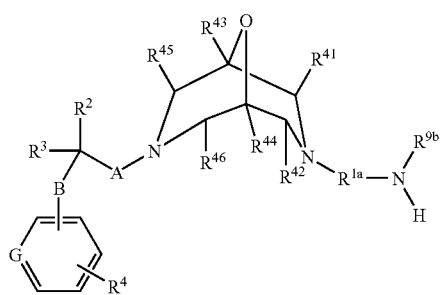

wherein $R^{1a}$ represents $C_{1-12}$ alkylene, which group is optionally substituted by one or more substituents as defined above in respect of $R^1$, and $R^2$, $R^3$, $R^4$, $R^{41}$ to $R^{46}$, A, B and G are as hereinbefore defined, with a compound of formula V,

   V wherein $L^2$ represents a suitable leaving group such as halo and $R^{9d}$ is as hereinbefore defined, for example under conditions that are know to those skilled in the art (e.g. at ambient temperature (such as from 15 to 30° C.) in the presence of a suitable base (such as such as triethylamine, potassium carbonate or sodium hydrogencarbonate) and an appropriate solvent (such as DCM, $CHCl_3$, acetonitrile, DMF, THF, toluene, or mixtures thereof);

(c) for compounds of formula I in which $R^1$ represents $C_{1-12}$ alkyl substituted by one or more substituents as defined above in respect of $R^1$, which substituent(s) is/include a $-S(O)_2N(R^{9b})R^{9c}$ group, reaction of a compound of formula II, as hereinbefore defined, with a compound of formula VA,

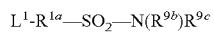   VA wherein $L^1$, $R^{1a}$, $R^{9b}$ and $R^{9c}$ are as hereinbefore defined, for example under conditions that are know to those skilled in the art (e.g. at ambient temperature to reflux in the presence of a suitable base (such as such as triethylamine, potassium carbonate or sodium hydrogencarbonate) and an appropriate solvent (such as DCM, $CHCl_3$, acetonitrile, DMF, THF, toluene, or mixtures thereof);

(d) for compounds of formula I in which $R^1$ represents $-C(O)XR^7$ or $-C(O)N(R^{8a})R^{5d}$, reaction of a compound of formula VI,

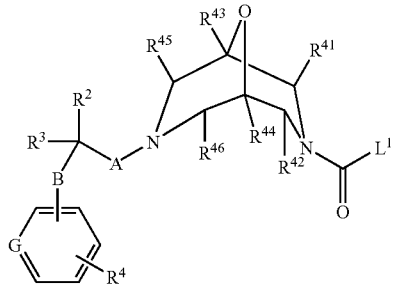   VI wherein $R^2$, $R^3$, $R^4$, $R^{41}$ to $R^{46}$, A, B, G and $L^1$ are as hereinbefore defined, with a compound of formula VII,

   VII wherein $R^{24}$ represents $-XR^7$ or $-N(R^{8a})R^{5d}$ and $R^{5d}$, $R^7$, $R^{8a}$ and X are as hereinbefore defined, for example under similar conditions to those described hereinbefore (process step (a));

(e) for compounds of formula I in which $R^1$ represents $-C(O)N(H)R^{8a}$, reaction of a compound of formula II, as hereinbefore defined, with a compound of formula VIII,

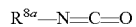   VIII wherein $R^{8a}$ is as hereinbefore defined, for example at between 0° C. and reflux temperature in the presence of an appropriate organic solvent (e.g. dichloromethane), or via solid phase synthesis under conditions known to those skilled in the art;

(f) reaction of a compound of formula IX,

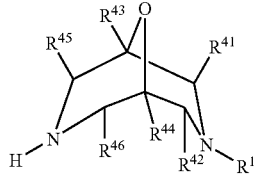   IX wherein $R^1$ and $R^{41}$ to $R^{46}$ are as hereinbefore defined, with a compound of formula X,

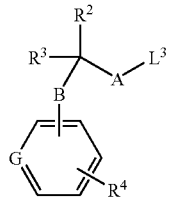   X wherein $L^3$ represents a leaving group such as halo, alkanesulfonate (e.g. mesylate), perfluoroalkanesulfonate or arenesulfonate (e.g. 2- or 4-nitrobenzenesulfonate, toluenesulfonate or benzenesulfonate) and $R^2$, $R^3$, $R^4$, A, B and G are as hereinbefore defined, for example at elevated temperature (e.g. between 35° C. and reflux temperature) in the presence of a suitable base (e.g. triethylamine or potassium carbonate) and an appropriate organic solvent (e.g. acetonitrile, dichloromethane, chloroform, dimethylsulfoxide, N,N-dimethylformamide, a lower alkyl alcohol (e.g. ethanol), isopropyl acetate or mixtures thereof);

(g) for compounds of formula I in which B represents $-Z-N(R^{20c})S(O)_2-$, reaction of a compound of formula IX, as hereinbefore defined, with a compound of formula XA,

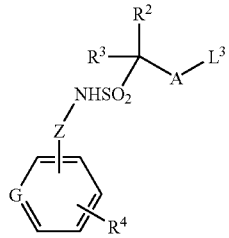   XA wherein $R^2$, $R^3$, $R^4$, A, G, Z and $L^3$ are as hereinbefore defined, for example under conditions described in respect of process (f) above;

(h) for compounds of formula I in which A represents $CH_2$ and $R^2$ represents $-OH$ or $-N(H)R^{14}$, reaction of a compound of formula IX, as hereinbefore defined, with a compound of formula XI,

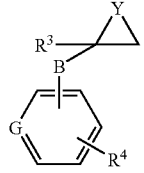   XI wherein Y represents O or $N(R^{14})$ and $R^3$, $R^4$, $R^{14}$, B and G are as hereinbefore defined, for example at elevated temperature (e.g. 60° C. to reflux) in the presence of a suitable solvent (e.g. a lower alkyl alcohol (e.g. IPA), acetonitrile, or a mixture of a lower alkyl alcohol and water);

(i) for compounds of formula I in which B represents —Z—O—, reaction of a compound of formula XII,

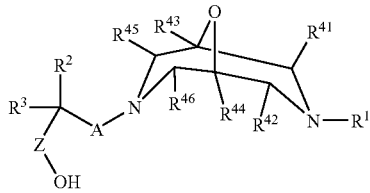

XII wherein $R^1$, $R^2$, $R^3$, $R^{41}$ to $R^{46}$, A and Z are as hereinbefore defined, with a compound of formula XIII,

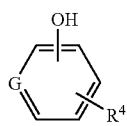

XIII wherein $R^4$ and G are as hereinbefore defined, for example under Mitsunobu-type conditions e.g. at between ambient (e.g. 25° C.) and reflux temperature in the presence of a tertiary phosphine (e.g. tributylphosphine or triphenylphosphine), an azodicarboxylate derivative (e.g. diethylazodicarboxylate or 1,1'-(azodicarbonyl)dipiperidine) and an appropriate organic solvent (e.g. dichloromethane or toluene);

(j) for compounds of formula I in which G represents N and B represents —Z—O—, reaction of a compound of formula XII, as hereinbefore defined, with a compound of formula XIV,

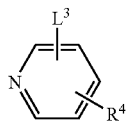

XIV wherein $R^4$ and $L^3$ are as hereinbefore defined, for example at between 10° C. and reflux temperature in the presence of a suitable base (e.g. sodium hydride) and an appropriate solvent (e.g. N,N-dimethylformamide);

(k) for compounds of formula I in which $R^2$ represents —$OR^3$, in which $R^{13}$ represents $C_{1-6}$ alkyl, -E-aryl or -E-$Het^8$, reaction of a compound of formula I in which $R^2$ represents OH with a compound of formula XV,

  XV wherein $R^{13a}$ represents $C_{1-6}$ alkyl, -E-aryl or -E-$Het^8$ and E and $Het^8$ are as hereinbefore defined, for example under Mitsunobu-type conditions (e.g. as described hereinbefore in process step (h));

(l) for compounds of formula I in which $R^2$ represents —$OR^3$, in which $R^{13}$ represents $C_{1-6}$ alkyl, -E-aryl or -E-$Het^8$, reaction of a compound of formula XVI,

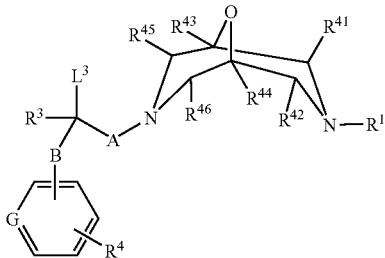

XVI wherein $R^1$, $R^3$, $R^4$, $R^{41}$ to $R^{46}$, A, B, G and $L^3$ are as hereinbefore defined, with a compound of formula XV, as hereinbefore defined, for example at between ambient (e.g. 25° C.) and reflux temperature, under Williamson-type conditions (i.e. in the presence of an appropriate base (e.g. KOH or NaH) and a suitable organic solvent (e.g. dimethylsulfoxide or N,N-dimethyl-formamide)) (the skilled person will appreciate that certain compounds of formula XVI (e.g. those in which $L^3$ represents halo) may also be regarded as compounds of formula I as hereinbefore defined);

(m) for compounds of formula I in which $R^2$ represents -E-$NH_2$, reduction of a compound of formula XVII,

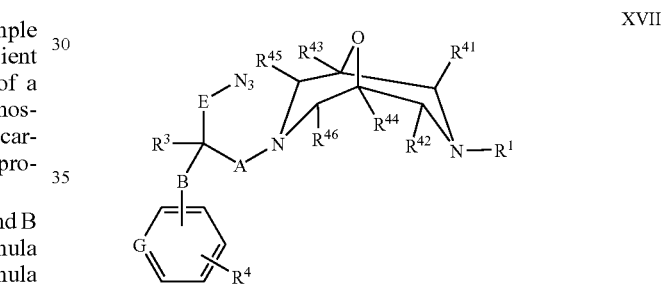

XVII wherein $R^1$, $R^3$, $R^4$, $R^{41}$ to $R^{46}$, A, B, E and G are as hereinbefore defined, for example by hydrogenation at a suitable pressure in the presence of a suitable catalyst (e.g. palladium on carbon) and an appropriate solvent (e.g. a water-ethanol mixture);

(n) for compounds of formula I in which $R^2$ represents -E-N($R^{14}$)$R^{15}$, wherein $R^{14}$ represents $C_{1-6}$ alkyl, -E-aryl -E-$Het^9$, —C(O)$R^{16a}$, —C(O)O$R^{16b}$, —S(O)$_2R^{16c}$ or —C(O)N($R^{17a}$)$R^{17b}$, reaction of a compound of formula I in which $R^2$ represents -E-N(H)$R^{15}$ with a compound of formula XVIII,

 XVIII wherein $R^{14a}$ represents $C_{1-6}$ alkyl, -E-aryl -E-$Het^9$, —C(O)$R^{16a}$, —C(O)O$R^{16b}$, —S(O)$_2R^{16c}$ or —C(O)N($R^{17a}$)$R^{17b}$, and $R^{16a}$, $R^{16b}$, $R^{16c}$, $R^{17a}$, $R^{17b}$, $Het^9$, E and $L^1$ are as hereinbefore defined, for example under conditions described hereinbefore (process step (a));

(o) for compounds of formula I in which $R^2$ represents -E-N($R^{15}$)C(O)N(H)$R^{17a}$, reaction of a compound of formula I in which $R^2$ represents -E-N(H)$R^{15}$ with a compound of formula XIX,

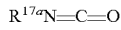 XIX wherein $R^{17}$ is as hereinbefore defined, for example under conditions described hereinbefore (process step (e));

(p) for compounds of formula I in which $R^2$ represents -E-N(H)[C(O)]$_2$NH$_2$, reaction of a compound of formula I in which $R^2$ represents -E-NH$_2$ with oxalic acid diamide, for example at between −10 and 25° C. in the presence of a suitable coupling agent (e.g. 1-(3-dimethyl-aminopropyl)-3-ethylcarbodiimide), an appropriate activating agent (e.g. 1-hydroxybenzotriazole), a suitable base (e.g. triethylamine) and a reaction-inert solvent (e.g. N,N-dimethylformamide);

(q) for compounds of formula I in which $R^2$ represents -E-N(H)C(NH)NH$_2$, reaction of a compound of formula I in which $R^2$ represents -E-NH$_2$ with a compound of formula XX,

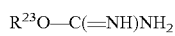       XX or an N-protected derivative thereof, wherein $R^{23}$ is as hereinbefore defined, for example at between room and reflux temperature, optionally in the presence of a suitable solvent (e.g. toluene) and/or an appropriate acidic catalyst (e.g. acetic acid at, for example, 10 mol %);

(r) for compounds of formula I in which $R^2$ represents —OR$^{13}$, in which $R^{13}$ represents —C(O)R$^{16a}$, —C(O)OR$^{16b}$ or —C(O)N(R$^{17a}$)R$^{17b}$, reaction of a compound of formula I in which $R^2$ represents —OH with a compound of formula XX$^1$,

       XXI wherein $R^{13b}$ represents —C(O)R$^{16a}$, —C(O)OR$^{16b}$ or —C(O)N(R$^{17a}$)R$^{17b}$, L$^4$ represents a leaving group such as halo, p-nitrophenoxy, —OC(O)R$^{16a}$, —OC(O)OR$^{16b}$, —OH or imidazole and R$^{16a}$, R$^{16b}$, R$^{17a}$ and R$^{17b}$ are as hereinbefore defined, for example at between −10° C. and reflux temperature in the presence of a suitable base (e.g. triethylamine, pyridine or potassium carbonate), an appropriate organic solvent (e.g. THF, dichloromethane or acetonitrile) and (where appropriate) a suitable coupling agent (e.g. 1-(3-dimethylaminopropyl)-3-ethylcarbodiimide);

(s) for compounds of formula I in which $R^2$ represents H or —OH and $R^3$ represents H, reduction of a compound of formula I in which $R^2$ and $R^3$ together represent=O, in the presence of a suitable reducing agent and under appropriate reaction conditions; for example, for formation of compounds of formula I in which $R^2$ represents OH, reduction may be performed under mild reaction conditions in the presence of e.g. sodium borohydride and an appropriate organic solvent (e.g. THF); for formation of compounds of formula I in which $R^2$ represents OH, wherein the compound is enantiomerically enriched (or is a single enantiomer) at the chiral centre to which $R^2$ is attached, reduction may be performed enzymatically (for example under conditions known to those skilled in the art, such as in the presence of horse liver alcohol dehydrogenase and NADPH) or by hydrogenation in the presence of a suitable solution-phase (homogeneous) catalyst under conditions known to those skilled in the art; and for formation of compounds of formula I in which $R^2$ represents H, reduction may be performed either under Wolff-Kischner conditions known to those skilled in the art or by activating the relevant C=O group using an appropriate agent (such as tosylhydrazine) in the presence of a suitable reducing agent (e.g. sodium borohydride or sodium cyanoborohydride) and an appropriate organic solvent (e.g. a lower (e.g. C$_{1-6}$) alkyl alcohol);

(t) for compounds of formula I in which $R^2$ represents halo, substitution of a corresponding compound of formula I in which $R^2$ represents —OH, using an appropriate halogenating agent (e.g. for compounds in which $R^2$ represents fluoro, reaction with (diethylamino)sulfur trifluoride);

(u) for compounds of formula I in which $R^2$ and $R^3$ represent H, A represents -J- and B represents —N(R$^{20e}$)—Z— (wherein —N(R$^{20e}$) is attached to the carbon atom bearing $R^2$ and $R^3$), reaction of a compound of formula XXII,

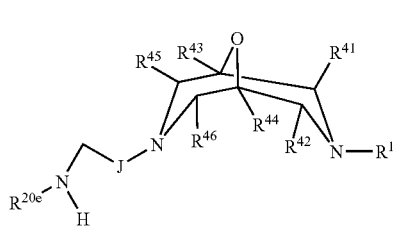       XXII wherein $R^1$, $R^{20e}$, $R^{41}$ to $R^{46}$ and J are as hereinbefore defined, with a compound of formula XXIII,

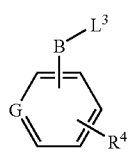       XXIII wherein $R^4$, G, Z and $L^3$ are as hereinbefore defined, for example at elevated temperature (e.g. 40° C. to reflux) in the presence of a suitable organic solvent (e.g. acetonitrile);

(v) for compounds of formula I in which A represents —(CH$_2$)$_2$— and $R^2$ and $R^3$ together represent =O, reaction of a compound of formula IX, as hereinbefore defined, with a compound of formula XXIV,

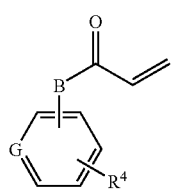       XXIV wherein B, G and $R^4$ are as hereinbefore defined, for example at between room and reflux temperature in the presence of a suitable base (e.g. triethylamine, potassium carbonate or tetrabutylammonium hydroxide) and an appropriate organic solvent (e.g. a lower alkyl (e.g. C$_{1-6}$) alcohol);

(w) for compounds of formula I in which $R^1$ represents —C(O)XR$^7$, —C(O)N(R$^{8a}$)R$^{5d}$ or —S(O)$_2$R$^{9a}$, reaction of a compound of formula XXV,

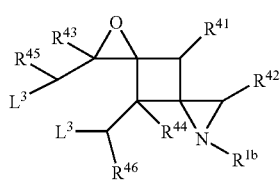       XXV wherein $R^{1b}$ represents —C(O)XR$^7$, —C(O)N(R$^{8a}$)R$^{5b}$ or —S(O)$_2$R$^{9a}$ and R$^{5d}$, R$^7$, R$^{8a}$, R$^{9a}$, R$^{41}$ to R$^{46}$ and L are as hereinbefore defined, with a compound of formula XXVI,

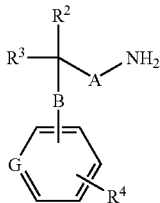

XXVI wherein $R^2$, $R^3$, $R^4$, A, B and G are as hereinbefore defined, for example at between room and reflux temperature in the presence of a suitable base (e.g. sodium hydrogencarbonate or potassium carbonate) and an appropriate organic solvent (e.g. acetonitrile);

(x) for compounds of formula I which are oxabispidine-nitrogen N-oxide derivatives, oxidation of the corresponding oxabispidine nitrogen of a corresponding compound of formula I, in the presence of a suitable oxidising agent (e.g. mCPBA), for example at 0° C. in the presence of a suitable organic solvent (e.g. dichloromethane);

(y) for compounds of formula I which are $C_{1-4}$ alkyl quaternary ammonium salt derivatives, in which the alkyl group is attached to a oxabispidine nitrogen, reaction, at the oxabispidine nitrogen, of a corresponding compound of formula I with a compound of formula XXVII, $$R^{25}\text{-}L^5 \qquad \text{XXVII}$$

wherein $R^{25}$ represents $C_{1-4}$ alkyl and $L^5$ is a leaving group such as halo, alkanesulfonate or arenesulfonate, for example at room temperature in the presence of an appropriate organic solvent (e.g. N,N-dimethylformamide), followed by purification (using e.g. HPLC) in the presence of a suitable counterion provider (e.g. NH$_4$OAc);

(z) conversion of one $R^4$ substituent to another using techniques well known to those skilled in the art; or (aa) introduction of one or more (further) $R^4$ substituents to the aromatic ring using techniques well known to those skilled in the art (e.g. chlorination).

(ab) for compounds of formula I in wherein $R^1$ represents $C_{1-12}$ alkylene, which group is optionally substituted by one or more substituents as defined above in respect of $R^1$, reaction of a compound of formula II

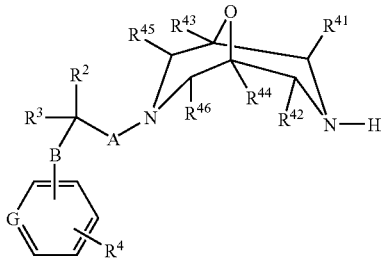

II wherein $R^2$, $R^3$, $R^4$, $R^{41}$ to $R^{46}$, A, B and G are as hereinbefore defined, with the appropriate aldehyde, for example under conditions that are known to those skilled in the art (e.g. at room temperature, such as from 15 to 30° C.) in the presence of a reducing agent (such as sodium cyanoborohydride, sodium triacetoxyborohydride, or similar compounds) and an appropriate solvent (such as 1,2-dichloroethane, dichloroethane, methanol, ethanol or mixtures thereof);

(ac) for compounds of formula I in wherein A represents -J-, -J-N(R$^{19a}$)—, -J-S(O)$_2$N(R$^{19b}$)—, -J-N(R$^{19c}$)S(O)$_2$— or -J-O— (in which latter four groups, -J is attached to the oxabispidine ring nitrogen), reaction of a compound with formula VII

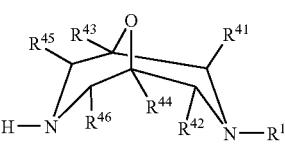

VII wherein $R^1$ and $R^{41}$ to $R^{46}$ are as hereinbefore defined, with a compound of formula XXIII

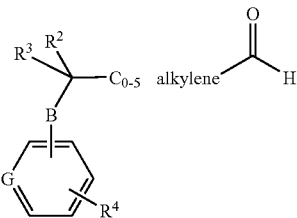

XXIII wherein $R^2$, $R^4$, B and G are as hereinbefore defined and the $C_{0-5}$ alkylene group is optionally substituted by one or more substituents as defined above in respect of J, for example under conditions that are known to those skilled in the art (e.g. at room temperature, such as from 15 to 30° C.) in the presence of a reducing agent (such as sodium cyanoborohydride, sodium triacetoxyborohydride, or similar hydride donating compounds) and an appropriate solvent (such as 1,2-dichloroethane, dichloroethane, methanol, ethanol or mixtures thereof); or (ad) deprotection of a protected derivative of a compound of formula I as defined above.

Compounds of formulae II, IV, IX, X, XI, XII, XVI, XVII, XXII and XXV may be prepared according to or by analogy with the procedures described or referred to in WO 01/28992, WO 02/28863, WO 02/28864, WO 02/83690 and WO 02/83691, the disclosures of which documents are hereby incorporated by reference.

Compounds of formula VA may be prepared by reaction of a compound of formula XXVIII, $$\text{HN}(R^{9b})R^{9c} \qquad \text{XXVIII}$$

wherein $R^{9b}$ and $R^{9c}$ are as hereinbefore defined, with a compound of formula XXIX, $$L^1\text{-}R^{1a}\text{—SO}_2\text{-}L^2 \qquad \text{XXIX}$$

wherein $L^1$, $L^2$ and $R^{1a}$ are as hereinbefore defined, for example under conditions known to those skilled in the art (e.g. those described in respect of process (b) above).

Compounds of formula XA may be prepared by reaction of a compound of formula XXX, $$L^2\text{-SO}_2\text{-A-}L^3 \qquad \text{XXX}$$

wherein A, L² and L³ are as hereinbefore defined, with a compound of formula XXXI,

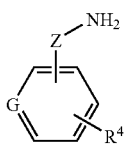

wherein R⁴, G and Z are as hereinbefore defined, for example under conditions known to those skilled in the art (e.g. those described in respect of process (b) above).

Compounds of formulae III, V, VII, VIII, XIII, XIV, XV, XVIII, XIX, XX, XXI, XXIII, XXIV, XXVI, XXVII, XXVIII, XXIX, XXX, XXXI and derivatives thereof, are either commercially available, are known in the literature, or may be obtained either by analogy with the processes described herein, or by conventional synthetic procedures, in accordance with standard techniques, from readily available starting materials using appropriate reagents and reaction conditions.

Substituents on the aryl (e.g. phenyl), and (if appropriate) heterocyclic, group(s) in compounds defined herein may be converted to other claimed substituents using techniques well known to those skilled in the art. For example, hydroxy may be converted to alkoxy, phenyl may be halogenated to give halophenyl, nitro may be reduced to give amino, halo may be displaced by cyano, etc.

The skilled person will also appreciate that various standard substituent or functional group interconversions and transformations within certain compounds of formula I will provide other compounds of formulae I. For example, carbonyl may be reduced to hydroxy or alkylene, and hydroxy may be converted to halo.

The compounds of the invention may be isolated from their reaction mixtures using conventional techniques.

It will be appreciated by those skilled in the art that, in the process described above, the functional groups of intermediate compounds may be, or may need to be, protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyl groups (e.g. methyl- and ethylcarbonyl groups). Suitable protecting groups for amino include benzyl, sulfonamido (e.g. benzenesulfonamido), tert-butyloxycarbonyl, 9-fluorenylmethoxycarbonyl or benzyloxycarbonyl. Suitable protecting groups for amidino and guanidino include benzyloxycarbonyl. Suitable protecting groups for carboxylic acid include $C_{1-6}$ alkyl or benzyl esters.

The protection and deprotection of functional groups may take place before or after any of the reaction steps described hereinbefore. Protecting groups may be removed in accordance with techniques which are well known to those skilled in the art and as described hereinafter.

The use of protecting groups is fully described in "Protective Groups in Organic Chemistry", edited by J. W. F. McOmie, Plenum Press (1973), and "Protective Groups in Organic Synthesis", 3rd edition, T. W. Greene & P. G. M. Wutz, Wiley-Interscience (1999).

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

It will also be appreciated by those skilled in the art that, although certain protected derivatives of compounds of formula I, which may be made prior to a final deprotection stage, may not possess pharmacological activity as such, they may be administered parenterally or orally and thereafter metabolised in the body to form compounds of the invention which are pharmacologically active. Such derivatives may therefore be described as "prodrugs". Moreover, certain compounds of formula I may act as prodrugs of other compounds of formula I.

All prodrugs of compounds of formula I are included within the scope of the invention.

Some of the intermediates referred to hereinbefore are novel. According to a further aspect of the invention there is thus provided:

(a) a compound of formula II, as hereinbefore defined, or a protected derivative thereof, provided that
   (i) A represents -J-S(O)₂N(R¹⁹ᵇ)— or -J-N(R¹⁹ᶜ)S(O)₂—,
   (ii) J is interrupted by —S(O)₂N(R¹⁹ᵈ)— or —N(R¹⁹ᵉ)S(O)₂—,
   (iii) B represents —Z—N(R²ᶜ)S(O)₂—, —Z—S(O)₂N(R²ᵈ)—, —N(R²⁰ᶠ)S(O)₂—Z— or —S(O)₂N(R²⁰ᵍ)—Z— and/or
   (iv) Z is interrupted by —N(R²⁰ⁱ)S(O)₂— or —S(O)₂N(R²⁰ⁱ)—;

(b) a compound of formula IV, as hereinbefore defined, or a protected derivative thereof, provided that
   (i) A represents -J-S(O)₂N(R¹⁹ᵇ)— or -J-N(R¹⁹ᶜ)S(O)₂—,
   (ii) J is interrupted by —S(O)₂N(R¹⁹ᵈ)— or —N(R¹⁹ᵉ)S(O)₂—,
   (iii) B represents —Z—N(R²⁰ᶜ)S(O)₂—, —Z—S(O)₂N(R²⁰ᵈ)—, —N(R²⁰ᶠ)S(O)₂—Z— or —S(O)₂N(R²⁰ᵍ)—Z— and/or
   (iv) Z is interrupted by —N(R²⁰ⁱ)S(O)₂— or —S(O)₂N(R²⁰ʲ)—;

(c) a compound of formula VI, as hereinbefore defined, or a protected derivative thereof, provided that
   (i) A represents -J-S(O)₂N(R¹⁹ᵇ)— or -J-N(R¹⁹ᶜ)S(O)₂—,
   (ii) J is interrupted by —S(O)₂N(R⁹ᵈ)— or —N(R¹⁹ᵉ)S(O)₂—,
   (iii) B represents —Z—N(R²⁰ᶜ)S(O)₂—, —Z—S(O)₂N(R²¹ᵈ)—, —N(R²⁰ᶠ)S(O)₂—Z— or —S(O)₂N(R²⁰ᵍ)—Z— and/or
   (iv) Z is interrupted by —N(R²⁰ⁱ)S(O)₂— or —S(O)₂N(R²⁰ʲ)—;

(d) a compound of formula IX, as hereinbefore defined, or a protected derivative thereof, provided that R¹ represents $C_{1-12}$ alkyl (which alkyl group is substituted by one or more groups including at least one —S(O)₂N(R⁹ᵇ)R⁹ᶜ and/or —N(R⁹ᵇ)S(O)₂R⁹ᵈ group);

(e) a compound of formula X, as hereinbefore defined, or a protected derivative thereof, provided that
   (i) A represents -J-S(O)₂N(R¹⁹ᵇ)— or -J-N(R⁹ᶜ)S(O)₂—,
   (ii) J is interrupted by —S(O)₂N(R¹⁹ᵈ)— or —N(R¹⁹ᵉ)S(O)₂—, (iii) B represents —Z—N($R^{20c}$)S(O)$_2$—, —Z—S(O)$_2$N($R^{20d}$)—, —N($R^{20g}$)S(O)$_2$—Z— or —S(O)$_2$N($R^{21g}$)—Z— and/or (iv) Z is interrupted by —N($R^{20i}$)S(O)$_2$— or —S(O)$_2$N($R^{20j}$)—;

(f) a compound of formula XI, as hereinbefore defined, or a protected derivative thereof, provided that
  (i) B represents —Z—N($R^{20c}$)S(O)$_2$—, —Z—S(O)$_2$N($R^{20d}$)—, —N($R^{20f}$)S(O)$_2$—Z— or —S(O)$_2$N($R^{20g}$)—Z— and/or
  (ii) Z is interrupted by —N($R^{20i}$)S(O)$_2$— or —S(O)$_2$N($R^{20j}$)—;

(g) a compound of formula XII, as hereinbefore defined, or a protected derivative thereof, provided that
  (i) $R^1$ represents $C_{1-12}$ alkyl (which alkyl group is substituted by one or more groups including at least one —S(O)$_2$N($R^{9b}$)$R^{9c}$ and/or —N($R^{9b}$)S(O)$_2$$R^{9d}$ group),
  (ii) A represents -J-S(O)$_2$N($R^{19b}$)— or -J-N($R^{19c}$)S(O)$_2$—, and/or
  (iii) J is interrupted by —S(O)$_2$N($R^{19d}$)— or —N($R^{19e}$)S(O)$_2$—;

(h) a compound of formula XVII, as hereinbefore defined, or a protected derivative thereof, provided that
  (i) $R^1$ represents $C_{1-12}$ alkyl (which alkyl group is substituted by one or more groups including at least one —S(O)$_2$N($R^{9b}$)$R^{9c}$ and/or —N($R^{9b}$)S(O)$_2$$R^{9d}$ group),
  (ii) A represents -J-S(O)$_2$N($R^{19b}$)— or -J-N($R^{19c}$)S(O)$_2$—, and/or
  (iii) J is interrupted by —S(O)$_2$N($R^{9d}$)— or —N($R^{19e}$)S(O)$_2$—,
  (iv) B represents —Z—N($R^{20c}$)S(O)$_2$—, —Z—S(O)$_2$N($R^{20d}$)—, —N($R^{20f}$)S(O)$_2$—Z— or —S(O)$_2$N($R^{20g}$)—Z— and/or
  (v) Z is interrupted by —N($R^{20i}$)S(O)$_2$— or —S(O)$_2$N($R^{20j}$)—;

(i) a compound of formula XXII, as hereinbefore defined, or a protected derivative thereof, provided that
  (i) $R^1$ represents $C_{1-12}$ alkyl (which alkyl group is substituted by one or more groups including at least one —S(O)$_2$N($R^{9b}$)$R^{9c}$ and/or —N($R^{9b}$)S(O)$_2$$R^{9d}$ group), and/or
  (ii) J is interrupted by —S(O)$_2$N($R^{19d}$)— or —N($R^{19e}$)S(O)$_2$—;

(j) a compound of formula XXII, as hereinbefore defined, or a protected derivative thereof, provided that
  (i) B represents —Z—N($R^{20c}$)S(O)$_2$—, —Z—S(O)$_2$N($R^{20d}$)—, —N($R^{20f}$)S(O)$_2$—Z— or —S(O)$_2$N($R^{20g}$)—Z— and/or
  (ii) Z is interrupted by —N($R^{20i}$)S(O)$_2$— or —S(O)$_2$N($R^{20j}$)—;

(k) a compound of formula XXIV, as hereinbefore defined, or a protected derivative thereof, provided that
  (i) B represents —Z—N($R^{20c}$)S(O)$_2$—, —Z—S(O)$_2$N($R^{20d}$)—, —N($R^{20f}$)S(O)$_2$—Z— or —S(O)$_2$N($R^{20g}$)—Z— and/or
  (ii) Z is interrupted by —N($R^{20i}$)S(O)$_2$— or —S(O)$_2$N($R^{20j}$)—; and (l) a compound of formula XXVI, as hereinbefore defined, or a protected derivative thereof, provided that
  (i) A represents -J-S(O)$_2$N($R^{19b}$) or -J-N($R^{19c}$)S(O)$_2$,
  (ii) J is interrupted by —S(O)$_2$N($R^{19d}$)— or —N($R^{19e}$)S(O)$_2$—,
  (iii) B represents —Z—N($R^{20c}$)S(O)$_2$—, —Z—S(O)$_2$N($R^{20d}$)—, —N($R^{20}$)S(O)$_2$—Z— or —S(O)$_2$N($R^{20g}$)—Z— and/or
  (iv) Z is interrupted by —N($R^{20i}$)S(O)$_2$— or —S(O)$_2$N($R^{21j}$)—.

Medical and Pharmaceutical Use

Compounds of the invention are useful because they possess pharmacological activity. They are therefore indicated as pharmaceuticals.

Thus, according to a further aspect of the invention there is provided the compounds of the invention for use as pharmaceuticals.

In particular, the compounds of the invention exhibit myocardial electrophysiological activity, for example as demonstrated in the test described below.

The compounds of the invention are thus expected to be useful in both the prophylaxis and the treatment of arrhythinias, and in particular atrial and ventricular arrhythmias.

The compounds of the invention are thus indicated in the treatment or prophylaxis of cardiac diseases, or in indications related to cardiac diseases, in which arrhythmias are believed to play a major role, including ischaemic heart disease, sudden heart attack, myocardial infarction, heart failure, cardiac surgery and thromboembolic events.

In the treatment of arrhythmias, compounds of the invention have been found to selectively delay cardiac repolarization and increase refractoriness.

According to a further aspect of the invention, there is provided a method of treatment of an arrhythmia which method comprises administration of a therapeutically effective amount of a compound of the invention to a person suffering from, or susceptible to, such a condition.

Pharmaceutical Preparations

The compounds of the invention will normally be administered orally, subcutaneously, intravenously, intraarterially, transdermally, intranasally, by inhalation, or by any other parenteral route, in the form of pharmaceutical preparations comprising the active ingredient either as a free base or a non-toxic organic or inorganic acid addition salt, in a pharmaceutically acceptable dosage form. Depending upon the disorder and patient to be treated, as well as the route of administration, the compositions may be administered at varying doses.

The compounds of the invention may also be combined with any other drugs useful in the treatment of arrhythmias and/or other cardiovascular disorders. In particular the compounds of the invention may be combined with an anti-coagulant.

When used herein, the term "an anticoagulant" includes references to one a substance selected from the group consisting of aspirin, warfarin, enoxaparin, heparin, low molecular weight heparin, cilostazol, clopidogrel, ticlopidine, tirofiban, abciximab, dipyridamole, plasma protein fraction, human albumin, low molecular weight dextran, hetastarch, reteplase, alteplase, streptokinase, urokinase, dalteparin, filgrastin, immunoglogulin, ginkolide B, hirudins, foropafant, rocepafant, bivalirudin, dermatan sulfate mediolanum, eptilibatide, tirofiban, thrombomodulin, abcxmab, low molecular weight dermatan sulfate-opocrin, eptacog alfa, argatroban, fondaparinux sodium, tifacogin, lepirudin, desirudin, OP2000, roxifiban, parnaparin sodium, human hemoglobin (Hemosol), bovine hemoglobin (Biopure), human hemoglobin (Northfield), antithrombin III, RSR 13, heparin-oral (Emisphere) transgenic antithrombin III, H37695, enoxaparin sodium, mesoglycan, CTC 111, bivalirudin, and any derivatives and/or combinations thereof.

Particular anticoagulants that may be mentioned include aspirin and warfarin.

The term "an anticoagulant" also includes references to thrombin inhibitors. Thrombin inhibitors that may be mentioned include low molecular weight thrombin inhibitors. The term "low molecular weight thrombin inhibitors" will be understood by those skilled in the art, and includes references to any composition of matter (e.g. chemical compound) that inhibits thrombin to an experimentally determinable degree (as determined by in vivo and/or in vitro tests), and which possesses a molecular weight of below about 2,000, preferably below about 1,000.

Preferred low molecular weight thrombin inhibitors include low molecular weight peptide-based, amino acid-based, and/or peptide analogue-based, thrombin inhibitors, as well as derivatives thereof.

The term "low molecular weight peptide-based, amino acid-based, and/or peptide analogue-based, thrombin inhibitors" will be well understood by one skilled in the art to include references to low molecular weight thrombin inhibitors with one to four peptide linkages, and includes those described in the review paper by Claesson in *Blood Coagul. Fibrin.* 5, 411 (1994), as well as those disclosed in U.S. Pat. No. 4,346,078, International Patent Applications WO 93/11152, WO 93/18060, WO 93/05069, WO 94/20467, WO 94/29336, WO 95/35309, WO 95/23609, WO 96/03374, WO 96/06832, WO 96/06849, WO 96/25426, WO 96/32110, WO 97/01338, WO 97/02284, WO 97/15190, WO 97/30708, WO 97/40024, WO 97/46577, WO 98/06740, WO 97/49404, WO 97/11693, WO 97/24135, WO 97/47299, WO 98/01422, WO 98/57932, WO 99/29664, WO 98/06741, WO 99/37668, WO 99/37611, WO 98/37075, WO 99/00371, WO 99/28297, WO 99/29670, WO 99/40072, WO 99/54313, WO 96/31504, WO 00/01704 and WO 00/08014; and European Patent Applications 648 780, 468 231, 559 046, 641779, 185 390, 526 877, 542 525, 195 212, 362 002, 364 344, 530 167, 293 881, 686 642, 669 317, 601 459 and 623 596, the disclosures in all of which documents are hereby incorporated by reference.

In the present application, derivatives of thrombin inhibitors include chemical modifications, such as esters, prodrugs and metabolites, whether active or inactive, and pharmaceutically acceptable salts and solvates, such as hydrates, of any of these, and solvates of any such salt.

Preferred low molecular weight peptide-based thrombin inhibitors include those known collectively as the "gatrans". Particular gatrans which may be mentioned include HOOC—CH$_2$—(R)Cha-Pic-Nag-H (known as inogatran) and HOOC—CH$_2$—(R)Cgl-Aze-Pab-H (known as melagatran) (see International Patent Application WO 93/11152 and WO 94/29336, respectively, and the lists of abbreviations contained therein).

International Patent Application WO 97/23499 discloses a number of compounds which have been found to be useful as prodrugs of thrombin inhibitors. Said prodrugs have the general formula

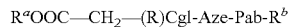

R$^a$OOC—CH$_2$—(R)Cgl-Aze-Pab-R$^b$ wherein R$^a$ represents H, benzyl or C$_{1-10}$ alkyl, R$^b$ (which replaces one of the hydrogen atoms in the amidino unit of Pab-H) represents OH, OC(O)R$^c$ or C(O)OR$^d$, R$^c$ represents C$_{1-17}$ alkyl, phenyl or 2-naphthyl and R$^d$ represents C$_{1-12}$ alkyl, phenyl, C$_{1-3}$ alkylphenyl, or 2-naphthyl. Preferred compounds include R$^a$OOC—CH$_2$—(R)Cgl-Aze-Pab-OH, wherein R$^a$ represents benzyl or C$_{1-10}$ alkyl, e.g. ethyl or isopropyl, especially EtOOC—CH$_2$—(R)Cgl-Aze-Pab-OH. The active thrombin inhibitors themselves are disclosed in WO 94/29336.

According to a further aspect of the invention there is thus provided a pharmaceutical formulation including a compound of the invention in admixture with a pharmaceutically acceptable adjuvant, diluent or carrier.

Suitable daily doses of the compounds of the invention in therapeutic treatment of humans are about 0.005 to 50.0 mg/kg body weight at oral administration and about 0.005 to 15.0 mg/kg body weight at parenteral administration. Preferable ranges of daily doses of the compounds of the invention in therapeutic treatment of humans are about 0.005 to 20.0 mg/kg body weight at oral administration and about 0.005 to 10.0 mg/kg body weight at parenteral administration.

The compounds of the invention have the advantage that they are effective against cardiac arrhythmias.

Compounds of the invention may also have the advantage that they may be more efficacious than, be less toxic than, have a broader range of activity (including exhibiting any combination of class I, class II, class III and/or class IV activity (especially class I and/or class IV activity in addition to class III activity)) than, be more potent than, be longer acting than, produce fewer side effects (including a lower incidence of proarrhythmias such as torsades de pointes) than, be more easily absorbed than, or that they may have other useful pharmacological properties over, compounds known in the prior art.

BIOLOGICAL TESTS

Test A

Primary Electrophysiological Effects In Anaesthetised Guinea Pigs

Guinea pigs weighing between 500 and 1000 g were used. The animals were housed for at least one week before the experiment and had free access to food and tap water during that period.

Anaesthesia was induced by an intraperitoneal injection of pentobarbital (50 to 60 mg/kg) and catheters were introduced into one carotid artery (for blood pressure recording and blood sampling) and into one jugular vein (for drug infusions). Needle electrodes were placed on the limbs for recording of ECGs (lead II). A thermistor was placed in the rectum and the animal was placed on a heating pad, set to a rectal temperature of between 37.5 and 38.5° C.

A tracheotomy was performed and the animal was artificially ventilated with room air by use of a small animal ventilator, set to keep blood gases within the normal range for the species. In order to reduce autonomic influences both vagi were cut in the neck, and 0.5 mg/kg of propranolol was given intravenously, 15 minutes before the start of the experiment.

The left ventricular epicardium was exposed by a left-sided thoracotomy, and a custom-designed suction electrode for recording of the monophasic action potential (MAP) was applied to the left ventricular free wall. The electrode was kept in position as long as an acceptable signal could be recorded, otherwise it was moved to a new position. A bipolar electrode for pacing was clipped to the left atrium. Pacing (1 ms duration, twice the diastolic threshold) was performed with a custom-made constant current stimulator. The heart was paced at a frequency just above the spontaneous sinus rate during 30 s every fifth minute throughout the study.

The MAP signal, the blood pressure signal and the lead II ECG were collected (the sampling frequency was 1000 Hz and each sampling period 10 s) on a personal computer during the last 10 s of each 30 s pacing sequence and the last 10 s of the following min of sinus rhythm. The signals were processed using a custom-designed computer program (Pharm-Lab v 4.0).

The test procedure consisted of two basal control recordings, 3 minutes apart, during both pacing and sinus rhythm.

After the second control recording, the first dose of the test substance was infused in a volume of 0.2 mL/kg into the jugular vein catheter for 30 seconds. Three minutes later, pacing was started and a new recording was made. Five minutes after the previous dose, the next dose of test substance was administered. Six to ten consecutive doses were given during each experiment.

Data Analysis

Of the numerous variables measured in this analysis, three were selected as the most important for comparison and selection of active compounds. The three variables selected were the MAP duration at 75 percent repolarization during pacing, the atrio-ventricular (AV) conduction time (defined as the interval between the atrial pace pulse and the start of the ventricular MAP) during pacing, and the heart rate (defined as the RR interval during sinus rhythm). Systolic and diastolic blood pressure were measured in order to judge the haemodynamic status of the anaesthetised animal. Further, the ECG was checked for arrhythmias and/or morphological changes.

The mean of the two control recordings was set to zero and the effects recorded after consecutive doses of test substance were expressed as percentage changes from this value. By plotting these percentage values against the cumulative dose administered before each recording, it was possible to construct dose-response curves. In this way, each experiment generated three dose-response curves, one for MAP duration, one for AV-conduction time and one for the sinus frequency (RR interval). A mean curve of all experiments performed with a test substance was calculated, and potency values were derived from the mean curve. All dose-response curves in these experiments were constructed by linear connection of the data points obtained. The cumulative dose prolonging the MAP duration by 10% from the baseline was used as an index to assess the class III electrophysiological potency of the agent under investigation ($D_{10}$).

Test B $R^+$-Efflux Assay for Detection of HERG Channel Blockers

The human ether-a-go-go related gene (HERG) encodes the voltage-gated $K^+$ channel underlying the cardiac rapid delayed rectifier current IKr. The IC50 value for HERG channel blockade was determined using a high throughput functional assay based on depolarisation-induced $R^+$-efflux from Chinese hamster ovary cells stably expressing the HERG-channel.

Cells were grown in Ham F12 (Life Technologies 31765-027) supplemented with 10% FBS and 0.6 mg/mL hygromycin B and were routinely passaged twice-weekly. For experimental studies, cells were plated at a density of 15,000 cells/well in Falcon, 384-well tissue culture-treated black-walled clear-bottomed plates and were thereafter incubated overnight at 37° C. in a cell culture incubator.

Following incubating overnight, cell plates were washed and a $Rb^+$-Load buffer (a physiological buffer containing $Rb^+$) was added. Cell plates were then incubated for 3 hours and were thereafter washed. Following this wash, the test compounds were added. The cell plates were then incubated for another 10 minutes and, following this incubation period, external $K^+$ concentration was increased in order to depolarize the cells and activate HERG channels. After a ten minute exposure period to the increased $K^+$ concentration, supernatants were transferred to new microplates for subsequent determination of $Rb^+$ content, using Atomic Absorption Spectrometry analysis.

The basal $Rb^+$ efflux (content of $Rb^+$ (mg/L) in supernatants of wells receiving only wash buffer) was defined as 100% inhibition and the stimulated $Rb^+$ efflux (content of $Rb^+$ (mg/L) in supernatants of wells exposed only to increased external potassium concentration) was defined as 0% inhibition.

Compound activity was expressed as:

$$100 \times \left[1 - \frac{A-B}{C-B}\right]$$

A: $Rb^+$ content in wells receiving test compound + increased external $K^+$.
B: Basal $Rb^+$ efflux.
C: Stimulated $Rb^+$ efflux.

The invention is illustrated by way of the following examples.

EXAMPLES

General Experimental Procedures

Mass spectra were recorded on one of the following instruments: MUX(8)-LCT, ZQ Masspectrometer and Quattro micro, all from Waters Micromass.

LC-MS:

Separation was performed using Agilent 1100 Series Modules or Waters 1525 pump on a ACT (Advanced Chromatography Technologies) ACE C8 3×50 mm 3 µm with gradient elution.

Samples were injected using Waters 2700 Sample Manager.

Mobile Phases:

Generic gradients were applied from 5% to 95% acetonitrile.

Buffers containing 10 mM ammonium acetate or 5 mM ammonium formate /5 mM formic acid were used.

The mass spectra were recorded with a Waters ZQ2000 or Waters ZMD equipped with an electrospray interface, switching positive and negative ionization mode. UV spectra were collected by a Agilent 1100 PDA or Waters 2996 DAD and the evaporative light scattering (ELS) signal by a Sedere Sedex 55 or 75.

Data collection and evaluation were performed using the MassLynx software.

$^1$H NMR and $^{13}$C NMR measurements were performed on a BRUKER ACP 300 and Varian 300, 400, 500 and 600 Mercury, Unity plus and Inova spectrometers, operating at $^1$H frequencies of 300, 400, 500 and 600 MHz respectively and at $^{13}$C frequencies of 75.4, 100.6, 125.7 and 150.9 MHz respectively.

Rotamers may or may not be denoted in spectra depending upon ease of interpretation of spectra. Unless otherwise stated, chemical shifts are given in ppm with the solvent as internal standard.

Synthesis of Intermediates

The following intermediates were not commercially available, and were therefore prepared by the methods described below.

Preparation A

4-{(2S)-3-[7-(2-Aminoethyl)-9-oxa-3,7-diazabicyclo[3.3.1]non-3-yl]-2-hydroxypropoxy}benzonitrile tert-Butyl 2-{7-[(2S)-3-(4-cyanophenoxy)-2-hydroxypropyl]-9-oxa-3,7-di-azabicyclo[3.3.1]non-3-yl}ethylcarbamate (2.9 g, 6.56 mmol; see WO 01/28992) was dissolved in DCM (30 mL). Trifluoroacetic acid (22.2 g, 194.7 mmol) was added and the solution was stirred for 2 h.

The mixture was concentrated under reduced pressure, redissolved in toluene and acetonitrile and concentrated in vacuo again. The product mixture was dissolved in acetonitrile (50 mL) and solid $K_2CO_3$ (9.7 g, 10.2 mmol) was added. The mixture was filtered and concentrated under reduced pressure. The mixture was then redissolved in a mixture of EtOAc and a saturated solution of $NaHCO_3$. The mixture was extracted twice with DCM, the combined organic extracts dried ($Na_2SO_4$) and evaporated to afford 1.6 g (68.7%) of the title compound.

Preparation B

4-{3-[7-(2-Aminoethyl)-9-oxa-3,7-diazabicyclo [3.3.1]non-3-yl]propoxy}-benzonitrile, hydrochloride salt (i) (2-{7-[3-(4-Cyanophenoxy)propyl]-9-oxa-3,7-diazabicyclo[3.3.1]non-3-yl}ethyl)carbamic acid tert-butyl ester 4-[3-(9-Oxa-3,7-diazabicyclo[3.3.1]non-3-yl)propoxy] benzonitrile (6.5 g, 0.0226 mol; see WO 01/28992) and tert-butyl 2-bromoethylcarbamate (6 g, 0.0271 mol; see WO 01/28992) were dissolved in 80 mL of dry acetonitrile. Anhydrous potassium carbonate (4.68 g, 0.034 mol) was added and the mixture was stirred at 60° C. overnight. A further portion of tert-butyl 2-bromoethylcarbamate (2.53 g, 0.0113 mol) was added and the reaction heated at 65° C. overnight. The reaction mixture was then filtered and the filtrate concentrated under reduced pressure. The product was purified by column chromatography using methanol-chloroform as eluent to give the sub-title compound (4.5 g) as a yellow solid.

(ii) 4-{3-[7-(2-Aminoethyl)-9-oxa-3,7-diazabicyclo [3.3.1]non-3-yl]-propoxy}benzonitrile, hydrochloride salt (2-{7-[3-(4-Cyanophenoxy)propyl]-9-oxa-3,7-diazabicyclo[3.3.1]non-3-yl}-ethyl)carbamic acid tert-butyl ester (4.5 g, 0.0104 mol; see step (i) above) was added to a solution of HCl in dioxane. The reaction was stirred at room temperature for 2 h, after which the reaction mixture was filtered and the resultant solid washed with dioxane, then diethyl ether and dried to give the title compound (3.89 g) as a white solid.

Preparation C

{2-[9-oxa-3,7-diazabicyclo[3.3.1]non-3-yl] ethyl}tert-butylcarbamate, hydrochloride salt (i) 2-Bromoethyl tert-butylcarbamate To a cooled solution of triphosgene (76 g, 0.256 mol, 0.75 eq.) in dry DCM (150 mL) was added, dropwise at 0° C. over a period of 3 hrs under a $N_2$ atmosphere, a mixture of tert-butylamine (25 g, 0.3418 mol, 1.0 eq.), DMAP (2.08 g, 0.017 mol, 0.05 eq.) and triethylamine (67.1 g, 0.6836 mol, 2.0 eq.) in dry DCM (100 mL). After addition of the mixture was complete, the reaction mixture was stirred at RT for 12 hrs. The reaction mixture was cooled to 0° C. and 2-bromoethanol (106.8 g, 0.854 mol, 2.5 eq.) was added. The reaction mixture was then stirred at RT for 6 hrs, before being diluted with water and extracted with DCM. The combined organic layers were washed with brine, dried over anhydrous $Na_2SO_4$, and then concentrated under reduced pressure. The resulting residue was distilled under reduced pressure to yield carbamate the sub-title compound as a colourless liquid. Yield: 28 g.

(ii) {2-[7-Benzyl-9-oxa-3,7-diazabicyclo[3.3.1]non-3-yl]ethyl}tert-butylcarbamate A mixture of 3-benzyl-9-oxa-3,7-diazabicyclo[3.3.1] nonane dihydrochloride (8 g, 0.0275 mol, 1.0 eq.; see WO 01/28992), 2-bromoethyl tert-butylcarbamate (9.23 g, 0.0412 g, 1.5 eq.) and fused $K_2CO_3$ (18.96 g, 0.1375 mol, 5.0 eq.) in dry acetonitrile (120 mL) was stirred at 70° C. overnight under a $N_2$ atmosphere. The reaction mixture was cooled to RT, filtered and concentrated under reduced pressure. The resulting resiude was purified by column chromatography over silica gel (using 92:8 DCM:methanol as final eluent) to yield the sub-title compound (5 g, 43%).

(iii) {2-[9-oxa-3,7-diazabicyclo[3.3.1]non-3-yl] ethyl}tert-butylcarbamate, hydrochloride salt {2-[7-Benzyl-9-oxa-3,7-diazabicyclo[3.3.1]non-3-yl] ethyl}tert-butyl-carbamate (5 g; see step (ii) above) was dissolved in dry dioxane (50 mL) and the resulting solution cooled to 0° C. To this solution was added, dropwise with continuous stirring, 100 mL of dry dioxane saturated with HCl. The reaction mixture was stirred at RT for 1 hr. Dioxane was decanted carefully and the hygroscopic solid precipitate was washed with dry ether twice and then dried under vacuum to yield the dihydrochloride salt as a white solid. This salt was dissolved in dry methanol (100 mL), to which was then added 10% palladium on carbon. The resulting mixture was stirred under a $H_2$ atmosphere for 12 hrs. The reaction mixture was filtered through Celite®, the filtrate concentrated under reduced pressure and the resulting solid dried under high vacuum to provide the title compound as a pale yellow solid. Yield: 3.8 g.

Preparation D

1-[3-(9-Oxa-3,7-diazabicyclo[3.3.1 ]non-3-yl)propanoyl]indoline-5-carbonitrile, hydrochloride salt (i) 5-Bromo-2,3-dihydro-1H-indole $NaBH_3CN$ (19.3 g, 0.3061 mol) was added in 3 portions to a cooled (15° C.) solution of 5-bromoindole (20 g, 0.10 mol) in glacial acetic acid (500 mL) and stirred for 2 h at this same temperature. The reaction mixture was quenched with water, cooled and basified with a sodium hydroxide pellet. It was then extracted with diethyl ether. The organic layer was washed with water and brine, dried over sodium sulfate, concentrated and purified by column chromatography over silica gel to give the sub-title compound as a pale yellow solid. Yield: 20 g.

(ii) 5-Bromo-1-(trifluoroacetyl)indoline

5-Bromo-2,3-dihydro-1H-indole (20 g, 0.1010 mol; see step (i) above) was taken in (100 mL) of DCM and cooled to 0° C. Trifluoroacetic anhydride (42.42 g, 0.2020 mol) was added dropwise to the reaction mixture, which was then stirred for 30 min. The reaction mixture was quenched with water and extracted with ethyl acetate. The organic layer was washed with water and brine, dried over sodium sulfate, concentrated and purified by column chromatography over silica gel to give the sub-title compound as a white solid. Yield: 28 g.

(iii) 1-(2,2,2-Trifluoroacetyl)-2,3-dihydro-1H-indole-5-carbonitrile 1-(5-Bromo-2,3-dihydro-1H-indol-1-yl)-2,2,2-trifluoroethanone (19 g, 0.0646 mol; see step (ii) above) was dissolved in DMF (50 mL). CuCN (8.68 g, 0.0969 mol) was then added and the reaction mixture was stirred at 160° C. for 4 days, before being cooled to RT, diluted with water and extracted with ethyl acetate. The organic layer was washed with water and brine, dried over sodium sulfate then concentrated under reduced pressure. The resulting residue was purified by column chromatography to give the sub-title compound as a white solid. Yield: 13 g.

(iv) 2,3-Dihydro-1H-indole-5-carbonitrile 1-(2,2,2-Trifluoroacetyl)-2,3-dihydro-1H-indole-5-carbonitrile (13 g, 0.0542 mol; see step (iii) above) was dissolved in THF (100 mL), to which 1% NaOH was then added. After stirring for 5 h at RT, the reaction mixture was extracted with ethyl acetate. The organic layer was washed with water and brine, dried over sodium sulfate and solvent was evaporated to provide the sub-title compound as a pale yellow solid. Yield: 8 g.

(v) 1-(3-Chloropropionyl)-2,3-dihydro-1H-indole-5-carbonitrile

To a solution of 2,3-dihydro-1H-indole-5-carbonitrile (8 g, 0.0556 mol; see step (iv) above) in DCM (50 mL) at 0° C. was added N,N-dimethylaniline (13.5 g, 0.1112 mol) followed by 2-chloropropionyl chloride (8.46 g, 0.0667 mol). The reaction mixture was stirred for 3 h before being diluted with water and extracted with DCM. The organic layer was washed with water and brine, dried over sodium sulfate and then concentrated under reduced pressure. The resulting residue was purified by column chromatography over silica gel to yield the sub-title compound as a pale yellow solid. Yield: 10.5 g.

(vi) tert-Butyl 7-[3-oxo-3-(5-cyano-2,3-dihydro-1H-indol-1-yl)propyl]-9-oxa-3,7-diazabicyclo[3.3.1]nonane-3-carboxylate 1-(3-Chloropropionyl)-2,3-dihydro-1H-indole-5-carbonitrile (3.07 g, 0.031 mol; see step (v) above), 9-oxa-3,7-diazabicyclo[3.3.1]nonane-3-carboxylic acid tert-butyl ester (3 g, 0.031 mol; see WO 01/28992) and potassium carbonate (6.43 g, 0.0465 mol) were taken in dry acetonitrile (30 mL) and stirred at 60° C. overnight under a nitrogen atmosphere. The reaction mixture was filtered and concentrated under reduced pressure to provide a crude product. This product was then purified by column chromatography using methanol in DCM as eluent to yield the sub-title compound as pale yellow solid. Yield: 5 g.

(vii) 1-[3-(9-Oxa-3,7-diazabicyclo[3.3.1]non-3-yl) propanoyl]indoline-5-carbonitrile, hydrochloride salt tert-Butyl 7-[3-oxo-3-(5-cyano-2,3-dihydro-1H-indol-1-yl)propyl]-9-oxa-3,7-diazabicyclo[3.3.1]nonane-3-carboxylate (5 g, 0.017 mol; see step (vi) above) was taken up in 50 mL of dioxane that was saturated with HCl gas. The mixture was then stirred for 1 h under nitrogen atmosphere at RT. The resulting solid was filtered and washed with ether and then dried under vacuum to yield 4.42 g of the title compound as an off white solid.

Preparation E

4-Cyano-N-[2-(9-oxa-3,7-diazabicyclo[3.3.1]non-3-yl)ethyl]benzene-sulfonamide (i) N-(2-Bromoethyl)-4-cyanobenzenesulfonamide To an ice cooled solution of 2-bromoethylamine hydrogenbromide (12.2 g, 0.0595 mol) in dry dichloromethane (100 mL) was added triethylamine and the mixture stirred for 15 min. 4-Cyanobenzenesulfonyl chloride (10 g, 0.0486 mol) in dichloromethane was added, dropwise. Stirring was continued at RT for 1 h. The reaction mixture was diluted with dichloromethane, washed with water, followed by brine, then dried over sodium sulfate. Solvents were evaporated and the residue crystallized from petroleum ether to give 12.5 g of the sub-title compound as a pale yellow solid.

(ii) 7-[2-(4-Cyanobenzenesulfonylamino)ethyl]-9-oxa-3,7-diazabicyclo-[3.3.1]nonane-3-carboxylic acid tert-butyl ester A suspension of N-(2-bromoethyl)-4-cyanobenzenesulfonamide (5 g, 0.017 mol; see step (i) above), 9-oxa-3,7-diaza-bicyclo[3.3.1]nonane-3-carboxylic acid tert-butyl ester (3.96 g, 0.0173 mol; see WO 01/28992) and potassium carbonate (3.6 g, 0.025 mol) in acetonitrile (50 mL) was stirred at 60° C. overnight. The reaction mixture was filtered and the solvent concentrated under reduced pressure to yield the crude product, which was purified by column chromatography (using methanol in chloroform as the eluent) to yield (5 g) of the sub-title compound as pale yellow solid.

(iii) 4-Cyano-N-[2-(9-oxa-3,7-diazabicyclo[3.3.1] non-3-yl)ethyl]benzenesulfonamide 7-[2-(4-Cyanobenzenesulfonylamino)ethyl]-9-oxa-3,7-diaza-bicyclo[3.3.1]-nonane-3-carboxylic acid tert-butyl ester (5 g; see step (ii) above) was taken up in 30 mL of dioxane that was saturated with HCl gas. The mixture was stirred for 1 h before the dioxane was decanted off and the remaining solid was washed with diethyl ether, yielding the HCl salt of the title compound. This salt was then taken up in DCM-NaHCO$_3$ (200 mL, 1:1) and the resulting mixture stirred for 1 h at RT. The compound was extracted with dichloromethane, washed with water, brine and dried over sodium sulfate. Solvent evaporation under reduced pressure yielded 3.4 g of the title compound as white solid.

Preparation F

4-{2-[7-(2-Aminoethyl)-9-oxa-3,7-diazabicyclo [3.3.1]non-3-yl]ethoxy}-benzonitrile, trihydrochloride salt (i) (2-{7-[2-(4-Cyanophenoxy)ethyl]-9-oxa-3,7-diazabicyclo[3.3.1]non-3-yl}ethyl)carbamic acid tert-butyl ester, diacetate salt

[2-(9-Oxa-3,7-diazabicyclo[3.3.1]non-3-yl)ethyl]carbamic acid tert-butyl ester, 2,4,6-trimethylbenzenesulfonic acid salt (10.1 g, 21.3 mmol; see WO 02/83690) was mixed with 4-(2-bromoethoxy)benzonitrile (5.37 g, 23.7 mmol) and K$_2$CO$_3$ (7.44 g, 74.6 mmol) in acetonitrile (200 mL). The mixture was refluxed overnight before further K$_2$CO$_3$ (2.88 g, 211 mmol) was added and the mixture refluxed for an additional 8 h. The reaction mixture was filtered and evaporated. The product obtained thereby was purified by chromatography (kromasil C8, 100×500 mm, CH$_3$CN/NH$_4$OAc-buffer with 0.2% formic acid; Gradient 40-80% acetonitrile). The product was freeze-dried and the diacetate was isolated. (10.8 g, 94.5% yield.)

(ii) 4-{2-[7-(2-Aminoethyl)-9-oxa-3,7-diazabicyclo [3.3.1]non-3-yl]ethoxy}-benzonitrile, trihydrochloride salt Hydrochloric acid (140 mmol, 35 mL of a 4 M solution in dioxane) was added to an ice-cooled slurry of the diacetate salt of (2-{7-[2-(4-cyanophenoxy)ethyl]-9-oxa-3,7-diazabicyclo[3.3.1]non-3-yl}ethyl)carbamic acid tert-butyl ester (10.75 g, 20 mmol; see step (i) above) in dioxane (50 mL). The reaction mixture was stirred at RT overnight. Another 65 mL (260 mmol) of 4 M HCl solution was added, after which the reaction mixture was stirred for three hours and then evaporated. The residue was dissolved in water and washed with diethyl ether. Freeze-drying of the aqueous phase gave 8.3 g (97%) the title compound as a white solid.

$^1$H NMR (D$_2$O): δ 2.78 (m, 4 H), 3.22 (m, 4 H), 3.65 (m, 2 H), 3.71 (t, J=4.6 Hz, 2 H), 3.91 (m, 2 H), 4.36 (bs, 2 H), 4.57 (t, J=4.6 Hz, 2 H), 7.16 (d, J=9 Hz), 7.79 (d, J=9 Hz).

$^{13}$C NMR (D$_2$O): δ 33.2, 52.4, 53.0, 53.4, 53.9, 59.2, 63.7, 101.4, 113.1, 117.6, 132.3, 158.5.

Preparation G 4-(2-Bromoethyl)-1,2-bis(difluoromethoxy)benzene (i) 3,4-Bis(difluoromethoxy)benzaldehyde 3,4-Dihydroxybenzaldehyde (20 g, 0.144 mol) and potassium carbonate (40 g, 0.2898 mol) were taken up in dry DMF (1 L) and cooled to –78° C. A Dewar condenser was fitted and freon gas (CHClF$_2$) was passed through the reaction mixture for 1 h. The reaction mixture was stirred at 85° C. overnight. Solvent was evaporated under reduced pressure and the residue purified by column chromatography over silica gel (using petroleum ether in ethyl acetate as eluent) to yield the sub-title compound as a pale yellow liquid. Yield: 11 g.

(ii) Methyl triphenylphosphonium iodide

To a solution of triphenylphosphine (30 g, 0.114 mol) in benzene (200 mL) was added methyl iodide (11 ml, 0.1756 mol) dropwise, and the solution stirred at room temperature for 15 min under a nitrogen atmosphere. The sub-title compound formed as a colourless solid, which was filtered and then dried. Yield: 30 g.

(iii) 1,2-Bis(difluoromethoxy)-4-vinylbenzene

Potassium tert-butoxide (6.7 g, 0.0683 mol) was taken in dry THF (25 mL) and stirred at 0° C. under a nitrogen atmosphere for 15 min. Methyl triphenylphosphonium iodide (27.6 g, 0.0683 mol; see step (ii) above) was then added, followed by 3,4-bis(difluoromethoxy)benzaldehyde (8 g, 0.034 mol; see step (i) above). The reaction mixture was then stirred for 1 h at RT, before being quenched with water. The organic solvents were evaporated under reduced pressure and the aqueous layer extracted with dichloromethane. Evaporation of the solvents followed, by chromatography of the residue over silica gel (using petroleum ether in ethyl acetate as eluent) afforded the sub-title compound as a pale yellow liquid. Yield: 6.5 g (iv) 2-[3,4-Bis(difluoromethoxy)phenyl]ethanol To a solution of 1,2-bis(difluoromethoxy)-4-vinylbenzene (10 g, 0.0431 mol; see step (iii) above) in 25 mL of THF was added, dropwise, borane-methyl sulfide complex (10 mmol; 10 mL of a 1 M solution in THF). The resulting mixture was stirred at 60° C. for 1 h, before being cooled to RT. Excess borane was decomposed by adding few drops of water and the resultant mixture refluxed for 1 h with 2 M NaOH (100 mL) 50% H$_2$O$_2$ (87 mL). The mixture was then extracted with dichloromethane, washed with water and then brine, and dried over sodium sulfate. Solvent evaporation under reduced pressure gave the sub-title compound as a pale yellow liquid. Yield: 6 g.

(v) 4-(2-Bromoethyl)-1,2-bis(difluoromethoxy)benzene

2-[3,4-Bis(difluoromethoxy)phenyl]ethanol (6 g, 0.024 mol; see step (iv) above) and triphenylphosphine (12.6 g, 0.048 mol) were taken up in dichloromethane (100 mL) and cooled to 0° C. CBr$_4$ (15.9 g, 0.048 mol) in dichloromethane was added dropwise, and the mixture stirred at RT overnight under a nitrogen atmosphere. The reaction mixture was filtered, the filtrate concentrated under reduced pressure and the residue purified by column chromatography over silica gel (using 20% ethyl acetate in petroleum ether as eluent) to give the title compound as a yellow liquid. Yield 5.2 g.

Preparation H

4-Fluoro-N-[2-(9-oxa-3,7-diaza-bicyclo[3.3.1]non-3-yl)-ethyl]-benzenesulfonamide (i) N-(2-Bromo-ethyl)-4-fluoro-benzenesulfonamide 4-Fluoro benzene sulfonyl chloride (8 g, 0.0411 mol) was added dropwise at 0° C. to a solution of 2-bromoethylamine hydrogen bromide (10.27 g, 0.0501 mol) and triethyl amine (14.3 ml, 0.1029 mol) in dry dichloromethane (100 ml) and stirred at room temperature for 1 h under nitrogen atmosphere. The reaction mixture was diluted with water and extracted with ethyl acetate. Organic layer was washed with water and brine and dried over sodium sulfate. Solvent evaporation under reduced pressure afforded the sub-title product as a liquid. Yield: 11 g (ii) 7-[2-(4-Fluoro-benzenesulfonylamino)-ethyl]-9-oxa-3,7-diaza-bicyclo[3.3.1]nonane-3-carboxylic acid tert-butyl ester A suspension of N-(2-Bromo-ethyl)-4-fluoro-benzenesulfonamide (7 g, 0.0179 mol; see step (i) above) and 9-oxa-3,7-diaza-bicyclo[3.3.1]nonane-3-carboxylic acid tert-butyl ester (11.2 g, 0.159 mol; see WO 01/28992) and K$_2$CO$_3$ (9.7 g, 0.0798 mol) in dry acetonitrile (70 ml) was stirred at 60° C. overnight under nitrogen atmosphere. The reaction mixture was partitioned between brine and ethyl acetate. Organic layer was washed with brine and dried over sodium sulfate. Solvent evaporation under reduced pressure followed by column chromatography over silica gel using 7% ethyl acetate in petroleum ether as eluent afforded the sub-title compound as a solid. Yield: 4 g (iii) 4-Fluoro-N-[2-(9-oxa-3,7-diaza-bicyclo[3.3.1] non-3-yl)-ethyl]-benzenesulfonamide , hydrochloride salt HCl in dioxane (50 ml) was added to a solution of 7-[2-(4-Fluoro-benzenesulfonylamino)-ethyl]-9-oxa-3,7-diaza-bicyclo[3.3.1]nonane-3-carboxylic acid tert-butyl ester (4 g; see step (ii) above) in dry dioxane (50 ml) at RT and the reaction mixture was stirred at RT for 1 h. Dioxane was decanted, precipitated solid was washed with dry diethyl ether (three times) and dried under vacuum to give the title compound as pale yellow solid. Yield: 3.55 g Preparation I

4-Cyano-N-methyl-N-[2-(9-oxa-3,7-diaza-bicyclo[3.3.1]non-3-yl)-ethyl]-benzenesulfonamide, hydrochloride salt

(i) 4-Cyano-N-methyl-N-(2-oxo-ethyl)-benzenesulfonamide

4-Cyanobenzenesulfonyl chloride (6 g, 0.0297 mol) in 50 ml of dry DCM was added at 0° C. to a solution of N-methylethanolamine (2.67 g, 0.0356 mol) and triethylamine (7.49 g, 0.0742 mol) in dry dichloromethane (75 ml) under nitrogen atmosphere and stirred at RT for 2 h. The reaction mixture was quenched with water and extracted with dichloromethane. Organic layer was washed with water and brine and dried over sodium sulfate. Solvent evaporation under reduced pressure afforded crude product as solid. This solid was then washed with petroleum ether (three times) and dried under vacuum to give the sub-title compound (5.18 g) as white solid.

(ii) 4-Cyano-N-methyl-N-(2-oxo-ethyl)-benzenesulfonamide

Dry DMSO (5.03 g, 0.0465 mol) was added to a solution of oxalyl chloride (4.1 g, 0.0323 mol) in dry DCM (100 ml) and stirred at RT for 30 min under nitrogen atmosphere.

4-Cyano-N-methyl-N-(2-oxo-ethyl)-benzenesulfonamide (5.17 g, 0.0215 mol; see step (i) above) in dry DCM (30 ml) was added at RT and stirring continued at RT for 2 h. The reaction mixture was quenched with triethylamine (10.85 g) at −78° C. and slowly warmed to RT. 10% Citric acid was added and the compound was extracted with dichloro methane. The combined organic layer was washed with water and brine and dried over sodium sulfate. Solvent evaporated under reduced pressure to give the sub-title compound (4.97 g) as yellow oil. This was taken for next step with out further purification.

(iii) 7-{2-[(4-Cyano-benzenesulfonyl)-methyl-amino]-ethyl}-9-oxa-3,7-diaza-bicyclo[3.3.1]nonane-3-carboxylic acid tert-butyl ester A mixture of step (ii) product 4-Cyano-N-methyl-N-(2-oxo-ethyl)-benzenesulfonamide (4.97 g), and 9-oxa-3,7-diaza-bicyclo[3.3.1]nonane-3-carboxylic acid tert-butyl ester (4.95 g; see WO 01/28992) and acetic acid (1.7 ml) in dry dichloromethane (50 ml) was stirred at RT for 3 h and then cooled to 0° C. NaBH$_3$CN (1.96 g, 0.0312 mol) was added and stirring continued at RT overnight under nitrogen atmosphere. The reaction mixture was quenched with water, extracted with dichloromethane, washed with water and brine and dried over sodium sulfate. Solvent evaporated under reduced pressure and the residue was purified by column chromatography over silica gel using 28% ethyl acetate in petroleum ether eluent to give the sub-title compound (2.2 g) as a liquid.

(iv): 4-Cyano-N-methyl-N-[2-(9-oxa-3,7-diaza-bicyclo[3.3.1]non-3-yl)-ethyl]-benzenesulfonamide, hydrochloride salt Step (iii) product 7-{2-[(4-Cyano-benzenesulfonyl)-methyl-amino]-ethyl}-9-oxa-3,7-diaza-bicyclo[3.3.1]nonane-3-carboxylic acid tert-butyl ester (2.2 g) was dissolved in dioxane (10 ml) and to which HCl in dioxane (saturated, 20 ml) was added drop by drop at RT under nitrogen atmosphere. Solvent was decanted, the precipitated solid was washed with dry diethyl ether (three times) and dried under vacuum to yield the title compound (2 g) as white powder.

Preparation J

4-{2-[7-(3-Amino-propyl)-9-oxa-3,7-diaza-bicyclo[3.3.1]non-3-yl]-ethoxy}-benzonitrile

(i) (3-{7-[2-(4-Cyano-phenoxy)-ethyl]-9-oxa-3,7-diaza-bicyclo[3.3.1]non-3-yl}-propyl)-carbamic acid tert-butyl ester A suspension of 4-[2-(9-Oxa-3,7-diaza-bicyclo[3.3.1]non-3-yl)-ethoxy]-benzonitrile (6.5 g, 0.02 mol, see WO 01/28992), (3-Bromo-propyl)-carbamic acid tert-butyl ester (6.0 g, 0.025 mol) and dry K$_2$CO$_3$ (13.08 g, 0.0946 mol) in 40 ml of dry acetonitrile was stirred at 60° C. overnight under N$_2$ atmosphere. The reaction mixture was filtered through celite and the filtrate was concentrated under reduced pressure. The residue was purified by column chromatography over silica gel using 20% ethyl acetate in petroleum ether as eluent to yield sub-title compound (3.5 g) as a liquid.

(ii) 4-{2-[7-(3-Amino-propyl)-9-oxa-3,7-diaza-bicyclo[3.3.1]non-3-yl]-ethoxy}-benzonitrile Dioxane (15 ml, saturated with HCl gas) was added to a solution of (3-{7-[2-(4-Cyano-phenoxy)-ethyl]-9-oxa-3,7-diaza-bicyclo[3.3.1]non-3-yl}-propyl)-carbamic acid tert-butyl ester (3.5 g, from step (i) above) in 5 ml of dry dioxane and stirred for 1 h at RT under nitrogen atmosphere. Dioxane was decanted, precipitated solid was filtered and washed with dry diethyl ether (3 times) and dried under vacuum to give HCl salt of the title compound (1.7 g) as white powder.

Preparation K

4-{3-[7-(3-Amino-propyl)-9-oxa-3,7-diaza-bicyclo[3.3.1]non-3-yl]-propoxy}-benzonitrile hydrochloric acid salt

(i) (3-{7-[3-(4-Cyano-phenoxy)-propyl]-9-oxa-3,7-diaza-bicyclo[3.3.1]non-3-yl}-propyl)-carbamic acid tert-butyl ester The sub-title compound was made in analogy with preparation J (i) above using 4-[3-(9-Oxa-3,7-diaza-bicyclo[3.3.1]non-3-yl)-propoxy]-benzonitrile in place of 4-[2-(9-Oxa-3,7-diaza-bicyclo[3.3.1]non-3-yl)-ethoxy]-benzonitrile (see WO 01/28992).

(ii) 4-{3-[7-(3-Amino-propyl)-9-oxa-3,7-diaza-bicyclo[3.3.1]non-3-yl]-propoxy}-benzonitrile hydrochloric acid salt (3-{7-[3-(4-Cyano-phenoxy)-propyl]-9-oxa-3,7-diaza-bicyclo[3.3.1]non-3-yl}-propyl)-carbamic acid tert-butyl ester (3.5 g) from step (i) above was taken in 25 ml of dioxane (saturated with HCl gas) and stirred at room temperature for 30 min under nitrogen atmosphere. Dioxane was decanted, the solid was washed with diethyl ether (3 times) and dried under vacuum to yield (2.8 g) of the title compound as white powder.

Preparation L

4-Cyano-N-[3-(9-oxa-3,7-diaza-bicyclo[3.3.1]non-3-yl)-propyl]-benzenesulfonamide hydrochloric salt (i) N-(3-Bromo-propyl)-4-cyano-benzenesulfonamide 4-Cyanobenzenesulfonyl chloride (5 g, 0.0248 mol) was added dropwise to a solution of 3-bromopropylamine hydrobromide (6.61 g, 0.0302 mol) and triethylamine (6.26 g, 0.062 mol) in dry dichloromethane (50 ml) at 0° C. and stirred at room temperature overnight under nitrogen atmosphere. The reaction was quenched with water and extracted with dichloromethane. The organic layer was washed with water, brine and dried over sodium sulfate.

Solvent evaporation under reduced pressure afforded the sub-title compound (6.39 g) as a solid. This was used in the next step without further purification (ii) 7-[3-(4-Cyano-benzenesulfonylamino)-propyl]-9-oxa-3,7-diaza-bicyclo[3.3.1]nonane-3-carboxylic acid tert-butyl ester A suspension of N-(3-Bromo-propyl)-4-cyano-benzenesulfonamide (6.39 g, 0.021 mol; see step (i) above), 9-oxa-3,7-diaza-bicyclo[3.3.1]nonane-3-carboxylic acid tert-butyl ester (4.32 g, 0.0189 mol see WO 01/28992) and dry $K_2CO_3$ (10.16 g, 0.0735 mol) in dry acetonitrile (70 ml) was stirred at 60° C. overnight under $N_2$ atmosphere. The reaction mixture was filtered through celite and filtrate was concentrated under reduced pressure. The residue was purified by column chromatography over silica gel using 50% ethyl acetate in petroleum ether, as eluent to give the sub-title compound (4.29 g) as a solid.

(iii) 4-Cyano-N-[3-(9-oxa-3,7-diaza-bicyclo[3.3.1]non-3-yl)-propyl]-benzenesulfonamide hydrochloric acid salt 7-[3-(4-Cyano-benzenesulfonylamino)-propyl]-9-oxa-3,7-diaza-bicyclo[3.3.1]nonane-3-carboxylic acid tert-butyl ester (4.29 g, see step (ii) above) was taken in 20 ml of dioxane, 40 ml of diethylether (saturated with HCl gas) was added and stirred for 1 h at RT under nitrogen atmosphere. Solvent was decanted. The solid was washed with dry diethylether (4 times) and dried under vacuum to give the title compound (5.3 g) as a white solid.

Preparation M

4-[7-(3-Amino-propyl)-9-oxa-3,7-diaza-bicyclo[3.3.1]non-3-lmethyl]-benzonitrile hydrochloric acid salt (i) 7-(4-Cyano-benzyl)-9-oxa-3,7-diaza-bicyclo[3.3.1]nonane-3-carboxylic acid tert-butyl ester A suspension of 4-bromomethylbenzonitrile (10 g, 0.054 mol), 9-oxa-3,7-diaza-bicyclo[3.3.1]nonane-3-carboxylic acid tert-butyl ester (11.5 g, 0.0439 mol; see WO 01/28992) and dry $K_2CO_3$ (21.2 g, 0.153 mol) in 200 ml of dry acetonitrile was stirred at 60° C. overnight under $N_2$ atmosphere. The reaction mixture was filtered through celite and filtrate was concentrated under reduced pressure. The residue was purified by column chromatography over silica gel using 10% ethyl acetate in petroleum ether as eluent to yield (10 g) of the sub-title compound as colorless liquid.

(ii) 4-(9-Oxa-3,7-diaza-bicyclo[3.3.1]non-3-ylmethyl)-benzonitrile, hydrochloride 7-(4-Cyanobenzyl)-9-oxa-3,7-diaza-bicyclo[3.3.1]nonane-3-carboxylic acid tert-butyl ester from step (i) above (10 g) was taken in 15 ml of dioxane (saturated with HCl gas) and stirred for 1 h at RT under nitrogen atmosphere. Dioxane was decanted, the precipitated solid was filtered, washed with dry diethyl ether (4 times) and dried under vacuum to give HCl salt of the sub-title compound (7.5 g) as a powder. This was directly taken for next step without further purification.

(iii) {3-[7-(4-Cyano-benzyl)-9-oxa-3,7-diaza-bicyclo[3.3.1]non-3-yl]-propyl}-carbamic acid tert-butyl ester A suspension of 4-(9-Oxa-3,7-diaza-bicyclo[3.3.1]non-3-yl-methyl)-benzonitrile hydrochloride (6.8 g, 0.021 mol; from step (ii) above), (3-Bromopropyl)-carbamic acid tert-butyl ester (3.93 g, 0.017 mol) and dry $K_2CO_3$ (8.24 g, 0.059 mol) in 27 ml of dry acetonitrile was stirred at 60° C. overnight under $N_2$ atmosphere. The reaction mixture was filtered through celite and filtrate was concentrated under reduced pressure to give (7.5 g) of the sub-title compound as pale a liquid.

(iv) 4-[7-(3-Amino-propyl)-9-oxa-3,7-diaza-bicyclo[3.3.1]non-3-ylmethyl]-benzonitrile hydrochloride {3-[7-(4-Cyano-benzyl)-9-oxa-3,7-diaza-bicyclo[3.3.1]non-3-yl]-propyl}-carbamic acid tert-butyl ester (7 g from step (iii) above) was taken in 50 ml of dioxane (saturated with HCl gas) and stirred for 1 h at RT under nitrogen atmosphere. Dioxane was decanted, the precipitated solid was filtered and washed with dry diethylether (4 times) and dried under vacuum to give the title compound (6.5 g) as a powder.

Preparation N

4-{2-[7-(2-Amino-ethyl)-9-oxa-3,7-diaza-bicyclo[3.3.1]non-3-yl]-ethoxy}-3-fluoro-benzonitrile hydrochloric acid salt (i) 4-Bromo-2-fluorophenol Bromine (68.7 ml, 1.339 mol) dissolved in acetic acid (300 ml) was added drop by drop to a cooled solution of 2-fluorophenol (150 g, 1.339 mol) in acetic acid (1300 ml) and the reaction mixture was stirred at room temperature overnight. The reaction mixture was quenched with aq. sodium bisulfite solution and extracted with dichloromethane. The organic layer was washed with water and brine and dried over sodium sulfate. Solvent evaporation under reduced pressure afforded 4-bromo-2-fluorophenol (210 g) as a liquid. This was directly taken for next step without further purification.

(ii) 4-Bromo-2-fluoro-1-methoxybenzene

Methyl iodide (182.1 ml, 1.319 mol) was added at 0° C. to a well stirred suspension of 4-bromo-2-fluorophenol (210 g, 1.099 mol, from step (i) above ) and $K_2CO_3$ (303.92 g, 2.19 mol) in dry acetone (1.7 L) and stirring continued at 60° C. for two days under nitrogen atmosphere. The reaction mixture was filtered and the solvent was concentrated under reduced pressure to yield 4-bromo-2-fluoro-anisole (225 g) as a liquid. This was directly taken for next step without further purification.

(iii) 3-Fluoro-4-methoxybenzonitrile

A mixture of 4-Bromo-2-fluoro-1-methoxybenzene (107 g, 0.5244 mol, from step (ii) above), CuCN (70.4 g, 0.7866 mol) in dry DMF (150 ml) was stirred at 120° C. overnight. The reaction mixture was cooled to room temperature, diluted with water and extracted with ethyl acetate. Organic layer was washed with water and brine and dried over sodium sulfate. Solvent evaporation under reduced pressure followed by column chromatography over silica gel using 3% ethyl acetate in petroleum ether gave the sub-title compound (24.4 g) as a solid.

(iv) 3-Fluoro-4-hydroxy-benzonitrile $BBr_3$ (23 ml, 0.242 mol) was added to 3-Fluoro-4-methoxy-benzonitrile (24.4 g, 0.16 mol) in dichloromethane (200 ml) at −78° C. and stirring continued overnight at room temperature. Another portion of $BBr_3$ (23 ml, 0.242 mol) was added at −78° C. and stirring continued at RT for 2 days under nitrogen atmosphere. The reaction mixture was quenched with ice water and extracted with dichloromethane. Organic layer was washed with water and brine, and dried over sodium sulfate. Solvent evaporation under reduced pressure gave 20 g of the sub-title compound as a solid. This was taken for next step without further purification.

(v) 4-(2-Bromo-ethoxy)-3-fluorobenzonitrile

A suspension of 3-fluoro-4-hydroxybenzonitrile (20 g, 0.1459 mol, from step (iv) above), anhydrous. $K_2CO_3$ (40.33 g, 0.2918 mol) and 1,2-dibromo ethane (76.8 ml, 0.8754 mol) in dry DMF (150 ml) was stirred at 60° C. for 5 days under nitrogen atmosphere. The reaction mixture wasfiltered through celite and solvent evaporated under reduced pressure. The residue was purified by column chromatography over silica gel using 2% ethyl acetate in petroleum ether, as eluent to yield the sub-title compound (21.6 g) as a solid.

(vi) 7-[2-(4-Cyano-2-fluoro-phenoxy)-ethyl]-9-oxa-3,7-diaza-bicyclo[3.3.1]nonane-3-carboxylic acid tert-butyl ester A suspension of 4-(2-Bromo-ethoxy)-3-fluoro-benzonitrile (21.6 g, 0.0885 mol, from step (v) above), 9-oxa-3,7-diaza-bicyclo[3.3.1]nonane-3-carboxylic acid tert-butyl ester (21.1 g, 0.07965 mol; see WO 01/28992) and dry $K_2CO_3$ (48.9 g, 0.354 mol) in 200 ml of dry acetonitrile was stirred at 60° C. for five days under $N_2$ atmosphere. The reaction mixture was filtered through celite and filtrate was concentrated under reduced pressure. The residue was purified by column chromatography over silica gel using 27% ethyl acetate in petroleum ether, as eluent to yield the sub-title compound (20.5 g) as a solid.

(vii) 3-Fluoro-4-[2-(9-oxa-3,7-diaza-bicyclo[3.3.1] non-3-yl)-ethoxy]-benzonitrile hydrochloride hydrochloric acid salt 7-[2-(4-Cyano-2-fluoro-phenoxy)-ethyl]-9-oxa-3,7-diaza-bicyclo[3.3.1]nonane-3-carboxylic acid tert-butyl ester (20.5 g, from step (vi) above) was taken in 20 ml of dioxane and added 100 ml of dioxane (saturated with HCl gas) and stirred for 1 h at RT under nitrogen atmosphere. Solvent was decanted and the precipitated solid was washed with dry diethylether (4 times) and dried under vacuum to give HCl salt of the sub-title compound (21 g) as a solid.

(viii) (2-{7-[2-(4-Cyano-2-fluoro-phenoxy)-ethyl]-9-oxa-3,7-diaza-bicyclo[3.3.1]non-3-yl}-ethyl)-carbamic acid tert-butyl ester A suspension of intermediate 3-fluoro-4-[2-(9-oxa-3,7-diaza-bicyclo[3.3.1]non-3-yl)-ethoxy]-benzonitrile hydrochloride (5 g, 0.0137 mol, from step (vii) above), and tert-butyl 2-bromoethylcarbamate (3.98 g, 0.0178 mol , see WO 01/28992) and potassium carbonate (7.57 g, 0.0548 mol) in dry acetonitrile (100 ml) was stirred at 60° C. overnight under nitrogen atmosphere. The reaction mixture was filtered through celite and filtrate was concentrated under reduced pressure. The residue was purified by column chromatography over silica gel using 5% methanol in dichloromethane as eluent to give the sub-title compound (4.6 g) as an oil.

(viv) 4-{2-[7-(2-Amino-ethyl)-9-oxa-3,7-diaza-bicyclo[3.3.1]non-3-yl]-ethoxy}-3-fluoro-benzonitrile trifluoroacetic acid salt (2-{7-[2-(4-Cyano-2-fluoro-phenoxy)-ethyl]-9-oxa-3,7-diaza-bicyclo[3.3.1]non-3-yl}-ethyl)-carbamic acid tert-butyl ester (4.6 g from step (viii) above) was taken in dry dichloromethane (20 ml) and cooled to 0° C. Trifluoro acetic acid (75 ml) was added drop by drop and the reaction mixture was stirred at RT for 2 h under nitrogen atmosphere. Solvent and trifluoroacetic acid were evaporated under reduced pressure to give the TFA salt of the sub-title compound (7.6 g) as an oil.

(x) 4-{2-[7-(2-Amino-ethyl)-9-oxa-3,7-diaza-bicyclo[3.3.1]non-3-yl]-ethoxy}-3-fluoro-benzonitrile hydrochloric acid salt 4-{2-[7-(2-Amino-ethyl)-9-oxa-3,7-diaza-bicyclo[3.3.1]non-3-yl]-ethoxy}-3-fluoro-benzonitrile trifluoroacetic acid salt (8.3 g, 12.3 mmol, from step (viv) above) was dissolved in dioxane (15 ml). HCl (15 ml of a 4M solution in dioxane) was added whilst stirring resulting in the precipitation of the HCl-salt. The salt was filtered and dried, dissolved in water and freeze dried. Yield: 3.6 g of the title compound as a solid.

Preparation O

4-{2-[7-(3-Amino-propyl)-9-oxa-3,7-diaza-bicyclo[3.3.1]non-3-yl]-ethoxy}-3-fluoro-benzonitrile hydrochloric acid salt

(i) (3-Bromo-propyl)-carbamic acid tert-butyl ester $(Boc)_2O$ (13.5 g, 0.062 mol) was added drop by drop at 0° C. to a solution of 3-bromo propyl amine hydrobromide (15 g, 0.0688 mol) and triethyl amine (13.89 g, 0.1376 mol) in dry dichloromethane (125 ml) under nitrogen atmosphere. The reaction mixture was stirred at RT for 1 h and quenched with water. Organic layer was washed with water and brine and dried over sodium sulfate. Solvent evaporation under reduced pressure followed by purification over silica gel using 5% ethyl acetate in pet ether as eluent afforded the sub-title compound (11.6 g) as yellow oil.

(ii) (3-{7-[2-(4-Cyano-2-fluoro-phenoxy)-ethyl]-9-oxa-3,7-diaza-bicyclo [3.3.1]non-3-yl}-propyl)-carbamic acid ter-butyl ester A suspension of 3-Fluoro-4-[2-(9-oxa-3,7-diaza-bicyclo[3.3.1]non-3-yl)-ethoxy]-benzonitrile hydrochloride hydrochloric acid salt (5 g, 0.0137 mol, from step N (vii) above ), (3-Bromo-propyl)-carbamic acid tert-butyl ester (4.24 g, 0.0178 mol, from step (i) above) and potassium carbonate (7.57 g, 0.0548 mol) in dry acetonitrile (100 ml) was stirred at 60° C. overnight under nitrogen atmosphere. The reaction mixture was filtered through celite and solvent concentrated under reduced pressure. The residue was purified by column chromatography over silica gel using 5% methanol in dichloromethane as eluent to give the sub-title compound (5.8 g) as yellow oil.

(iii) 4-{2-[7-(3-Amino-propyl)-9-oxa-3,7-diaza-bicyclo[3.3.1]non-3-yl]-ethoxy}-3-fluoro-benzonitrile TFA-salt (3-{7-[2-(4-Cyano-2-fluoro-phenoxy)-ethyl]-9-oxa-3,7-diaza-bicyclo[3.3.1]non-3-yl}-propyl)-carbamic acid isopropyl ester (5.8 g, from step (ii) above) was taken in dry dichloromethane (25 ml) and cooled to 0° C. Trifluoroacetic acid (75 ml) was added drop by drop and the reaction mixture was stirred at RT for 2 h under nitrogen atmosphere. Solvent and trifluoroacetic acid were evaporated under reduced pressure to give the TFA salt of the sub-title compound (9 g) as an oil.

(iv) 4-{2-[7-(3-Amino-propyl)-9-oxa-3,7-diaza-bicyclo[3.3.1]non-3-yl]-ethoxy}-3-fluoro-benzonitrile hydrochloric acid salt 4-{2-[7-(3-Amino-propyl)-9-oxa-3,7-diaza-bicyclo [3.3.1]non-3-yl]-ethoxy}-3-fluoro-benzonitrile TFA-salt (7.79 g, 11.3 mmol, from step (iii) above) was dissolved in dioxane (15 ml). HCl (14 ml of a 4M solution in dioxane was added. The HCl-salt precipitated, the dioxane was decanted off and to the solid was added dioxane (10 ml ) followed by HCl (4 ml in dioxane). The solvent was decanted off and the solid was dried under vacuum. The solid was dissolved in water (5 ml) and freeze dried giving 2.98 g of the title compound Preparation P 2-(9-Oxa-3,7-diaza-bicyclo[3.3.1]non-3-yl)-ethanesulfonic acid 4-cyano-benzylamide (i) 2-Chloro-ethanesulfonic acid 4-cyano-benzylamide Chloroethane sulfonyl chloride (4.8 g, 0.029 mol) was added drop by drop to solution of 4-aminomethyl benzonitrile methan sulphonic acid salt acid (7 g, 0.029 mol) and pyridine (24 ml) in dry dichloromethane (25 ml) at −5° C. under nitrogen atmosphere. The reaction mixture was stirred at RT for 2 days and then partitioned between water and dichloromethane. The organic layer was washed with water and brine and dried over sodium sulfate. Solvent was evaporated under reduced pressure and the residue was purified by column chromatography over silica gel using 1% methanol in chloroform as eluent to give mixture of the sub-title compound and ethenesulfonic acid 4-cyano-benzylamide (3.4 g) as a solid. This was directly taken for next step without further purification.

(ii) 7-[2-(4-Cyano-benzylsulfamoyl)-ethyl]-9-oxa-3, 7-diaza-bicyclo[3.3.1]nonane-3-carboxylic acid tert-butyl ester A suspension of step (i) intermediate (3.4 g, 0.013 mol), 9-oxa-3,7-diaza-bicyclo[3.3.1]nonane-3-carboxylic acid tert-butyl ester; (3.49 g, 0.013 mol see WO 01/28992) and potassium carbonate (4.54 g, 0.033 mol) in dry acetonitrile (50 ml) was stirred at 60° C. overnight under nitrogen atmosphere. The reaction mixture was filtered and solvent concentrated under reduced pressure. The residue was purified by column chromatography over silica gel using 1% methanol in dichloromethane as eluent to give the sub-title compound (2.2 g) as white solid.

(iii) 7-[2-(4-Cyano-benzylsulfamoyl)-ethyl]-9-oxa-3, 7-diaza-bicyclo[3.3.1]nonane-3-carboxylic acid tert-butyl ester 7-[2-(4-Cyano-benzylsulfamoyl)-ethyl]-9-oxa-3,7-diaza-bicyclo[3.3.1]nonane-3-carboxylic acid tert-butyl ester (2.2 g, from step (ii) above) was taken in dry dioxane (5 ml) and was added 15 ml of dioxane (saturated with HCl gas) and stirred at RT for 30 min. The precipitated solid was filtered, washed with dry diethylether (three times) and finally dried under vacuum to give the title compound (1.96 g) as a solid.

Preparation Q 4-(2-Bromoethyl)-1,2-difluorobenzene (i) 1,2-Difluoro-4-(2-methoxy-vinyl)-benzene Potassium tert butoxide (11 g, 0.098 mol) was added to methoxymethyl triphenyl phosphonium chloride (31.12 g, 0.091 mol) in 150 ml of dry THF at −30° C. under argon atmosphere and stirred for 1 h. 3,4-difluorobenzaldehyde (10 g, 0.07 mol) in 60 ml of THF was added dropwise at the same temperature and stirring continued for 3 h at room temperature. The reaction mixture was treated with 100 ml water, 150 ml petroleum ether and filtered through celite. Organic layer was separated and aq. layer was extracted with petroleum ether (2×100 ml). Combined organic layer was washed with brine and dried over sodium sulfate. Solvent evaporation under reduced pressure followed by purification over silica gel using petroleum ether as eluent afforded (5.5 g) of the sub-titles compound as a colorless liquid.

(ii) (3,4-Difluoro-phenyl)-acetaldehyde

To a solution of 1,2-difluoro-4-(2-methoxy-vinyl)-benzene (5.5 g, 0.032 mol, from step (i) above) in 80 ml acetone was added 66 ml of 3 (M) HCl and stirred at 45° C. for 4 h. Acetone was evaporated under reduced pressure and the residue was partitioned between water and ether. The organic layer was washed with NaHCO$_3$, brine and dried over sodium sulfate. Solvent evaporation under reduced pressure afforded (5.5 g) of the sub-title compound as a liquid. This was directly taken for next step without further purification.

(iii) 2-(3,4-Difluoro-phenyl)-ethanol

NaBH$_4$ (1.46 g, 0.038 mol) was added at 0° C. to a solution (3,4-difluoro-phenyl)-acetaldehyde (5.5 g 0.35 mol, from step (ii) above) in 90 ml ethanol and stirred at RT overnight. The solvent was evaporated under reduced pressure and the residue was partitioned between 50 ml of 1 N HCl and 50 ml of diethylether. Organic layer was washed with water, dried over sodium sulfate and solvent evaporated under reduced pressure to give (5.5 g) of the sub-title compound as a liquid. This was directly taken for next step without further purification.

(iv) 4-(2-Bromo-ethyl)-1,2-difluorobenzene

A mixture of 2-(3,4-difluoro-phenyl)-ethanol (5 g, 0.032 mol, from step (iii) above), 51.84 ml (49%, 0.64 mol) of HBr in acetic acid and 5 ml of sulfuric acid was stirred at 100° C. for 4 h. The reaction mixture was poured into ice and extracted with diethylether. Organic layer was washed with NaHCO$_3$, water and dried over sodium sulfate. Solvent evaporation under reduced pressure followed by purification (three times) over silica gel using petroleum ether as eluent afforded (1.8 g) of the title compound as a liquid.

Preparation R

4-Bromomethyl-3-fluoro-benzonitrile

(i) (4-Bromo-2-fluoro-phenyl)-methanol

To a solution of 4-bromo-2-fluorobenzaldehyde (25 g, 0.123 mol) in methanol (250 ml) was added NaBH$_4$ (7.02 g, 0.1847 mol) and the reaction mixture was stirred at RT for 2 h. The reaction mixture was diluted with 25 ml of water and solvent evaporated under reduced pressure. The compound was extracted with ethyl acetate, organic layer was washed with water and brine and dried over sodium sulfate. Solvent evaporation under reduced pressure afforded the sub-title compound (25 g) as an oil. This was directly taken for next step without further purification.

(ii) 3-Fluoro-4-hydroxymethylbenzonitrile

A suspension of (4-bromo-2-fluoro-phenyl)-methanol (25 g, 0.122 mol, from step (i) above), Zn(CN)$_2$ (9.7 g, 0.085 mol) and Pd(PPh$_3$)$_4$ (7.04 g, 0.006 mol) in dry DMF (150 ml) was stirred at 90° C. overnight under nitrogen atmosphere. The reaction mixture was filtered and solvent concentrated under reduced pressure. The residue was purified by column chromatography over silica gel using 25% ethyl acetate in petroleum ether, as eluent to the sub-title compound (13 g) as white solid.

(iii) 4-Bromomethyl-3-fluorobenzonitrile

Carbon tetrabromide (5.7 g, 0.172 mol) in dry dichloromethane (150 ml) as added to a solution of step 3-fluoro-4-hydroxymethylbenzonitrile (13 g, 0.086 mol, from step (ii) above) and triphenyl phosphine (45 g, 0.172 mol) in dry dichloromethane (50 ml) and stirred at RT overnight under nitrogen atmosphere. The reaction was quenched with water, extracted with dichloromethane, washed with water and brine and dried over sodium sulfate. Solvent evaporated under reduced pressure and the residue was purified by column chromatography over silica gel using 10% ethyl acetate in petroleum ether as eluent to give the title compound (8 g) as an off-white solid.

Preparation S

2-(2-Bromo-ethoxy)-1,3-difluorobenzene

A suspension of 2,6-difluoro phenol (18 g, 0.385 mol), 1,2-dibromoethane (71.6 ml, 0.83 mol) and K$_2$CO$_3$ (47.86 g, 0.3463 mol) in dry acetonitrile (190 ml) was stirred at 60° C. overnight under nitrogen atmosphere. The reaction mixture was filtered and solvent concentrated under reduced pressure. The residue was purified by column chromatography over silica gel using 7% ethyl acetate in petroleum ether as eluent to give the title compound (20.8 g) as colorless oil.

Preparation T

4-(3-Bromo-propoxy)-3,5-difluorobenzonitrile

A mixture of 2,6-difluoro-4-cyanophenol (6 g, 0.038 mol), 1,3-dibromopropane (46.9 g, 0.23 mol) and dry potassium carbonate (8 g, 0.058 mol) in dry DMF (50 ml) was stirred at RT overnight under nitrogen atmosphere. Solvent was removed under reduced pressure and the residue was purified by column chromatography over silica gel using 4% ethyl acetate in petroleum ether as eluent to yield (9.6 g) of the title compound as a liquid.

Preparation U

4-(3-Bromo-propoxy)-3-fluorobenzonitrile

(i) 3-Fluoro-4-(3-hydroxy-propoxy)-benzonitrile

A mixture of 4-cyano-2-fluoro phenol (5 g, 0.0365 mol; from prep N(iv) above), 3-bromopropanol (10.15 g, 0.073 mol) and potassium carbonate (7.6 g, 0.054 mol) in dry acetone (50 ml) was stirred at 60° C. overnight under nitrogen atmosphere. The reaction mixture was filtered and the solvent was concentrated under reduced pressure. The residue was purified by column chromatography over silica gel using 5% ethyl acetate in petroleum ether to yield (5.5 g) of the sub-title compound as a solid.

(ii) 4-(3-Bromopropoxy)-3-fluorobenzonitrile

PBr$_3$ (8.14 g, 0.03 mol) was added drop by drop at 0° C. to a solution of 3-fluoro-4-(3-hydroxypropoxy)-benzonitrile (5.5 g, 0.028 mol, from step (i) above in carbon tetrachloride (50 ml) and stirred at room temperature overnight under nitrogen atmosphere. The reaction was quenched with water, and extracted with dichloromethane. Organic layer was washed with water, brine, dried over sodium sulfate and solvent evaporated under reduced pressure. The residue was purified by column chromatography over silica gel using 6% ethyl acetate in petroleum ether as eluent to yield (4.3 g) of the title compound as a liquid.

Preparation U

Methanesulfonic acid 2-(2,6-difluoro-phenyl)-ethyl ester

(i) methyl-2,6-difluoro phenyl acetate

H$_2$SO$_4$ (conc., 0.75 ml) was added to a solution of (2,6-difluoro-phenyl)-acetic acid (14 g, 0.0814 mol) in dry methanol (160 ml) and stirred at room temperature overnight. Solvent evaporated under reduced pressure and the residue was partitioned between water and diethyl ether. Organic layer was washed water, brine and dried over sodium sulfate. Solvent evaporation under reduced pressure yielded 16 g of methyl-2,6-difluoro phenyl acetate as pale yellow liquid. This was directly taken for next step without further purification.

(ii) 2-(2,6-Difluoro-phenyl)-ethanol

LAH (4.7 g, 0.129 mol) in dry diethylether (400 ml) was added at 0° C. to a stirred suspension of methyl-2,6-difluoro phenyl acetate (16 g, 0.086 mol, from step (i) above in dry diethylether (80 ml) and stirred at room temperature for 2 h under nitrogen atmosphere. The reaction mixture was quenched with water, NaOH and filtered. The aq. Layer was again acidified with 1.5 N HCl and extracted with diethylether. Organic layer was washed with water, brine and dried over sodium sulfate. Solvent evaporation under reduced pressure afforded (13.5 g) of 2-(2,6-difluoro-phenyl)ethanol as aliquid. This was directly taken for next step without further purification.

(iii) Methanesulfonic acid 2-(2,6-difluoro-phenyl)-ethyl ester

Methanesulfonyl chloride (10.76 g, 0.094 mol) was added at 0° C. to a solution of 2-(2,6-difluoro phenyl)ethanol (13.5 g, 0.085 mol, from step (ii) above) and triethylamine (12.93 g, 0.128 mol) in dry dichloromethane (135 ml) and stirred for 3 h under nitrogen atmosphere. The reaction was quenched with water, extracted with dichloromethane, dried over sodium sulfate and solvent evaporated under reduced pressure to give (18 g) of the title compound as an oil.

Preparation V

1-(2-Bromoethyl)-4-trifluoromethylbenzene

(i) 1-(2-Methoxy-vinyl)-4-trifluoromethylbenzene

Potassium tert butoxide (13.46 g, 0.120 mol) was added to methoxymethyl triphenyl phosphonium chloride (38.30 g, 0.112 mol) in 150 ml dry THF at −30° C. under argon atmosphere and stirred for 1 h. 4-trifluoromethylbenzaldehyde (15.0 g, 0.086 mol) in 60 ml THF was added dropwise at the same temperature and stirring continued for 3 h at room temperature. The reaction mixture was treated with 100 ml water, 150 ml petroleum ether and filtered through celite. Organic layer was separated and the aq. layer was extracted with petroleum ether (2×100 ml). Combined organic layer was washed with brine and dried over sodium sulfate. Solvent evaporation under reduced pressure followed by purification over silica gel using petroleum ether as eluent afforded (10.5 g) of the sub-title compound as a colorless liquid. This was directly taken for next step without further purification.

(ii) (4-Trifluoromethyl-phenyl)-acetaldehyde

To a solution of 1-(2-methoxy-vinyl)-4-trifluoromethylbenzene (10.5 g, 0.052 mol, from step (i) above) in 158 ml acetone was added 107.3 ml 3 M HCl and stirred at 45° C. for 4 h. Acetone was evaporated under reduced pressure and the residue was partitioned between water and ether. Organic layer was washed with NaHCO₃, brine and dried over sodium sulfate. Solvent evaporation under reduced pressure afforded the sub-title compound (9.4 g) as pale yellow liquid. This was directly taken for next step without further purification.

(iii) 2-(4-Trifluoromethylphenyl)-ethanol

NaBH₄ (2 g, 0.055 mol) was added at 0° C. to a solution of 4-trifluoromethyl-phenyl)-acetaldehyde (9.4 g, 0.05 mol, from step (ii) above) in 154 ml ethanol and stirred at RT overnight. The solvent was evaporated under reduced pressure and the residue was partitioned between 50 ml 1 N HCl and 50 ml diethyl ether. Organic layer was washed with water, dried over sodium sulfate and the solvent evaporated under reduced pressure to give 10 g of the sub-title compound as a liquid. This was directly taken for next step without further purification.

(iv) 1-(2-Bromo-ethyl)-4-trifluoromethylbenzene

A mixture of step 2-(4-trifluoromethylphenyl)-ethanol (10 g, 0.053 mol, from step (iii) above), 86 ml (1.06 M) HBr in acetic acid and 10 ml sulfuric acid was stirred at 100° C. for 4 h. The reaction mixture was poured into ice and extracted with diethylether. The organic layer was washed with NaHCO₃, water and dried over sodium sulfate. Solvent evaporation under reduced pressure followed by purification over silica gel using petroleum ether as eluent afforded 5 g of the title compound as a liquid.

Preparation W

Methanesulfonic acid 2-(4-difluoromethoxy-phenyl)-ethyl ester

(i) 1-Difluoromethoxy-4-((EZ)-2-methoxy-vinyl)-benzene (E/Z ratio ~3:2)

A suspension of methoxymethyl triphenylphosphonium chloride (6.69 g, 19.5 mmol) in THF (200 mL) was cooled to ca. −20° C. n-BuLi (2.5 M in hexanes, 7.2 mL, 18 mmol) was added in portions over 5 min and the orange-red reaction mixture was stirred for an additional 15 min. 4-difluoromethoxybenzaldehyde (2.58 g, 15.0 mmol) in THF (50 mL) was added at −10° C. and the reaction mixture was stirred at this temperature for 30 min and then at room temperature for 19 h. Water (100 mL) was added and the mixture was concentrated under reduced pressure. The remaining aqueous phase was extracted with ethyl acetate (2×100 mL) and the combined organic phase was washed with water (2×100 mL) and brine (100 mL), dried over Na₂SO₄, and concentrated in vacuo. The crude product was purified by three times repeated chromatography on silica gel. (Horizon™, flash system from Biotage™. Column: Flash 40+M, 40×150 mm. Eluent: 3% ethyl acetate in heptane. Combination of pure fractions and concentration in vacuo afforded 1.60 g (53%) of the title compound as a colourless oil.

1H-NMR (500 MHz, CDCl₃): δ 7.56 (2H, minor isomer), 7.20 (2H, major isomer), 7.03 (d, 2H, minor isomer), 7.02 (d, 2H, major isomer), 7.00 (d, 1H, major isomer), 6.47 (t, 1H, minor isomer), 6.47 (t, 1H, major isomer), 6.14 (d, 1H, minor isomer), 5.78 (d, 1H, major isomer), 5.20 (d, 1H, minor isomer), 3.78 (s, 3H, minor isomer), 3.69 (s, 3H, major isomer)

(ii) (4-Difluoromethoxyphenyl)-acetaldehyde

To a solution of 1-difluoromethoxy-4-((E,Z)-2-methoxyvinyl)-benzene (E/Z ratio ~3:2,) (1.58 g, 7.9 mmol, from step (i) above ) in acetone (20 mL) was added 3 M HCl (3.7 mL, 11.1 mmol) and the solution was stirred at 45° C. for 4 h. After concentration under reduced pressure, water (25 mL) was added to the residue and the aqueous phase was extracted with diethylether (2×50 mL). The combined organic phase was washed with saturated aqueous NaHCO₃ (50 mL) and brine (50 mL), dried over Na₂SO₄, and concentrated in vacuo to give 1.32 g of crude product as a yellow oil with a purity of ca. 80%. The crude product was used directly in the subsequent reduction step without further purification.

1H-NMR (500 MHz, CDCl₃): δ 9.76 (t, 1H), 7.21 (d, 2H), 7.13 (d, 2H), 6.51 (t, 1H), 3.70 (d, 2H)

(iii) 2-(4-Difluoromethoxyphenyl)-ethanol

A solution of (4-difluoromethoxyphenyl)-acetaldehyde 1.22 g, 6 mmol; from step (ii) above) in ethanol (20 mL) was cooled to 0° C. Sodium borohydride (0.27 g, 7.2 mmol) was added and the resulting reaction mixture stirred at 0° C. for 2 h and then at room temperature for 16 h. After concentration under reduced pressure, the residue was diluted with diethylether (50 mL) and 1 M HCl (50 mL). The phases were separated and the organic phase was washed with water (50 mL) and brine (50 mL), dried over Na$_2$SO$_4$, and concentrated in vacuo. The crude product was purified by two times repeated chromatography on silica gel. (Horizon™, flash system from Biotage™. Column: Flash 40+M, 40×150 mm. Eluent: Gradients from 25 to 40% ethyl acetate in heptane. Concentration in vacuo afforded 0.62 g (50%) of the sub-title compound as a light yellow oil.

1H-NMR (500 MHz, CDCl$_3$): δ 7.22 (d, 2H), 7.07 (d, 2H), 6.48 (t, 1H), 3.88-3.80 (m, 2H), 2.85 (t, 2H), 1.55 (m, br, 1H)

(iv) Methanesulfonic acid 2-(4-difluoromethoxyphenyl)-ethyl ester

A solution of 2-(4-difluoromethoxyphenyl)-ethanol (0.582 g, 3.09 mmol, from step (iii) above) in methylene chloride (8 mL) was cooled to 0° C. Triethylamine (0.52 mL, 3.7 mmol) was added followed by a solution of methanesulfonyl chloride (0.26 mL, 3.4 mmol) in methylene chloride (2 mL) and the reaction mixture was stirred at 0° C. for 90 min. The reaction mixture was diluted with methylene chloride (40 mL) and the organic phase was washed with water (2×30 mL) and brine (30 mL), dried over Na$_2$SO$_4$, and concentrated in vacuo to give 0.78 g (95%) of the title compound as a colourless oil.

1H-NMR (500 MHz, CDCl$_3$): δ 7.23 (d, 2H), 7.09 (d, 2H), 6.49 (t, 1H), 4.40 (t, 2H), 3.05 (t, 2H), 2.89 (s, 3H)

Preparation X 1-(3-Bromopropoxy)-2-fluorobenzene

A mixture of 2-fluorophenol (2.24 g, 20.0 mmol), 1,3-dibromopropane (20.3 mL, 200 mmol), and potassium carbonate (2.76 g, 20.0 mmol) in acetonitril (30 mL) was heated at 80° C. overnight. The reaction mixture was filtered and the filtrate was concentrated in vacuo to give 4.70 g of the title compound as a light yellow oil with a purity of ca. 80%. The product was used in the subsequent reaction step without further purification.

1H-NMR (500 MHz, CDCl$_3$): δ 7.11-7.03 (m, 2H), 6.99 (m, 1H), 6.91 (m, 1H), 4.18 (t, 2H), 3.64 (t, 2H), 2.39-2.31 (m, 2H)

Preparation Y 2-(3-Bromo-propoxy)-1,4-difluoro-benzene

A mixture of 2,5-difluorophenol (2.60 g, 20.0 mmol), 1,3-dibromopropane (20.3 mL, 200 mmol), and potassium carbonate (2.76 g, 20.0 mmol) in acetonitril (30 mL) was heated at 80° C. overnight. The reaction mixture was filtered and the filtrate was concentrated in vacuo to give 4.82 g of the title compound as a light yellow oil with a purity of ca. 80%. The product was used in the subsequent reaction step without further purification.

1H-NMR (500 MHz, CDCl$_3$): δ 7.01 (m, 1H), 6.72 (m, 1H), 6.59 (m, 1H), 4.15 (t, 2H), 3.62 (t, 2H), 2.39-2.31 (m, 2H)

Preparation Z 4-(3-Bromo-propoxy)-1,2-difluoro-benzene

A mixture of 3,4-difluorophenol (2.60 g, 20.0 mmol), 1,3-dibromopropane (20.3 mL, 2001 mmol), and potassium carbonate (2.76 g, 20.0 mmol) in acetonitril (30 mL) was heated at 75° C. overnight. The reaction mixture was filtered and the filtrate was concentrated in vacuo. The crude product was purified by chromatography on silica gel. (Horizon™, flash system from Biotage™. Column: Flash 40+M, 40×150 mm. Eluent: 3% ethyl acetate in heptane. Concentration in vacuo afforded, 4.35 g of the title compound as a colourless oil with a purity of ca. 90%.

1H-NMR (500 MHz, CDCl$_3$): δ 7.06 (dd, 1H), 6.73 (m, 1H), 6.60 (m, 1H), 4.05 (t, 2H), 3.59 (t, 2H), 2.33-2.27 (m, 2H)

Preparation AA 1-(3-Bromopropoxy)-3-fluorobenzene

A mixture of 3-fluorophenol (2.24 g, 20.0 mmol), 1,3-dibromopropane (20.3 mL, 200 nmol), and potassium carbonate (2.76 g, 20.0 mmol) in acetonitril (30 mL) was heated at 80° C. overnight. The reaction mixture was filtered and the filtrate was concentrated in vacuo. The crude product was purified by chromatography on silica gel. (Horizon™, flash system from Biotage™. Column: Flash 40+M, 40×150 mm. Eluent: 3% ethyl acetate in heptane, Concentration in vacuo afforded 3.68 g of the title compound as a colourless oil with a purity of ca. 75%. The product was used in the subsequent reaction step without further purification.

1H-NMR (500 MHz, CDCl$_3$): δ 7.25 (m, 1H), 6.75-6.63 (m, 2H), 4.12 (t, 2H), 3.62 (t, 2H), 2.38-2.31 (m, 2H)

Preparation AB

Methanesulfonic acid 2-(4-fluoro-benzyloxy)-ethyl ester (i) 2-(4-Fluorobenzyloxy)-ethanol To a suspension of sodium hydride (1.9 g of a 60% suspension in mineral oil, washed with heptane) in THF (20 mL) was added ethylene glycol (19.9 g, 0.32 mol) in portions over 15 min. The reaction mixture was stirred at room temperature for 2 h and then heated to 80° C. Benzylbromide (6.05 g, 32.0 mmol) in THF (30 mL) was added and the reaction mixture was stirred at 80° C. for 3.5 h. After cooling to room temperature, saturated aqeuous NH$_4$Cl (75 mL) was added and the phases were separated. The water phase was extracted with diethylether (3×75 mL) and the combined organic phase was washed with saturated aqueous NH$_4$Cl (75 mL) and brine (75 mL), dried over MgSO$_4$ and concentrated in vacuo to afford 6.83 g (95%) of the sub-title compound as an oil with a purity of ca. 90%.

1H-NMR (500 MHz, CDCl$_3$): δ 7.33-7.28 (m, 2H), 7.06-7.00 (m, 2H), 4.51 (s, 2H), 3.77-3.72 (m, 2H), 3.60-3.55 (m, 2H), 2.23 (m, 1H)

(ii) Methanesulfonic acid 2-(4-fluoro-benzyloxy)-ethyl ester

A solution of 2-(4-fluorobenzyloxy)-ethanol (5.11 g, 30.0 mmol, from step (i) above) in methylene chloride (60 mL) was cooled to −10° C. Triethylamine (5.0 mL, 36 mmol) was added followed by methanesulfonyl chloride (3.78 g, 33.0 mmol) and the reaction mixture was stirred at −5° C. for 2 h. The reaction mixture was diluted with methylene chloride (200 mL) and the organic phase was washed with water (2×75 mL) and brine (75 mL), dried over MgSO$_4$, and concentrated in vacuo to give 7.16 g (96%) of the title compound as a yellow oil.

1H-NMR (500 MHz, CDCl$_3$): δ 7.33-7.28 (m, 2H), 7.07-7.01 (m, 2H), 4.54 (s, 2H), 4.41-4.37 (m, 2H), 3.76-3.71 (m, 2H), 3.09 (s, 3H)

Preparation AC

4-{[7-(2-aminoethyl)-9-oxa-3,7-diazabicyclo[3.3.1]non-3-yl]methyl}benzonitrile, hydrochloride salt.

(i) tert-butyl{2-[7-(4-cyanobenzyl)-9-oxa-3,7-diazabicyclo[3.3.1]non-3-yl]ethyl}carbamate Potassium carbonate (3.82 g, 27.6 mmol) was added to a mixture of tert-butyl [2-(9-oxa-3,7-diazabicyclo[3.3.1]non-3-yl)ethyl]carbamate (5.00 g, 18.4 mmol) and 4-(bromomethyl)benzonitrile (3.61 g, 18.4 mmol) in acetonitrile (150 mL). The mixture was heated to reflux over night, cooled to room temperature, filtered and evaporated. The residue was dissolved in dichloromethane (100 mL), washed with water and dried over MgSO$_4$. Purification by preparative HPLC gave 7.04 g (78%) of the sub.title compound as a salt with one equivalent of acetic acid and one equivalent of formic acid.

$^1$H NMR (500 MHz, CD$_3$OD) δ 8.49 (1 H, bs), 7.77 (2 H, d), 7.58 (2H, d), 4.15 (2 H, m), 3.75 (2 H, s), 3.69 (2 H, m), 3.46 (2 H, t), 3.33 (2 H, m), 3.16 (2 H, t) 3.09 (2 H, m), 2.76 (2 H, m), 1.96 (3 H, s), 1.44 (9 H, s).

4-{[7-(2-aminoethyl)-9-oxa-3,7-diazabicyclo[3.3.1]non-3-yl]methyl}benzonitrile, hydrochloride salt.

A saturated solution of HCl in ethyl acetate (200 mL) was added to an ice-cooled slurry of the acetic and formic acid salt of tert-butyl {2-[7-(4-cyanobenzyl)-9-oxa-3,7-diazabicyclo[3.3.1]non-3-yl]ethyl}carbamate (7.00 g, 14.2 mmol). The reaction mixture was stirred at room temperature for 3 hours after which it was filtered and the resultant solid was washed with ethyl acetate. Drying in vacuo gave 6.12 g (96%) of the title compound with one equivalent of residual ethyl acetate.

$^1$H NMR (500 MHz, D$_2$O) δ 7.95 (2 H, d), 7.71 (2 H, d), 4.48 (2H, s), 4.31 (2 H, m), 3.69 (2 H, m), 3.52 (2 H, m), 3.20 (4 H, m), 2.77 (4 H, m).

Preparation AD

Methanesulfonic acid 2-benzo[d]isoxazol-3-yl-ethyl ester (i) 2-Benzo[d]isoxazol-3-yl-ethanol To a solution of benzo[d]isoxazol-3-yl-acetic acid (0.86 g, 4.85 mmol) in anhydrous THF (40 mL) was added dropwise borane dimethylsulfide complex (0.58 mL, 10 M, 5.8 mmol) at 0° C. The mixture was allowed to warm to room temperature and was stirred over night. MeOH (10 mL) was carefully added and when the gas evolution ceased, the mixture was heated under gentle reflux for 4 hours. The reaction mixture was concentrated in vacuo and the remainder was dissolved in dichloromethane (20 mL). An aqueous solution of Na$_2$CO$_3$ (20 mL) was added and the aqueous layer was extracted with dichloromethane (3×20 mL). The combined organic layers were dried over Na$_2$SO$_4$ and concentrated in vacuo. The crude product was purified by chromatography on silica gel which afforded 537 mg (67.8%) of the title compound.

$^{13}$C NMR (125.7 MHz, CDCl$_3$) δ 163.06, 156.92, 130.27, 123.65, 121.98, 121.65, 110.10, 60.34, 29.01

(ii) Methanesulfonic acid 2-benzo[d]isoxazol-3-yl-ethyl ester

To a solution of 2-benzo[d]isoxazol-3-yl-ethanol (0.537 g, 3.29 mmol, from step (i) above ) and triethylamine (0.55 mL, 3.95 mmol) in dichloromethane (20 mL) was added methanesulfonyl chloride (0.31 mL, 3.95 mmol) at 0° C. The reaction mixture was stirred for 1 hour and was then extracted with water (2×20 mL) and brine (20 mL). The organic layer was dried over Na$_2$SO$_4$ and concentrated in vacuo, which afforded 818 mg (98%) of the title compound.

$^1$H NMR (500 MHz, CDCl$_3$) δ 7.73 (1H, d), 7.61 (2H, m), 7.37 (1H, m), 4.73 (2H, t), 3.49 (2H, t), 3.01 (3H, s)

Preparation AE

Methanesulfonic acid 2-(2-fluoro-phenyl)-ethyl ester

To a solution of 2-(2-fluorophenyl)-ethanol (4.00 g, 28.5 mmol) and triethylamine (6.36 mL, 45.7 mmol) in dichloromethane (15 mL) was added methanesulfonyl chloride (2.88 mL, 37.1 mmol) at −5° C. The mixture was stirred for 4 hours and was allowed to slowly warm to room temperature. The mixture was diluted with dichloromethane and extracted with 1 M HCl and water. The organic layer was dried over Na$_2$SO$_4$ and concentrated in vacuo. The crude product was purified by column chromatography, using dichloromethane as eluent, to afford 5.88 g (94.4%) the title compound.

$^1$H NMR (400 MHz, CDCl$_3$) δ 7.28-7.22 (2H, m), 7.12-7.02 (2H, m), 4.42 (2H, t), 3.10 (2H, t), 2.88 (3H, s)

EXAMPLES

Example 1

N-(2-{7-[(2S)-3-(4-Cyanophenoxy)-2-hydroxypropyl]-9-oxa-3,7-diaza-bicyclo[3.3.1]non-3-yl}ethyl)-1-phenylmethanesulfonamide 4-{(2S)-3-[7-(2-Aminoethyl)-9-oxa-3,7-diazabicyclo[3.3.1]non-3-yl]-2-hydroxypropoxy}benzonitrile (0.096 g, 0.28 mmol; see step Preparation A above) was dissolved in a 1:2 ratio of DCM:acetonitrile (3 mL). Triethylamine (0.17 g, 1.68 mmol) was added, followed by phenylmethanesulfonyl chloride (0.068 g, 0.36 mmol). The mixture was stirred at room temperature overnight with K$_2$CO$_3$ (0.38 g, 2.77 mmol) to ensure that the free base of triethylamine was in the reaction mixture. The reaction mixture was filtered and the filtrate concentrated under reduced pressure. Purification by preparative HPLC gave 0.1 g (72%) of the title compound.

$^1$H NMR (400 MHz, CD$_3$OD) δ 7.64-7.66 (2H, d), 7.36-7.43 (5H, m), 7.05-7.07 (2H, m), 4.41 (3H, m), 4.17 (2H, m), 4.08 (2H, m), 3.62-3.7 (2H, m), 3.12-3.4 (8H, m), 2.72-2.86 (2H, m), 2.46-2.59 (2H, m).

Example 2

N-(2-{7-[2-(3,4-Bis(difluoromethoxy)phenyl)ethyl]-9-oxa-3,7-diazabicyclo-[3.3.1]non-3-yl}ethyl)-4-cyanobenzenesulfonamide A mixture of 4-cyano-N-[2-(9-oxa-3,7-diazabicyclo[3.3.1]non-3-yl)ethyl]-benzenesulfonamide (0.3 g, 7.5 mmol; see Preparation E above), 4-(2-bromo-ethyl)-1,2-bis (difluoromethoxy)benzene (0.26 g, 9 mmol; see Preparation G above) and potassium carbonate (0.41 g, 30 mmol) was stirred at 60° C. overnight under a nitrogen atmosphere. The reaction mixture was filtered and solvent was evaporated under reduced pressure. The residue was purified by column chromatography, using methanol in chloroform as eluent, to yield the title compound as a white solid. Yield: 0.23 g.

$^{13}$C NMR (75 MHz) δ 144.5, 142.31 140.52, 132.78, 127.51, 126.91, 122.53, 122.34, 119.23, 117.29, 116.02, 115.76, 112.29, 68.14, 67.50, 66.72, 61.22, 56.34, 55.35, 54.48, 53.33, 39.07, 38.74, 31.39

Example 3

4-Cyano-N-(2-{7-[2-(4-difluoromethoxy-phenyl)-ethyl]-9-oxa-3,7-diaza-bicyclo[3.3.1]non-3-yl}-ethyl)-benzenesulfonamide A mixture of 4-cyano-N-[2-(9-oxa-3,7-diaza-bicyclo [3.3.1]non-3-yl)-ethyl]-benzenesulfonamide dihydrochloride (0.164 g, 0.40 mmol, see prep E above), methanesulfonic acid 2-(4-difluoromethoxy-phenyl)-ethyl ester (0.128 g, 0.48 mmol, from Prep W above), potassium carbonate (0.210 g, 1.52 mmol), and water (0.1 mL) in acetonitrile (4 mL) was heated by microwave irradiation (160° C., 15 min). Solid material was filtered off and the filtrate was loaded onto a cation-exchange column (SCX-2, Isolute™, 2 g/15 mL). The column was washed with a solution of methylene chloride/acetonitrile/methanol (2:1:1, 40 mL) and eluted with 20% methanol saturated with ammonia in methylene chloride (30 mL). The filtrate was concentrated in vacuo and the crude product was purified by chromatography on silica gel using methanol in chloroform as eluent. Concentration in vacuo afforded 37 mg (18%) of the title compound as an yellow oil.

1H-NMR (500 MHz, CDCl$_3$): δ 8.00 (d, 2H), 7.78 (d, 2H), 7.30 (d, 2H), 7.03 (d, 2H), 6.47 (t, 1H), 4.15-3.70 (m, broad, 2H), 3.70-2.25 (m, 16H) 13C-NMR (125 MHz, CDCl$_3$): δ 149.8, 144.9, 137.3, 133.0, 130.3, 127.7, 119.8, 117.5, 116.1, 116.1 (t), 68.2, 62.2, 56.8, 54.7, 53.6, 39.4, 32.1.

Example 4

4-Cyano-N-(2-{7-[2-(4-difluoromethoxy-phenyl)-ethyl]-9-oxa-3,7-diaza-bicyclo[3.3.1]non-3-yl}-ethyl)-N-methyl-benzenesulfonamide A mixture of 4-cyano-N-methyl-N-[2-(9-oxa-3,7-diaza-bicyclo[3.3.1]non-3-yl)-ethyl]-benzenesulfonamide dihydrochloride (0.169 g, 0.40 mmol, prep. I above), methanesulfonic acid 2-(4-difluoromethoxy-phenyl)-ethyl ester (0.107 g, 0.40 mmol, prep W above ), potassium carbonate (0.177 g, 1.28 mmol), and water (0.1 mL) in acetonitrile (4 mL) was heated in an oil bath (60° C.) for 20 h. Solid material was filtered off and the filtrate was loaded onto a cation-exchange column (SCX-2, Isolute™, 2 g/15 mL). The column was washed with a solution of methylene chloride/acetonitrile/methanol (2:1:1, 40 mL) and eluted with 20% methanol saturated with ammonia in methylene chloride (30 mL). The filtrate was concentrated in vacuo and the crude product was purified by chromatography on silica gel using methanol saturated with ammonia in dichloromethane eluent. Concentration in vacuo afforded 118 mg (57%) of the title compound as a solid white material.

1H-NMR (500 MHz, CDCl$_3$): δ 7.91 (d, 2H), 7.81 (d, 2H), 7.20 (d, 2H), 7.01 (d, 2H), 6.48 (t, 1H), 3.88 (m, br, 2H), 3.21-3.14 (m, 2H), 2.98 (s, 3H), 2.91-2.79 (m, 4H), 2.75-2.67 (m, 2H), 2.58-2.40 (m, 8H)

13C-NMR (125 MHz, CDCl$_3$): δ 149.5, 142.6, 137.9, 133.0, 130.1, 127.9, 119.6, 117.4, 116.3, 116.1 (t), 68.4, 61.1, 58.3, 56.4, 46.7, 35.8, 32.3

Example 5

N-{2-[7-(2-Benzo[d]isoxazol-3-yl-ethyl)-9-oxa-3,7-diaza-bicyclo[3.3.1]non-3-yl]-ethyl}-4-cyano-benzenesulfonamide To 4-cyano-N-[2-(9-oxa-3,7-diaza-bicyclo[3.3.1]non-3-yl)-ethyl]-benzenesulfonamide dihydrochloride (0.123 g, 0.30 mmol, from prep E above), methanesulfonic acid 2-benzo[d]isoxazol-3-yl-ethyl ester (0.076 g, 0.315 mmol, from prep AD above) and potassium carbonate (0.145 g, 1.05 mmol; from Prep ) was added acetonitrile (4 mL) and water (0.1 mL). The mixture was heated by microwave irradiation (10 minutes, 160° C.) and was then filtered and evaporated. The crude product was purified by chromatography on silica gel using methanol saturated with ammonia in dichloromethane as eluent, which afforded 60 mg (41.5%) of the title compound.

$^1$H NMR (500 MHz, CDCl$_3$) δ 8.00 (2H, d), 7.85 (1H, d), 7.78 (2H, d), 7.55 (2H, m), 7.31 (1H, m), 3.91 (2H, m), 3.39 (2H, m), 3.12-2.47 (14 H, m, broad)

Example 6

4-Cyano-N-(2-{7-[2-(2-fluoro-phenoxy)-ethyl]-9-oxa-3,7-diaza-bicyclo[3.3.1]non-3-yl}-ethyl)-N-methyl-benzenesulfonamide To 4-cyano-N-methyl-N-[2-(9-oxa-3,7-diaza-bicyclo [3.3.1]non-3-yl)-ethyl]-benzenesulfonamide dihydrochloride (0.127 g, 0.30 mmol, prep I above), 1-(2-bromo-ethoxy)-2-fluoro-benzene (0.069 g, 0.315 mmol;) and potassium carbonate (0.145 g, 1.05 mmol) was added acetonitrile (4 mL) and water (0.1 mL). The mixture was heated by microwave irradiation (10 minutes, 160° C.) and was then filtered and evaporated. The crude product was purified by chromatography on silica gel using methanol saturated with ammonia in dichloromethane as eluent, which afforded 85 mg (58.0%) of the title compound.

$^{13}$C NMR (125.7 MHz, CDCl$_3$) δ 153.90, 151.95, 147.02, 142.81, 133.06, 128.02, 124.64, 124.61, 121.54, 117.60, 116.53, 116.38, 116.33, 115.36, 68.52, 67.57, 58.46, 58.27, 56.96, 56.44, 46.66, 35.93

Example 7

2-{7-[2-(3-Fluoro-phenyl)-ethyl]-9-oxa-3,7-diaza-bicyclo[3.3.1]non-3-yl}-ethanesulfonic acid 4-cyano-benzylamide To 2-(9-oxa-3,7-diaza-bicyclo[3.3.1]non-3-yl)-ethanesulfonic acid 4-cyano-benzylamide dihydrochloride (0.127 g, 0.30 mmol; prep P above), 1-(2-bromo-ethyl)-3-fluoro-benzene (0.064 g, 0.315 mmol) and potassium carbonate (0.145 g, 1.05 mmol) was added acetonitrile (4 mL) and water (0.1 mL). The mixture was stirred for 20 minutes before it was heated by microwave irradiation (10 minutes, 160° C.) and was then filtered and evaporated. The crude product was purified by chromatography on silica gel using methanol saturated with ammonia in dichloromethane as eluent, which afforded 43 mg (30.3%) of the title compound.

$^{13}$C NMR (125.7 MHz, CDCl$_3$) δ 163.90, 161.94, 144.35, 141.66, 132.65, 130.03, 129.96, 128.11, 123.86, 118.70, 115.12, 114.95, 113.51, 113.34, 111.76, 68.34, 60.85, 56.85, 56.41, 54.40, 47.82, 47.47, 31.35

Example 8

4-Cyano-N-{2-[7-(1-methyl-1H-indol-3-ylmethyl)-9-oxa-3,7-diaza-bicyclo[3.3.1]non-3-yl]-ethyl}-benzenesulfonamide A mixture of 4-cyano-N-[2-(9-oxa-3,7-diaza-bicyclo[3.3.1]non-3-yl)-ethyl]-benzenesulfonamide (0.101 g, 0.30 mmol) and 1-methyl-1H-indole-3-carbaldehyde (0.081 g, 0.51 mmol) in 1,2-dichloroethane (4 mL) was agitated for 1.5 hours at room temperature. Sodium triacetoxyborohydride (0.216 g, 1.02 mmol) was added and resulting mixture was agitated over night at room temperature. An aqueous solution of Na$_2$CO$_3$ (3 mL) was added and the aqueous layer was extracted with dichloromethane (3×4 mL). The combined organic layers were concentrated in vacuo and the crude product was purified by chromatography on silica gel using methanol saturated with ammonia in dichloromethane as eluent, which afforded 76 mg (52.8%) of the title compound.

$^{13}$C NMR (125.7 MHz, CDCl$_3$) δ 144.59, 136.86, 132.87, 130.73, 129.14, 127.65, 121.86, 119.68, 119.10, 117.56, 116.05, 109.75, 68.56, 56.97, 55.04, 54.68, 54.19, 39.40, 32.93

Example 9

N-(2-{7-[2-(4-cyanophenoxy)ethyl]-9-oxa-3,7-diazabicyclo[3.3.1]non-3-yl}ethyl)-3,5-dimethylisoxazole-4-sulfonamide 4-{2-[7-(2-Amino-ethyl)-9-oxa-3,7-diaza-bicyclo[3.3.1]non-3-yl]-ethoxy}benzonitrile tri hydrochloride salt (1 g, 2.35 mmol; Prep F) and 3,5-dimethylisoxazole-4-sulfonyl chloride (0.597 g, 3 mmol) were dissolved in DCM (25 mL). Triethylamine (1.95 mL, 3 mmol) was added and the reaction mixture was stirred at room temperature overnight under a nitrogen amosphere. The reaction mixture was concentrated and then redissolved in DCM (25 mL) and transferred to a phase separator. The DCM layer was washed with water (30 mL) and the layers were separated. The retained water was extracted with DCM (25 mL) and the layers were separated. The combined DCM fractions were concentrated under reduced pressure. Purification was performed by precipitation from a mixture of DCM, EtOAc and IPA to give a solid material (0.2 g, 17%).

$^1$H NMR (400 MHz, CDCl$_3$) δ 7.58-7.60 (2H, d), 6.98-7.00 (2H, d), 4.30-4.33 (2H, m), 3.89 (2H, m), 2.98-3.01 (4H, m), 2.69-2.81 (8H, m), 2.64 (3H, s), 2.44-2.46 (2H, t), 2.39 (3H, s).

$^{13}$C NMR (125 MHz, CDCl$_3$) δ 173.11, 162.15 157.69, 134.21, 119.43, 116.30, 115.55, 104.18, 68.62, 67.01, 58.45, 57.50, 54.96, 54.22, 38.97, 12.81, 10.91.

Example 10

N-(2-{7-[2-(4-cyanophenoxy)ethyl]-9-oxa-3,7-diazabicyclo[3.3.1]non-3-yl}ethyl)-N,3,5-trimethylisoxazole-4-sulfonamide N-(2-{7-[2-(4-cyanophenoxy)ethyl]-9-oxa-3,7-diazabicyclo[3.3.1]non-3-yl}ethyl)-3,5-dimethylisoxazole-4-sulfonamide (43 mg, 0.09 mmol, from example 9 above ) and Cs$_2$CO$_3$ (86 mg, 0.26 mmol) were suspended in acetouitrile (2 mL). Iodomethane (17 μl , 0.26 mmol) was added and the reaction mixture was stirred at room temperature overnight under a nitrogen amosphere. More iodomethane (17 μl, 0.26 mmol) was added. The reaction mixture was left to stir for a further 20 h at room temperature overnight under a nitrogen atmosphere. The reaction mixture was filtered and the filtrate was concentrated under reduced pressure. The crude product was purified by chromatography on silica gel using methanol saturated with ammonia in dichloromethane as eluent, which afforded 39 mg (88%) of the title compound.

$^1$H NMR (500 MHz, CDCl$_3$) δ 7.59-7.61 (2H, d), 6.96-6.98 (2H, d), 4.12-4.15 (2H, m), 3.90 (2H, m), 3.23-3.26 (2H, m), 2.98 (3H, s), 2.86-2.92 (4H, m), 2.68-2.75 (4H, m), 2.63 (3H, s), 2.49-2.56 (4H, m), 2.40 (3H, s).

Example 11

N-(2-{7-[2-(4-Cyano-2-fluoro-phenoxy)-ethyl]-9-oxa-3,7-diaza-bicyclo[3.3.1]non-3-yl}-ethyl)-2,4-difluoro-benzenesulfonamide 4-{2-[7-(2-Amino-ethyl)-9-oxa-3,7-diaza-bicyclo[3.3.1]non-3-yl]-ethoxy}-3-fluoro-benzonitrile hydrochloride salt (0.266 g, 0.6 mmol; prep N above) and 2,4-difluorobenzenesulfonyl chloride (0.170 g, 0.80 mmol) were dissolved in DCM (6 mL). Triethylamine (0.416 mL, 3 mmol) was added and the reaction mixture was stirred at room temperature for 20 h under a nitrogen atmosphere. The reaction mixture was concentrated and then redissolved in DCM (3 mL) and transferred to a phase separator. The DCM layer was washed with water (3 mL) and the layers were separated. The retained water was extracted with DCM (3 mL) and the layers were separated. The combined DCM fractions were concentrated under reduced pressure. The crude product was purified by chromatography on silica gel using methanol saturated with ammonia in dichloromethane as eluent, which afforded 173 mg (56%) of the title compound.

$^1$H NMR (500 MHz, CD$_3$OD) δ 7.89-7.94 (1H, m), 7.46-7.50 (2H, m), 7.10-7.26 (3H, m), 4.42-4.45 (2H, t), 3.86 (2H, m), 3.05-3.09 (4H, m), 2.78-2.82 (4H, m), 2.60-2.65 (4H, m), 2.34-2.37 (2H, m).

Example 12

N-(2-{7-[2-(4-Cyano-2-fluoro-phenoxy)-ethyl]-9-oxa-3,7-diaza-bicyclo[3.3.1]non-3-yl}-ethyl)-2,4-difluoro-N-methyl-benzenesulfonamide Cyanomethylenetri-n-butylphosphorane (90%, 0.158 g, 0.59 mmol) was weighed into a microwave vial. N-(2-{7-[2-(4-Cyano-2-fluoro-phenoxy)-ethyl]-9-oxa-3,7-diaza-bicyclo[3.3.1]non-3-yl}-ethyl)-2,4-difluoro-benzenesulfonamide (100 mg, 0.2 mmol, from example 11 above) and THF (2 mL) were added. Methanol (16 μl, 0.39 mmol) was then added and the reaction was heated with microwave irradiation at 160° C. for 15 min. MeOH (1 mL) was added and the reaction was heated with microwave irradiation for a further 10 min in order to consume excess reagent. The reaction mixture was concentrated and the crude product was purified by chromatography on silica gel using methanol saturated with ammonia in dichloromethane as eluent. The product isolated could be purified further by recrystallisation from MeOH to give a solid (55 mg, 53%).

$^1$H NMR (500 MHz, CDCl$_3$) δ 7.85-7.90 (1H, m), 7.42-7.44 (1H, m), 7.34-7.37 (1H, m), 7.09-7.13 (1H, m), 6.93-7.02 (2H, m), 4.23-4.26 (2H, m), 3.88-3.90 (2H, m), 3.28-3.30 (2H, m), 2.99 (3H, s), 2.89-2.95 (4H, m), 2.77-2.79 (2H, m), 2.70-2.72 (2H, m), 2.48-2.54 (4H, m).

Example 13

The following compounds were prepared, from appropriate intermediates (such as those described hereinbefore), according to or by analogy with methods described herein:

(i) N-(2-{7-[(2S)-3-(4-cyanophenoxy)-2-hydroxypropyl]-9-oxa-3,7-diazabicyclo[3.3.1]non-3-yl}ethyl)propane-2-sulfonamide;

(ii) N-(tert-butyl)-3-{7-[3-(4-cyanophenoxy)propyl]-9-oxa-3,7-diazabicyclo[3.3.1]non-3-yl}propane-1-sulfonamide;

(iii) tert-butyl {2-[7-(2-{[(4-fluorophenyl)sulfonyl]amino}ethyl)-9-oxa-3,7-diazabicyclo[3.3.1]non-3-yl]ethyl}carbamate;

(iv) N-[2-(7-benzyl-9-oxa-3,7-diazabicyclo[3.3.1]non-3-yl)ethyl]-4-fluorobenzenesulfonamide;

(v) N-(2-{7-[3-(4-cyanophenoxy)propyl]-9-oxa-3,7-diazabicyclo-[3.3.1]non-3-yl}ethyl)-1-phenylmethanesulfonamide;

(vi) N-(2-{7-[3-(4-cyanophenoxy)propyl]-9-oxa-3,7-diazabicyclo-[3.3.1]non-3-yl}ethyl)propane-2-sulfonamide;

(vii) N-[2-(7-benzyl-9-oxa-3,7-diazabicyclo[3.3.1]non-3-yl)ethyl]-4-cyanobenzenesulfonamide;

(viii) N-(2-{7-[3-(4-cyanophenoxy)propyl]-9-oxa-3,7-diazabicyclo-[3.3.1]non-3-yl}ethyl)benzenesulfonamide;

(ix) N-(2-{7-[3-(4-cyanophenoxy)propyl]-9-oxa-3,7-diazabicyclo-[3.3.1]non-3-yl}ethyl)-2,4-difluorobenzenesulfonamide;

(x) N-(2-{7-[2-(4-cyanophenoxy)ethyl]-9-oxa-3,7-diazabicyclo-[3.3.1]non-3-yl}ethyl)-4-fluorobenzenesulfonamide;

(xi) N-(2-{7-[2-(4-cyanophenoxy)ethyl]-9-oxa-3,7-diazabicyclo-[3.3.1]non-3-yl}ethyl)methanesulfonamide;

(xii) N-(2-{7-[3-(4-cyanophenoxy)propyl]-9-oxa-3,7-diazabicyclo-[3.3.1]non-3-yl}ethyl)-4-fluorobenzenesulfonamide;

(xiii) N-(2-{7-[3-(4-cyanophenoxy)propyl]-9-oxa-3,7-diazabicyclo-[3.3.1]non-3-yl}ethyl)methanesulfonamide;

(xiv) 4-cyano-N-(2-{7-[2-(4-cyanophenoxy)ethyl]-9-oxa-3,7-diazabicyclo[3.3.1]non-3-yl}ethyl)benzenesulfonamide;

(xv) 1-(3-chlorophenyl)-N-(2-{7-[2-(4-cyanophenoxy)ethyl]-9-oxa-3,7-diazabicyclo[3.3.1]non-3-yl}ethyl)methanesulfonamide;

(xvi) 4-cyano-N-(2-{7-[3-(4-cyanophenoxy)propyl]-9-oxa-3,7-diazabicyclo[3.3.1]non-3-yl}ethyl)benzenesulfonamide;

(xvii) N-(2-{7-[3-(4-cyanophenoxy)propyl]-9-oxa-3,7-diazabicyclo-[3.3.1]non-3-yl}ethyl)-1,1,1-trifluoromethanesulfonamide;

(xviii) N-(2-{7-[2-(4-cyanophenoxy)ethyl]-9-oxa-3,7-diazabicyclo-[3.3.1]non-3-yl}ethyl)-1-phenylmethanesulfonamide;

(xix) N-(2-{7-[2-(4-cyanophenoxy)ethyl]-9-oxa-3,7-diazabicyclo-[3.3.1]non-3-yl}ethyl)-1-methyl-1H-imidazole-4-sulfonamide;

(xx) N-(2-{7-[3-(4-cyanophenoxy)propyl]-9-oxa-3,7-diazabicyclo-[3.3.1]non-3-yl}ethyl)butane-1-sulfonamide;

(xxi) N-(2-{7-[3-(4-cyanophenoxy)propyl]-9-oxa-3,7-diazabicyclo-[3.3.1]non-3-yl}ethyl)-1-methyl-1H-imidazole-4-sulfonamide;

(xxii) N-(2-{7-[2-(4-cyanophenoxy)ethyl]-9-oxa-3,7-diazabicyclo-[3.3.1]non-3-yl}ethyl)-1-[4-(trifluoromethyl)phenyl]methanesulfonamide;

(xxiii) N-(2-{7-[3-(4-cyanophenoxy)propyl]-9-oxa-3,7-diazabicyclo-[3.3.1]non-3-yl}ethyl)-1-[4-(trifluoromethyl)phenyl]methanesulfonamide;

(xxiv) N-(2-{7-[3-(4-cyanophenoxy)propyl]-9-oxa-3,7-diazabicyclo-[3.3.1]non-3-yl}ethyl)-3,5-dimethylisoxazole-4-sulfonamide;

(xxv) N-(2-{7-[3-(4-cyanophenoxy)propyl]-9-oxa-3,7-diazabicyclo-[3.3.1]non-3-yl}ethyl)-2-(trifluoromethoxy)benzenesulfonamide;

(xxvi) 1-(3-chlorophenyl)-N-(2-{7-[3-(4-cyanophenoxy)propyl]-9-oxa-3,7-diazabicyclo[3.3.1]non-3-yl}ethyl)methanesulfonamide;

(xxvii) N-(2-{7-[2-(4-cyanophenoxy)ethyl]-9-oxa-3,7-diazabicyclo-[3.3.1]non-3-yl}ethyl)benzenesulfonamide;

(xxviii) 4-cyano-N-{2-[7-(4-cyanobenzyl)-9-oxa-3,7-diazabicyclo-[3.3.1]non-3-yl]ethyl}benzenesulfonamide;

(xxix) 4-cyano-N-{2-[7-(4-fluorobenzyl)-9-oxa-3,7-diazabicyclo-[3.3.1]non-3-yl]ethyl}benzenesulfonamide;

(xxx) 4-cyano-N-(2-{7-[4-(difluoromethoxy)benzyl]-9-oxa-3,7-diazabicyclo[3.3.1]non-3-yl}ethyl)benzenesulfonamide;

(xxxi) 4-cyano-N-(2-{7-[2-(4-fluorophenyl)ethyl]-9-oxa-3,7-diazabicyclo[3.3.1]non-3-yl}ethyl)benzenesulfonamide;

(xxxii) 4-cyano-N-(2-{7-[2-(4-7-fluorophenoxy)ethyl]-9-oxa-3,7-diazabicyclo[3.3.1]non-3-yl}ethyl)benzenesulfonamide;

(xxxiii) 4-cyano-N-(2-{7-[3-(4-fluorophenoxy)propyl]-9-oxa-3,7-diazabicyclo[3.3.1]non-3-yl}ethyl)benzenesulfonamide;

(xxxiv) N-(2-{7-[2-(4-cyanophenoxy)ethyl]-9-oxa-3,7-diazabicyclo-[3.3.1]non-3-yl}ethyl)-2,3-dihydro-1-benzofuran-5-sulfonamide;

(xxxv) 5-chloro-N-(2-{7-[2-(4-cyanophenoxy)ethyl]-9-oxa-3,7-diaza-bicyclo[3.3.1]non-3-yl}ethyl)-1,3-dimethyl-1H-pyrazole-4-sulfonamide;

(xxxvi) 2-cyano-N-(2-{7-[2-(4-cyanophenoxy)ethyl]-9-oxa-3,7-diazabicyclo[3.3.1]non-3-yl}ethyl)benzenesulfonamide;

(xxxvii) N-(2-{7-[2-(4-cyanophenoxy)ethyl]-9-oxa-3,7-diazabicyclo-[3.3.1]non-3-yl}ethyl)-4-methoxybenzenesulfonamide;

(xxxviii) N-(2-{7-[3-(4-cyanophenoxy)propyl]-9-oxa-3,7-diazabicyclo-[3.3.1]non-3-yl}ethyl)-2,3-dihydro-1-benzofuran-5-sulfonamide;

(xxxix) 5-chloro-N-(2-{7-[3-(4-cyanophenoxy)propyl]-9-oxa-3,7-diaza-bicyclo[3.3.1]non-3-yl}ethyl)-1,3-dimethyl-1H-pyrazole-4-sulfonamide;

(xl) N-(2-{7-[3-(4-cyanophenoxy)propyl]-9-oxa-3,7-diazabicyclo-[3.3.1]non-3-yl}ethyl)-4-methoxybenzenesulfonamide;

(xli) 4-cyano-N-(2-{7-[3-(2-fluorophenoxy)propyl]-9-oxa-3,7-diazabicyclo[3.3.1]non-3-yl}ethyl)benzenesulfonamide;

(xlii) 4-cyano-N-(2-{7-[3-(2,5-difluorophenoxy)propyl]-9-oxa-3,7-diazabicyclo[3.3.1]non-3-yl}ethyl)benzenesulfonamide;

(xliii) 4-cyano-N-(2-{7-[3-(3,4-difluorophenoxy)propyl]-9-oxa-3,7-diazabicyclo[3.3.1]non-3-yl}ethyl)benzenesulfonamide;

(xliv) 4-cyano-N-(2-{7-[2-(2-fluorophenoxy)ethyl]-9-oxa-3,7-diazabicyclo[3.3.1]non-3-yl}ethyl)benzenesulfonamide;

(xlv) 4-cyano-N-(2-{7-[2-(4-cyano-2-fluorophenoxy)ethyl]-9-oxa-3,7-diazabicyclo[3.3.1]non-3-yl}ethyl)benzenesulfonamide;

(xlvi) 4-cyano-N-[2-(7-{2-[(4-fluorobenzyl)oxy]ethyl}-9-oxa-3,7-diazabicyclo[3.3.1]non-3-yl)ethyl]benzenesulfonamide;

(xlvii) 4-cyano-N-(2-{7-[2-(3,4-difluorophenyl)ethyl]-9-oxa-3,7-diazabicyclo[3.3.1]non-3-yl}ethyl)benzenesulfonamide;
(xlviii) 4-cyano-N-(2-{7-[2-(3,5-dimethyl-1H-pyrazol-1-yl)ethyl]-9-oxa-3,7-diazabicyclo[3.3.1]non-3-yl}ethyl)benzenesulfonamide;
(xlix) 4-cyano-N-{2-[7-(2-cyanobenzyl)-9-oxa-3,7-diazabicyclo-[3.3.1]non-3-yl]ethyl}benzenesulfonamide;
(l) 4-cyano-N-(2-{7-[(3,5-dimethylisoxazol-4-yl)methyl]-9-oxa-3,7-diazabicyclo[3.3.1]non-3-yl}ethyl)benzenesulfonamide;
(li) N-(2-{7-[2-(4-cyanophenoxy)ethyl]-9-oxa-3,7-diazabicyclo-[3.3.1]non-3-yl}ethyl)-3-fluorobenzenesulfonamide;
(lii) N-(2-{7-[3-(4-cyanophenoxy)propyl]-9-oxa-3,7-diazabicyclo-[3.3.1]non-3-yl}ethyl)-3-fluorobenzenesulfonamide;
(liii) N-(2-{7-[3-(4-cyanophenoxy)propyl]-9-oxa-3,7-diazabicyclo-[3.3.1]non-3-yl}ethyl)-5-methylisoxazole-4-sulfonamide;
(liv) N-{2-[7-(1-benzofuran-3-ylmethyl)-9-oxa-3,7-diazabicyclo-[3.3.1]non-3-yl]ethyl}-4-cyanobenzenesulfonamide;
(lv) 4-cyano-N-{2-[7-(1H-indol-3-yl]methyl)-9-oxa-3,7-diazabicyclo-[3.3.1]non-3-yl]ethyl}benzenesulfonamide;
(lvi) 4-cyano-N-(2-{7-[(5-fluoro-1H-indol-3-yl)methyl]-9-oxa-3,7-diazabicyclo[3.3.1]non-3-yl}ethyl)benzenesulfonamide;
(lvii) N-(3-{7-[2-(4-cyanophenoxy)ethyl]-9-oxa-3,7-diazabicyclo-[3.3.1]non-3-yl}propyl)-4-fluorobenzenesulfonamide;
(lviii) N-(3-{7-[2-(4-cyanophenoxy)ethyl]-9-oxa-3,7-diazabicyclo-[3.3.1]non-3-yl}propyl)-2,4-difluorobenzenesulfonamide;
(lix) N-(3-{7-[3-(4-cyanophenoxy)propyl]-9-oxa-3,7-diazabicyclo-[3.3.1]non-3-yl}propyl)benzenesulfonamide;
(lx) N-{2-[7-(4-cyanobenzyl)-9-oxa-3,7-diazabicyclo[3.3.1]non-3-yl]ethyl}-1-phenylmethanesulfonamide;
(lxi) N-(3-{7-[2-(4-cyanophenoxy)ethyl]-9-oxa-3,7-diazabicyclo-[3.3.1]non-3-yl}propyl)-1-phenylmethanesulfonamide;
(lxii) N-(3-{7-[2-(4-cyanophenoxy)ethyl]-9-oxa-3,7-diazabicyclo-[3.3.1]non-3-yl}propyl)benzenesulfonamide;
(lxiii) 4-cyano-N-(2-{7-[(2-methyl-1H-indol-3-yl)methyl]-9-oxa-3,7-diazabicyclo[3.3.1]non-3-yl}ethyl)benzenesulfonamide;
(lxiv) 4-cyano-N-(2-{7-[2-(3-fluorophenyl)ethyl]-9-oxa-3,7-diazabicyclo-[3.3.1]non-3-yl}ethyl)benzenesulfonamide;
(lxv) 4-cyano-N-(2-{7-[3-(3-fluorophenoxy)propyl]-9-oxa-3,7-diazabicyclo[3.3.1]non-3-yl}ethyl)benzenesulfonamide;
(lxvi) 4-cyano-N-(2-{7-[3-(4-cyano-2-fluorophenoxy)propyl]-9-oxa-3,7-diazabicyclo[3.3.1]non-3-yl}ethyl)benzenesulfonamide;
(lxvii) 4-cyano-N-(2-{7-[3-(4-cyano-2,6-difluorophenoxy)propyl]-9-oxa-3,7-diazabicyclo[3.3.1]non-3-yl}ethyl)benzenesulfonamide;
(lxviii) 4-cyano-N-(2-{7-[2-(2,6-difluorophenoxy)ethyl]-9-oxa-3,7-diazabicyclo[3.3.1]non-3-yl}ethyl)benzenesulfonamide;
(lxix) N-(3-{7-[3-(4-cyanophenoxy)propyl]-9-oxa-3,7-diazabicyclo-[3.3.1]non-3-yl}propyl)propane-2-sulfonamide;
(lxx) N-(3-{7-[3-(4-cyanophenoxy)propyl]-9-oxa-3,7-diazabicyclo-[3.3.1]non-3-yl}propyl)-1-phenylmethanesulfonamide;
(lxxi) N-(3-{7-[3-(4-cyanophenoxy)propyl]-9-oxa-3,7-diazabicyclo-[3.3.1]non-3-yl}propyl)-3,5-dimethylisoxazole-4-sulfonamide;
(lxxii) N-(3-{7-[2-(4-cyanophenoxy)ethyl]-9-oxa-3,7-diazabicyclo-[3.3.1]non-3-yl}propyl)-3,5-dimethylisoxazole-4-sulfonamide;
(lxxiii) N-{3-[7-(4-cyanobenzyl)-9-oxa-3,7-diazabicyclo[3.3.1]non-3-yl]propyl}-3,5-dimethylisoxazole-4-sulfonamide;
(lxxiv) N-{2-[7-(4-cyanobenzyl)-9-oxa-3,7-diazabicyclo[3.3.1]non-3-yl]ethyl}-3,5-dimethylisoxazole-4-sulfonamide;
(lxxv) N-{2-[7-(1,3-benzoxazol-2-ylmethyl)-9-oxa-3,7-diazabicyclo-[3.3.1]non-3-yl]ethyl}-4-cyanobenzenesulfonamide;
(lxxvi) 3-cyano-N-(2-{7-[3-(4-cyanophenoxy)propyl]-9-oxa-3,7-diazabicyclo[3.3.1]non-3-yl}ethyl)benzenesulfonamide;
(lxxvii) 3-cyano-N-(2-{7-[2-(4-cyanophenoxy)ethyl]-9-oxa-3,7-diazabicyclo[3.3.1]non-3-yl}ethyl)benzenesulfonamide;
(lxxviii) 3-cyano-N-{2-[7-(4-cyanobenzyl)-9-oxa-3,7-diazabicyclo-[3.3.1]non-3-yl]ethyl}benzenesulfonamide;
(lxxix) 2-cyano-N-{2-[7-(4-cyanobenzyl)-9-oxa-3,7-diazabicyclo-[3.3.1]non-3-yl]ethyl}benzenesulfonamide;
(lxxx) 2-cyano-N-(2-{7-[3-(4-cyanophenoxy)propyl]-9-oxa-3,7-diazabicyclo[3.3.1]non-3-yl}ethyl)benzenesulfonamide;
(lxxxi) N-(4-cyanobenzyl)-2-[7-(4-cyanobenzyl)-9-oxa-3,7-diazabicyclo-[3.3.1]non-3-yl]ethanesulfonamide;
(lxxxii) N-(4-cyanobenzyl)-2-[7-(2-cyanobenzyl)-9-oxa-3,7-diazabicyclo-[3.3.1]non-3-yl]ethanesulfonamide;
(lxxxiii) N-(4-cyanobenzyl)-N-[(3,5-dimethylisoxazol-4-yl)methyl]-2-{7-[(3,5-dimethylisoxazol-4-yl)methyl]-9-oxa-3,7-diazabicyclo-[3.3.1]non-3-yl}ethanesulfonamide;
(lxxxiv) 4-cyano-N-(3-{7-[2-(4-cyano-2-fluorophenoxy)ethyl]-9-oxa-3,7-diazabicyclo[3.3.1]non-3-yl}propyl)benzenesulfonamide;
(lxxxv) N-(3-{7-[2-(4-cyano-2-fluorophenoxy)ethyl]-9-oxa-3,7-diazabicyclo[3.3.1]non-3-yl}propyl)-4-fluorobenzenesulfonamide;
(lxxxvi) N-(3-{7-[2-(4-cyanophenoxy)ethyl]-9-oxa-3,7-diazabicyclo-[3.3.1]non-3-yl}propyl)-2-fluorobenzenesulfonamide;
(lxxxvii) N-(2-{7-[2-(4-cyanophenoxy)ethyl]-9-oxa-3,7-diazabicyclo-[3.3.1]non-3-yl}ethyl)-2-fluorobenzenesulfonamide;
(lxxxviii) N-(3-{7-[2-(4-cyano-2-fluorophenoxy)ethyl]-9-oxa-3,7-diazabicyclo[3.3.1]non-3-yl}propyl)-2,4-difluorobenzene-sulfonamide;
(lxxxix) N-(3-{7-[2-(4-cyano-2-fluorophenoxy)ethyl]-9-oxa-3,7-diazabicyclo[3.3.1]non-3-yl}propyl)benzenesulfonamide;
(xc) N-(2-{7-[2-(4-cyano-2-fluorophenoxy)ethyl]-9-oxa-3,7-diazabicyclo[3.3.1]non-3-yl}ethyl)-4-fluorobenzenesulfonamide;
(xci) N-(2-{7-[2-(4-cyano-2-fluorophenoxy)ethyl]-9-oxa-3,7-diazabicyclo[3.3.1]non-3-yl}ethyl)-3-fluorobenzenesulfonamide;
(xcii) N-(2-{7-[2-(4-cyano-2-fluorophenoxy)ethyl]-9-oxa-3,7-diazabicyclo[3.3.1]non-3-yl}ethyl)-3,5-dimethylisoxazole-4-sulfonamiide;
(xciii) 3-cyano-N-(2-{7-[2-(4-cyano-2-fluorophenoxy)ethyl]-9-oxa-3,7-diazabicyclo[3.3.1]non-3-yl}ethyl)benzenesulfonamide;

(xciv) N-(2-{7-[2-(4-cyano-2-fluorophenoxy)ethyl]-9-oxa-3,7-diazabicyclo[3.3.1]non-3-yl}ethyl)benzenesulfonamide;

(xcv) N-(2-{7-[2-(4-chlorophenyl)ethyl]-9-oxa-3,7-diazabicyclo-[3.3.1]non-3-yl}ethyl)-4-cyanobenzenesulfonamide;

(xcvi) 4-cyano-N-[2-(7-{2-[4-(trifluoromethyl)phenyl]ethyl}-9-oxa-3,7-diazabicyclo[3.3.1]non-3-yl)ethyl]benzenesulfonamide;

(xcvii) 4-cyano-N-(2-{7-[2-(2,6-difluorophenyl)ethyl]-9-oxa-3,7-diazabicyclo[3.3.1]non-3-yl}ethyl)benzenesulfonamide;

(xcviii) 4-cyano-N-(2-{7-[2-(2-fluorophenyl)ethyl]-9-oxa-3,7-diazabicyclo[3.3.1]non-3-yl}ethyl)benzenesulfonamide;

(xcix) 4-cyano-N-{2-[7-(2-phenylethyl)-9-oxa-3,7-diazabicyclo[3.3.1]non-3-yl]ethyl}benzenesulfonamide;

(c) 4-cyano-N-{2-[7-(4-cyanobenzyl)-9-oxa-3,7-diazabicyclo-[3.3.1]non-3-yl]ethyl}-N-methylbenzenesulfonamide;

(ci) N-[2-(7-benzyl-9-oxa-3,7-diazabicyclo[3.3.1]non-3-yl)ethyl]-4-cyano-N-methylbenzenesulfonamide;

(cii) 4-cyano-N-{2-[7-(4-fluorobenzyl)-9-oxa-3,7-diazabicyclo-[3.3.1]non-3-yl]ethyl}-N-methylbenzenesulfonamide;

(ciii) 4-cyano-N-methyl-N-{2-[7-(2-phenylethyl)-9-oxa-3,7-diazabicyclo[3.3.1]non-3-yl]ethyl}benzenesulfonamide;

(civ) 4-cyano-N-(2-{7-[2-(3-fluorophenyl)ethyl]-9-oxa-3,7-diazabicyclo-[3.3.1]non-3-yl}ethyl)-N-methylbenzenesulfonamide;

(cv) 4-cyano-N-(2-{7-[2-(2-fluorophenyl)ethyl]-9-oxa-3,7-diazabicyclo-[3.3.1]non-3-yl}ethyl)-N-methylbenzenesulfonamide;

(cvi) N-(4-cyanobenzyl)-2-{7-[(3,5-dimethylisoxazol-4-yl)methyl]-9-oxa-3,7-diazabicyclo[3.3.1]non-3-yl}ethanesulfonamide;

(cvii) N-(4-cyanobenzyl)-2-{7-[2-(4-fluorophenyl)ethyl]-9-oxa-3,7-diazabicyclo[3.3.1]non-3-yl}ethanesulfonamide;

(cviii) N-(2-{7-[2-(4-cyano-2-fluorophenoxy)ethyl]-9-oxa-3,7-diazabicyclo[3.3.1]non-3-yl}ethyl)-1-phenylmethanesulfonamide;

(cix) N-(2-{7-[2-(4-cyano-2-fluorophenoxy)ethyl]-9-oxa-3,7-diazabicyclo[3.3.1]non-3-yl}ethyl)-2,3-dihydro-1-benzofuran-5-sulfonamide;

(cx) N-(2-{7-[2-(4-cyanophenoxy)ethyl]-9-oxa-3,7-diazabicyclo-[3.3.1]non-3-yl}ethyl)-2,4-difluorobenzenesulfonamide;

(cxi) N-{2-[7-(4-cyanobenzyl)-9-oxa-3,7-diazabicyclo[3.3.1]non-3-yl]ethyl}-4-fluorobenzenesulfonaimide;

(cxii) 4-fluoro-N-{2-[7-(4-fluorobenzyl)-9-oxa-3,7-diazabicyclo-[3.3.1]non-3-yl]ethyl}benzenesulfonamide;

(cxiii) N-(2-{7-[2-(4-cyanophenyl)ethyl]-9-oxa-3,7-diazabicyclo-[3.3.1]non-3-yl}ethyl)-4-fluorobenzenesulfonamide;

(cxiv) 4-fluoro-N-(2-{7-[2-(4-fluorophenyl)ethyl]-9-oxa-3,7-diazabicyclo-[3.3.1]non-3-yl}ethyl)benzenesulfonamide;

(cxv) 4-cyano-N-(2-{7-[2-(2,6-difluorophenoxy)ethyl]-9-oxa-3,7-diazabicyclo[3.3.1]non-3-yl}ethyl)-N-methylbenzenesulfonamide;

(cxvi) N-(3-{7-[2-(4-cyano-2-fluorophenoxy)ethyl]-9-oxa-3,7-diaza-bicyclo[3.3.1]non-3-yl}propyl)-N-methylbenzenesulfonamide;

(cxvii) N-(2-{7-[2-(4-cyano-2-fluorophenoxy)ethyl]-9-oxa-3,7-diaza-bicyclo [3.3.1]non-3-yl}ethyl)-N-methyl-2,3-dihydro-1-benzofuran-5-sulfonamide;

(cxviii) N-(2-{7-[2-(4-cyanophenoxy)ethyl]-9-oxa-3,7-diazabicyclo[3.3.1]-non-3-yl}ethyl)-N-methyl-2,3-dihydro-1-benzofuran-5-sulfonamide;

(cxix) 4-cyano-N-{2-[7-(4-cyano-2-fluorobenzyl)-9-oxa-3,7-diazabicyclo-[3.3.1]non-3-yl]ethyl}benzenesulfonamide;

(cxx) 4-cyano-N-{2-[7-(4-cyano-2-fluorobenzyl)-9-oxa-3,7-diazabicyclo-[3.3.1]non-3-yl]ethyl}-N-methylbenzenesulfonamide;

(cxxi) 4-fluoro-N-(2-{7-[2-(3-fluorophenyl)ethyl]-9-oxa-3,7-diazabicyclo-[3.3.1]non-3-yl}ethyl)benzenesulfonamide;

(cxxii) 4-fluoro-N-(2-{7-[2-(2-fluorophenyl)ethyl]-9-oxa-3,7-diazabicyclo-[3.3.1]non-3-yl}ethyl)benzenesulfonamide;

(cxxiii) 4-fluoro-N-{2-[7-(2-phenylethyl)-9-oxa-3,7-diazabicyclo[3.3.1]non-3-yl]ethyl}benzenesulfonamide;

(cxxiv) N-{2-[7-(1,2-benzisoxazol-3-ylmethyl)-9-oxa-3,7-diazabicyclo[3.3.1]non-3-yl]ethyl}-4-cyanobenzenesulfonamide;

(cxxv) 4-cyano-N-(2-{7-[2-(4-fluorophenyl)ethyl]-9-oxa-3,7-diazabicyclo[3.3.1]non-3-yl}ethyl)-N-methylbenzenesulfonamide;

(cxxvi) 4-cyano-N-(2-{7-[2-(3,4-difluorophenyl)ethyl]-9-oxa-3,7-diazabicyclo[3.3.1]non-3-yl}ethyl)-N-methylbenzenesulfonamide;

(cxxvii) 4-cyano-N-{3-[7-(4-cyanobenzyl)-9-oxa-3,7-diazabicyclo-[3.3.1]non-3-yl]propyl}benzenesulfonamide;

(cxxviii) 4-cyano-N-{3-[7-(4-fluorobenzyl)-9-oxa-3,7-diazabicyclo-[3.3.1]non-3-yl]propyl}benzenesulfonamide;

(cxxix) 4-cyano-N-(3-{7-[2-(4-fluorophenyl)ethyl]-9-oxa-3,7-diazabicyclo-[3.3.1]non-3-yl}propyl)benzenesulfonamide;

(cxxx) 4-cyano-N-(3-{7-[2-(3-fluorophenyl)ethyl]-9-oxa-3,7-diazabicyclo-[3.3.1]non-3-yl}propyl)benzenesulfonamide;

(cxxxi) 4-cyano-N-(3-{7-[2-(2-fluorophenyl)ethyl]-9-oxa-3,7-diazabicyclo-[3.3.1]non-3-yl}propyl)benzenesulfonamide;

(cxxxii) 4-cyano-N-(3-{7-[2-(2,6-difluorophenyl)ethyl]-9-oxa-3,7-diazabicyclo[3.3.1]non-3-yl}propyl)benzenesulfonamide;

(cxxxiii) 4-cyano-N-(3-{7-[2-(3,4-difluorophenyl)ethyl]-9-oxa-3,7-diazabicyclo[3.3.1]non-3-yl}propyl)benzenesulfonamide;

(cxxxiv) N-[3-(7-benzyl-9-oxa-3,7-diazabicyclo[3.3.1]non-3-yl)propyl]-4-cyanobenzenesulfonamide;

(cxxxv) 4-cyano-N-(3-{7-[3-(4-fluorophenoxy)propyl]-9-oxa-3,7-diazabicyclo[3.3.1]non-3-yl}propyl)benzenesulfonamide;

(cxxxvi) 4-cyano-N-(3-{7-[2-(2,6-difluorophenoxy)ethyl]-9-oxa-3,7-diazabicyclo[3.3.1]non-3-yl}propyl)benzenesulfonamide;

(cxxxvii) 4-cyano-N-(2-{7-[3-(4-fluorophenoxy)propyl]-9-oxa-3,7-diazabicyclo[3.3.1]non-3-yl}ethyl)-N-methylbenzenesulfonamide;

(cxxxviii) 4-cyano-N-(2-{7-[3-(2,4-difluorophenoxy)propyl]-9-oxa-3,7-diazabicyclo[3.3.1]non-3-yl}ethyl)-N-methylbenzenesulfonamide;

(cxxxix) 4-cyano-N-(2-{7-[2-(2,4-difluorophenyl)ethyl]-9-oxa-3,7-diazabicyclo[3.3.1]non-3-yl}ethyl)benzenesulfonamide;

(cxl) 4-cyano-N-(2-{7-[3-(2,4-difluorophenoxy)propyl]-9-oxa-3,7-diazabicyclo[3.3.1]non-3-yl}ethyl)benzenesulfonamide;

(cxli) N-(2-{7-[2-(4-chlorophenyl)ethyl]-9-oxa-3,7-diazabi-cyclo-[3.3.1]non-3-yl}ethyl)-4-cyano-N-methylbenzene-sulfonamide; and (cxlii) 4-Cyano-N-(2-{7-[2-(2,4-difluoro-phenyl)-ethyl]-9-oxa-3,7-diaza-bicyclo[3.3.1]non-3-yl}-ethyl)-N-methyl-benzenesulfonamide;

Example 14

Title compounds of the above Examples were tested in Test A above and were found to exhibit $D_{10}$ values of more than 5.5.

Example 15

Title compounds of the above Examples were tested in Test B above and were found to exhibit $pIC_{50}$ values of greater than 4.5. Indeed the compounds of Examples 1 and 9 were found to have $pIC_{50}$ values of 5.72 and 5.49, respectively.

Abbreviations
Ac=acetyl
API=atmospheric pressure ionisation (in relation to MS)
aq.=aqueous
br=broad (in relation to NMR)
Bt=benzotriazole
t-BuOH=tert-butanol
CI=chemical ionisation (in relation to MS)
mCPBA=meta-chloroperoxybenzoic acid
d=doublet (in relation to NMR)
DBU=diazabicyclo[5.4.0]undec-7-ene
DCM=dichloromethane
dd=doublet of doublets (in relation to NMR)
DMAP=4-dimethylaminopyridine
DMF=N,N-dimethylformamide
DMSO=dimethylsulfoxide
EDC=1-[3-(dimethylamino)propyl]-3-ethylcarbodiimide
Et=ethyl
EtOAc=ethyl acetate
eq.=equivalents
ES=electrospray (in relation to MS)
FAB=fast atom bombardment (in relation to MS)
FBS=foetal bovine serum
h=hour(s)
HC1=hydrochloric acid
HEPES=4-(2-hydroxyethyl)-1-piperazineethanesulfonic acid
HPLC=high performance liquid chromatography
IMS=industrial methylated spirits
IPA=iso-propyl alcohol (propan-2-ol)
m=multiplet (in relation to NMR)
Me=methyl
MeCN=acetonitrile
MeOH=methanol
min.=minute(s)
m.p.=melting point
MS=mass spectroscopy
NADPH=nicotinamide adenine dinucleotide phosphate, reduced form
OAc=acetate
Pd/C=palladium on carbon
q=quartet (in relation to NMR)
RT=room temperature
s=singlet (in relation to NMR)
t=triplet (in relation to NMR)
TEA=triethylamine
THF=tetrahydrofuran
tlc=thin layer chromatography Prefixes n-, s-, i-, t- and tert- have their usual meanings: normal, secondary, iso, and tertiary.

The invention claimed is:
1. A compound which is
(2-{7-[2-(4-cyano-2-fluoro-phenoxy)ethyl]-9-oxa-3,7-diazabicyclo[3.3.1]non-3-yl}ethyl) carbamic acid tert-butyl ester.

* * * * *